(12) United States Patent
Graham et al.

(10) Patent No.: US 7,951,994 B2
(45) Date of Patent: May 31, 2011

(54) DESATURASE ENZYMES

(75) Inventors: Ian Graham, York (GB); Thierry Tonon, Martin des Champs (FR)

(73) Assignee: The University of York, York (GB)

( * ) Notice: Subject to any disclaimer, the term of this patent is extended or adjusted under 35 U.S.C. 154(b) by 987 days.

(21) Appl. No.: 10/597,998

(22) PCT Filed: Feb. 17, 2005

(86) PCT No.: PCT/GB2005/000549
§ 371 (c)(1), (2), (4) Date: Jun. 18, 2007

(87) PCT Pub. No.: WO2005/080578
PCT Pub. Date: Sep. 1, 2005

(65) Prior Publication Data
US 2007/0294790 A1   Dec. 20, 2007

(30) Foreign Application Priority Data

Feb. 17, 2004 (GB) .................................. 0403452.6
Apr. 6, 2004 (GB) .................................. 0407807.7

(51) Int. Cl.
*A01H 5/00* (2006.01)
*C12N 15/82* (2006.01)
*C12N 5/10* (2006.01)
*C12N 1/20* (2006.01)

(52) U.S. Cl. ..... 800/298; 435/69.1; 435/419; 435/252.3

(58) Field of Classification Search ........................ None
See application file for complete search history.

(56) References Cited

U.S. PATENT DOCUMENTS

2008/0155705 A1* 6/2008 Zank et al. ...................... 800/13

* cited by examiner

*Primary Examiner* — Elizabeth F McElwain
(74) *Attorney, Agent, or Firm* — Kening Li; Pinsent Masons LLP

(57) ABSTRACT

We describe transgenic cells transformed with nucleic acid molecules which encode enzymes with desaturase activity and the use of these cells and enzymes in biocatalysis.

15 Claims, 27 Drawing Sheets

Table 1

| Fatty acid | Mol % of total fatty acids |
|---|---|
| 14:0 | 11.50 |
| 16:0 | 17.95 |
| 16:1Δ9 | 19.81 |
| 16:1Δ11 | 0.19 |
| 16:2Δ9,12 | 2.47 |
| 16:3Δ6,9,12 | 6.68 |
| 18:0 | 0.47 |
| 18:1Δ7 | 0.26 |
| 18:1Δ9 | 1.50 |
| 18:1Δ11 | 1.52 |
| 18:2Δ9,12 | 2.37 |
| 18:3Δ6,9,12 | 0.98 |
| 18:3Δ9,12,15 | 0.32 |
| 18:4Δ6,9,12,15 | 5.72 |
| 20:0 | 0.44 |
| 20:3Δ8,11,14 | 0.26 |
| 20:4Δ5,8,11,14 | 2.46 |
| 20:5Δ5,8,11,14,17 | 17.51 |
| 22:6Δ4,7,10,13,16,19 | 6.64 |
| 24:0 | 0.49 |

Table 2

| Fatty acid | Mol % of total fatty acid methyl esters | | | | | | | |
|---|---|---|---|---|---|---|---|---|
| | - substrate | | + 14:0 | | +16:0 | | + 18:0 | |
| | pYES2 | pYDESN | pYES2 | pYDESN | pYES2 | pYDESN | pYES2 | pYDESN |
| 14:0 | 0.78 | 0.52 | 1.12 | 0.96 | 0.76 | 0.58 | 0.76 | 0.70 |
| 14:1Δ9 | 0.22 | 0.13 | 1.20 | 1.29 | 0.23 | 0.14 | 0.23 | 0.20 |
| 16:0 | 18.40 | 15.04 | 18.37 | 14.62 | 23.85 | 22.09 | 17.22 | 15.09 |
| 16:1Δ9 | 39.73 | 35.55 | 43.39 | 36.24 | 42.24 | 37.03 | 36.24 | 31.67 |
| 16:1Δ11 | 0.23 | 3.27 | 2.36 | 5.84 | 0.22 | 5.57 | 0.25 | 5.84 |
| 18:0 | 7.37 | 7.34 | 6.61 | 7.23 | 6.36 | 6.60 | 16.72 | 17.47 |
| 18:1Δ9 | 30.19 | 34.32 | 24.44 | 30.24 | 23.89 | 25.19 | 26.07 | 26.58 |
| 18:1Δ11 | 1.20 | 1.21 | 1.35 | 1.30 | 1.19 | 1.12 | 1.08 | 0.96 |
| 26:0 | 1.89 | 2.63 | 1.16 | 2.29 | 1.26 | 1.70 | 1.43 | 1.50 |

| TABLE 3 | | % conversion | |
|---|---|---|---|
| substrate | product | *Thalassiosira pseudonana* | *Phaeodactylum tricornutum* |
| 16:1Δ9 | 16:2Δ6,9 | 14 | 6 |
| 18:1Δ9 | 18:2Δ6,9 | 18 | 5 |
| 18:2Δ9,12 | 18:3Δ6,9,12 | 54 | 28 |
| 18:3Δ9,12,15 | 18:4Δ6,9,12,15 | 68 | 27 |

```
MDFLSGDPFRTLVLAALVVIGFAAAWQCFYPPSIVGKPRT    40
LSNGKLNTRIHGKLYDLSSFQHPGGPVALSLVQGRDGTAL    80
FESHHPFIPRKNLLQILSKYEVPSTEDSVSFIATLDELNG   120
ESPYDWKDIENDDFVSDLRALVIEHFSPLAKERGVSLVES   160
SKATPQRWMVVLLLLASFFLSIPLYLSGSWTFVVVTPILA   200
WLAVVNYWHDATHFALSSNWILNAALPYLLPLLSSPSMWY   240
HHHVIGHHAYTNISKRDPDLAHAPQLMREHKSIKWRPSHL   280
NQTQLPRILFIWSIAVGIGLNLLNDVRALTKLSYNNVVRV   320
EKMSSSRTLLHFLGRMLHIFVTTLWPFLAFPVWKAIVWAT   360
VPNAILSLCFMLNTQINHLINTCAHASDNNFYKHQVVTAQ   400
NFGRSSAFCFIFSGGLNYQIEHHLLPTVNHCHLPALAPGV   440
ERLCKKHGVTYNSVEGYREAIIAHFAHTKDMSTKPTD     477
```

FIGURE 5a

```
CGGAGGGCGCACTGGAGAGGTTCCCGGAGGTTTGATGTAATTGGAGGTTGGGTCAAATAC
AGATTCTGCCCTAACATTTTCCGGAAATTGGCTTCAGTTTGATTCAAGCGAGGAGGCGCT
CGGCAGGAGGGCCCGTCACCTTTTTGCATATTTGGGACTTCAATGGTTTCTACATTTTTT
CCTTTCTGGAACCCAAACGCTGTCCTTCAATTCTCCTTCCCATACTCACGGATGGATCCC
CGAAAATGCCACCACCAATCACCCTTGTCAATCNCAAACCTCGTCATCCTTCACATTTTC
TTAGCACCATTGGCCGGTGTACCCTTCCCCGCGACTGCCAGTCTATGGGTCAGTATATCT
CCCACATTTGGAGAGGTATTGCTAAAACGTGTCAATCATACATATGATAACTGGAGAGTG
CACACGAAGAGATCAATGCTTGAGCTAGGAGGGTGGCTATTGGCTGTGAGCGGCAGCTTT
CACTTAAGATATTACGGCACGGCAAGTCTACTCGACAATACAACCGATGCTGCAGGTTTA
TGCAATAGCTCAAGTTGTATCAACAACAAAACGTGCGAGAATGACGACAGTGCTTACGAA
GATGATGCCATGAGAGCTGTTTGGGCATTGCTATGGGCGTTGCAGCTGGGAACGTTGGTC
GGTTGTGCGTTAGTGTTAGGAGTGCATCATTTCAGTGGAGATAACCTGACCAAACAATCT
GCGATACCAACAAAATCTTCAAAAGCAAAGCCAATATCTGATCAAAAAGCAGCTGTGACA
TCCGGCAGTACCTGCGCTGTGAGAGAGAAGGCACGAAAAGACGGTCTAGTACTCCTCGAT
GGCAACTGGTACAACGTTGAAAAGTTCGTCCATCATCATCCTGGAGGTGTAGAAGTGTTG
GAGCAGTATCTCGGGGCAGATATCTCGTTTGTGTTTAGAGTGATGCATAGAAATCCAACT
CAAATCATGAAATATCGCAAGCCGGTACGAGCTGCCACCCCAGAAGAACTTGAGGCTCTC
ACAAGCCGCCGTCAAGAGGTTTGTCTTGATATGATGGACGACTTTGTTACCAATTCCATT
GATATCGCTTCTCCAGAAATGCTTCCCAAGCCAACGCAGTTTGACCTGAAGTCATTTGAG
AAGGACTTCATTGACTTATATGAAGAGTTTGTTGCTCAGGGATACTTCAAGCCCTCAACA
ACATGGCTACTCTGGAACACAGCGGTACTGATTAGTATCATCGCGTTATCTGTCATCTCA
ATGAAAGTGCTACCACCAACTTCGTTTGTCCTACCTGGAGCATTGCTTGGTCTCTTTTGG
CACCAAAGTGGATTCCTCATGCACGATGCCGAGCACCATAATTTGGCTGGAAACGAACGG
CTGAATGACATTTTGGGTTGGATCTATGGCACTGTCTTCTTGGGTGTCAATGGCGCTTGG
TGGAGAGAGGAGCATAGAGAACATCATGCTTTCCTCAACACTTACGATGATGAAAGTGGT
TTCAAAGATCCCCAGGTGTGTCAGCGTCACTGTAGACGACTTCAAAGTTACTTGTTCCTC
TCGTTGCTCACACATTCGATTTTATTCATTCACTCACAGATGAGAGAGGACGTCTGGATA
CAGAACAAGAAGTTGATTCCGTTCTTCGGTGACGAGATCATTCATTTCTTAACAAACTTT
CAGCACATTCTGTTCCTTCCGATCATCTTTATCGTTGGCCGCGTTGGTATTGTCGTAGAT
TCTACACTGACTGAGAGGAAGTTCCGTCCTTGGAGTAAGTGTCAATTGGTATTCATTGAG
AAGGAACTGCTGATTTGACTTTCATACTAACTAACTGCATCGCCACTTCATCACGACGAT
AGCAATACTTGGTAATGTTTGTCATATCCTACTACACTACGCAATCTTATCTCAGACGAG
TCGTCCTATCCCCGTGTACATCATCGGCTCTCTTTGGCAAGCTATTCTCTCTTTGCAATT
GCTTGGGAATCACTACGTCAAGCCTTGGAATAGACTCAACGATGCCACAGAGGGAAACTT
CTGCGTTTGGCAGATACTAAGCACTCAAGACTTTGCATGTCCACGTTGGTCTCGGTGGCT
GTACGGAGGTCTCAACTTTCACTATTCCCATCATCTATTCCCAACGTTGTCTAGAGAGTA
CTTTCACATTACATCACCACGCATTCGGGTGAGTGCTCGTGTTTAGTGTTGCTACATTCA
TATCAATGATACTCATAGCTCCATTTCTTTCGACAGAGACTATGTGAAGAAGCACGGGCTT
CCGTTTATTGAGATTGCGTTCATTGATTGCGTTGTTGGAATGGTCAACAACTTTAACGAA
GTGAGGAAAGACTTCGCTACGAAAGGCCACGGGAGTGTGGCTTTCATGTACACGTGATCT
TAAGTGTCGAGACGATATAGAGGTTGATATTTACTGTTTTGTCACCAGTAGTTCGTCTAA
TATGATGTAGCAACCGCAGCTTGTGGAATTAGTTTAGTGTACTATGTAACTGAAAAAGTT
ACGTCGATCTACTCTCTGCACATCTACATCGTGTGAAGCCATTCCGTTCAAGAAGTATCC
TAATCCCTCGAACCAAACAGTCTCGTCCTATACCCATCATTAATCAGCCGCCTCTACCCG
ATGTTGCTGTTGTTGCGGCTGCTGCTGAACCCCCTCGCCGCCCGATAATGGCGAAGGGCA
GTCGGACACTTGATAATCTTCTTCACAGAGTTTATGAGCTGGGTGTTTGTACCAATACCT
CCTTTATATGGTACTAATGGACCCGTGTCCATTATTGCTTGGCCGCGTTTCCACCGTTTG
GACCGATAGGTGGCCAAAGGCCCACACAGAAGAGCACCATAAAGGCGCAGCCTTGAGGAA
ACTCAAGAAACCCCGATGGTCCACGTATTAAAAC
```

Figure 5b

```
ATGGCTAGAGCTGTTTGGGCATTGCTATGGGCGTTGCAGCTGGGAACGTTGGTCGGTTGT
GCGTTAGTGTTAGGAGTGCATCATTTCAGTGGAGATAACCTGACCAAACAATCTGCGATA
CCAACAAAATCTTCAAAAGCAAAGCCAATATCTGATCAAAAAGCAGCTGTGACATCCGGC
AGTACCTGCGCTGTGAGAGAGAAGGCACGAAAAGACGGTCTAGTACTCCTCGATGGCAAC
TGGTACAACGTTGAAAAGTTCGTCCATCATCATCCTGGAGGTGTAGAAGTGTTGGAGCAG
TACCTCGGGGCAGATATCTCGTTTGTGTTTAGAGTGATGCATAGAAATCCAACTCAAATC
ATGAAATATCGCAAGCCGGTACGAGCTGCCACCCCAGAAGAACTTGAGGCTCTCACAAGC
CGCCGTCAAGAGGTTTGTCTTGATATGATGGACGACTTTGTTACCAATTCCATTGATATC
GCTTCTCCAGAAATGCTTCCCAAGCCAACGCAGTTTGACCTGAAGTCATTTGAGAAGGAC
TTCATTGACTTATATGAAGAGTTTGTTGCTCAGGGATACTTCAAGCCCTCAACAACATGG
CTACTCTGGAACACAGCGGTACTGATTAGTATCATCGCGTTATCTGTCATCTCAATGAAA
GTGCTACCACCAACTTCGTTTGTCCTACCTGGAGCATTGCTTGGTCTCTTTTGGCACCAA
AGTGGATTCCTCATGCACGATGCCGAGCACCATAATTTGGCTGGAAACGAACGGCTGAAT
GACATTTTGGGTTGGATCTATGGCACTGTCTTCTTGGGTGTCAATGGCGCTTGGTGGAGA
GAGGAGCATAGAGAACATCATGCTTTCCTCAACACTTACGATGATGAAAGTGGTTTCAAA
GATCCCCAGATGAGAGAGGACGTCTGGATACAGAACAAGAAGTTGATTCCGTTCTTCGGT
GACGAGATCATTCATTTCTTAACAAACTTTCAGCACATTCTGTTCCTTCCGATCATCTTT
ATCGTTGGCCGCGTTGGTATTGTCGTAGATTCTACACTGACTGAGAGGAAGTTCCGTCCT
TGGACAATACTTGGTAATGTTTGTCATATCCTACTACACTACGCAATCTTATCTCAGACG
AGTCGTCCTATCCCCGTGTACATCATCGGCTCTCTTTGGCAAGCTATTCTCTCTTTGCAA
TTGCTTGGGAATCACTACGTCAAGCCTTGGAATAGACTCAACGATGCCACAGAGGGAAAC
TTCTGCGTTTGGCAGATACTAAGCACTCAAGACTTTGCATGTCCACGTTGGTCTCGGTGG
CTGTACGGAGGTCTCAACTTTCACTATTCCCATCATCTGTTCCCAACGTTGTCTAGAGAG
TACTTTCACATTACATCACCACGCATTCGGAGACTATGTGAGAAGCACGGGCTTCCGTTT
ATTGAGATTGCGTTTATTGATTGCGTTGTTGGAATGGTCAACAACTTTAACGAAGTGAGG
AAAGACTTCGCTACGAAAGGCCACGGGAGTGTGGCTTTCATGTACACGTGA
```

Figure 5c

```
MARAVWALLW ALQLGTLVGC ALVLGVHHFS GDNLTKQSAI PTKSSKAKPI SDQKAAVTSG
STCAVREKAR KDGLVLLDGN WYNVEKFVHH HPGGVEVLEQ YLGADISFVF RVMHRNPTQI
MKYRKPVRAA TPEELEALTS RRQEVCLDMM DDFVTNSIDI ASPEMLPKPT QFDLKSFEKD
FIDLYEEFVA QGYFKPSTTW LLWNTAVLIS IIALSVISMK VLPPTSFVLP GALLGLFWHQ
SGFLMHDAEH HNLAGNERLN DILGWIYGTV FLGVNGAWWR EEHREHHAFL NTYDDESGFK
DPQMREDVWI QNKKLIPFFG DEIIHFLTNF QHILFLPIIF IVGRVGIVVD STLTERKFRP
WTILGNVCHI LHYAILSQT SRPIPVYIIG SLWQAILSLQ LLGNHYVKPW NRLNDATEGN
FCVWQILSTQ DFACPRWSRW LYGGLNFHYS HHLFPTLSRE YFHITSPRIR RLCEKHGLPF
 IEIAFIDCVV GMVNNFNEVR KDFATKGHGS VAFMYT
```

Figure 6a

NANCCATATGCGGGAATACGGCCAGGGTATACCCACAGCGCCTCCGTTGC
AGCAAACTCCTATCCAATACCTCCCCATGAACCCCCCCTTCGGCCACCCT
ATATGCGAGACTCGTTCGTCTGGACCTGCAGATGATGACTGGTGAGGCCA
AATTAGTTGGGAATGCGTGCAGATGGAGGCCTTATTCTTTTGCAATCAGG
GGCGTCGTCAAGAGGAGATCCATGTTGTTGTGTGATTCGACTTGCTTGGG
GCGTGCATGATGTGTGCGTGCGTGTACGATGTTGATAGGTAGAAAGAGAT
CGAGGCGGTGATTCAACTATTCAGGATACTGAAAGAGTTGATATAGCAGC
AGTAATATATCCTAGTTGTTTGTGTTTGTGTTGTGGTGTATCAAGTATTC
AATGACGCAACAATAACGTTGGTAGTGTATGGGTGAACAGGTGTTCGGGA
CAAAGGCTTTTCATAAAATCTATTTAACGTGTTCGTTAAAACGACGAAAA
GAAGCCACTCTGCACCATTCCAGCGCAGACAAGACCAGCAGGCACAGAAC
AGCACGACACACCGACCCGAGCCGAAAAAGCCAACAACAACGACACCGAC
CCGAGCCGATACAGCCGACAGGCAAAGGCTCTCTGCTACAATCTACAAAA
CGGCAACATCAAATCATGCCACCCTCCATCAAAGACACACTCGACGAGCC
CTTCGTCTCGCCCGCATCCACCAAGTCGCCCACCACCAAACCCCTCCTCC
CCCGCCGCAAACCCCTCAAACGATACTCCCCCTCCCAAATCTCCCAACAC
AACACTCCCACCGATGCATGGCTCATTTACAAATCCCAAGTCCTTGACAT
TTCCAAATGGATATCGCACCATCCAGGTGGAGAGCAGACGCTGTTGAGGT
TTGCCGGTATGGATGCTACCGATGAATTGAGGGCATTTCATGATGATTGG
GTTTTGGAGGAGAAGTTGCCTCATTTTGTGATTGGGGAGGTGGATTGGAC
TACTACCGGCGGGGCAGAGAATACTGTCACGAAGGATGGACAGGTTTCGG
AGCTTATCAAGGATTTCAGAGAGTTGGGTGAACACTTCGACAGGTTGGGG
TACTTTCACGTCAGTCCATGGTATTACGTCCGTAAGGTGGCTACCGTCTT
CGCCATCTTTGGATGTGCACTCGGACTCCTCTTCAATACCGATTCCATCC
CAGCACACATGCTCGCGGCGGTACTCCTCGGTATATTCTGGCAACAATTT
GCATTCGTCGGACATGACTGTGGTCACATGTCGGCGCGGACTCATGCCCG
TGATCATATCGATGTACCTAAGCTGGGAGCACTGGTGACCTTCTTCAATG
GGATTTCGGTAGCGTGGTGGAAGGCTACGCACAATGTTCATCATGCTGTG
CCAAATAGTGTTGATTGTGACCCGGACATTGCTCATTTGCCGGTGTTTGC
GTTGCATGAGCACATGTTTACGTCGTTGTTTAACAAGTATCATGGGAGGG
TGATGGAGTTTGATTGGCTGGCGCGTAATGTCTTTGTGCCATTTCAACAC
TTTTGGTACTATCCCATAATGGCGGTGGCGAGGTTCAATCTGTACATTCA
ATCAGCATTGTTTTTGGCGTCGAAGAACGATGGGCATGCAGGAAGAAGGG
GATCCTCTAGATTGGATTTGCTGGCGTTCAATCGTGTTCTTCTGTTGGTT
AGCGGTGCTGGTGTCATGCATCCCGAGCTGGGCGGAGCGTATCGCATTCG
TCTTCGTCAGACATGCTGTACCTGGGTTACTGCATGTGCAATCACCTGTC
GCCTTCTCTTGGACAATCTTGATCCCACAAGAGGACCCGGTTGGGGTGCT
CTTTCCGAAGCCCGGTTCTGGGCTTTTGCCACATTGGCGTCCCGGGTCCA

Figure 6b

MPPSIKDTLD EPFVSPASTK SPTTKPLLPR RKPLKRYSPS QISQHNTPTD AWLIYKSQVL
DISKWISHHP GGEQTLLRFA GMDATDELRA FHDDWVLEEK LPHFVIGEVD WTTTGGAENT
VTKDGQVSEL IKDFRELGEH FDRLGYFHVS PWYYVRKVAT VFAIFGCALG LLFNTDSIPA
HMLAAVLLGI FWQQFAFVGH DCGHMSARTH ARDHIDVPKL GALVTFFNGI SVAWWKATHN
VHHAVPNSVD CDPDIAHLPV FALHEHMFTS LFNKYHGRVM EFDWLARNVF VPFQHFWYYP
IMAVARFNLY IQSALFLASK NDGHAGRRGS SRLDLLAFNR VLLLVSGAGV MHPELGGAYR
IRLRQTCCTW VTACAITCRL LLDNLDPTRG PGWGALSEAR FWAFATLASR V

Figure 6c

ATGGCTCCACCCTCCATCAAAGACACACTCGACGAGCCCTTCGTCTCGCCCGCATCCACC
AAGTCGCCCACCACCAAACCCCTCCTCCCCCGCCGCAAACCCCTCAAACGATACTCCCCC
TCCCAAATCTCCCAACACAACACTCCCACCGATGCATGGCTCATTTACAAATCCCAAGTC
CTTGACATTTCCAAATGGATATCGCACCATCCAGGTGGAGAGCAGACGCTGTTGAGGTTT
GCCGGTATGGATGCTACCGATGAATTGAGGGCATTTCATGATGATTGGGTTTTGGAGGAG
AAGTTGCCTCATTTTGTGATTGGGGAGGTGGATTGGACTACTACCGGCGGGGCAGAGAAT
ACTGTCACGAAGGATGGACAGGTTTCGGAGCTTATCAAGGATTTCAGAGAGTTGGGTGAA
CACTTCGACAGGTTGGGGTACTTTCACGTCAGTCCATGGTATTACGTCCGTAAGGTGGCT
ACCGTCTTCGCCATCTTTGGATGTGCACTCGGACTCCTCTTCAATACCGATTCCATCCCA
GCACACATGCTCGCGGCGGTACTCCTCGGTATATTCTGGCAACAATTTGCATTCGTCGGA
CATGACTGTGGTCACATGTCGGCGCGGACTCATGCCCGTGATCATATCGATGTACCTAAG
CTGGGAGCACTGGTGACCTTCTTCAATGGGATTTCGGTAGCGTGGTGGAAGGCTACGCAC
AATGTTCATCATGCTGTGCCAAATAGTGTTGATTGTGACCCGGACATTGCTCATTTG
CCGGTGTTTGCGTTGCATGAGCACATGTTTACGTCGTTGTTTAACAAGTATCATGGGAGG
GTGATGGAGTTTGATTGGCTGGCGCGTAATGTCTTTGTGCCATTTCAACACTTTTGGTAC
TATCCCATAATGGCGGTGGCGAGGTTCAATCTGTACATTCAATCAGCATTGTTTTGGCG
TCGAAGAACGATGGGCATGCAGGAAGAACAACATTGGATTTGATGGCGTTCATCGGCTTC
TTCTCTTGGTTAGCGGTGCTGGTGTCATGCATCCCGAGCTGGCCGGAGCGTATCGCATTC
GTCTTCGTCAGCCATGCTGTAGCTGGGTTACTGAATGTGCAAATCACACTGTCGCACTTC
TCTCGGCCAATCTTTGATACCAACAAAGAGGGACCCAGGTTTGGAGGTGACTTTTACTCT
CGTAACGTCCTTGCTTCGTTGGACGTCGCTTGTCCTACATACTTGGACTGGTTCCACGGA
GGTCTCCAATTCCAAACACTCCATCATTGCTACCCTAGACTTGGACGTCAGCACTTGAGA
AAGACCGAACCTCTCATTGCATCGTTGTGCAAGAAGCATTCTTTACCATACACGAGCAAG
AGCTTCGTAGAGTGCAATATGGAAGTTTTTAATACATTGAAGGATGCCGCGCGTTCTGCC
AAGAAGTGGTCACCGTTAATTTATGAGTCAATGTGTGCTCAGGGATAG

Figure 6d

MAPPSIKDTL DEPFVSPAST KSPTTKPLLP RRKPLKRYSP SQISQHNTPT DAWLIYKSQV
LDISKWISHH PGGEQTLLRF AGMDATDELR AFHDDWVLEE KLPHFVIGEV DWTTTGGAEN
TVTKDGQVSE LIKDFRELGE HFDRLGYFHV SPWYYVRKVA TVFAIFGCAL GLLFNTDSIP
AHMLAAVLLG IFWQQFAFVG HDCGHMSART HARDHIDVPK LGALVTFFNG ISVAWWKATH
NVHHAVPNSV DCDPDIAHLP VFALHEHMFT SLFNKYHGRV MEFDWLARNV FVPFQHFWYY
PIMAVARFNL YIQSALFLAS KNDGHAGRTT LDLMAFIGFF SWLAVLVSCI PSWPERIAFV
FVSHAVAGLL NVQITLSHFS RPIFDTNKEG PRFGGDFYSR NVLASLDVAC PTYLDWFHGG
LQFQTLHHCY PRLGRQHLRK TEPLIASLCK KHSLPYTSKS FVECNMEVFN TLKDAARSAK
KWSPLIYESM CAQG

Figure 7a

```
CANCTAACCGGGAAGAGGGCCTTATTTGCCACCACAGTGATAACCTTCGG
CTGTGACCACGGGAGCAGCCGTGGCGAGCCCGCGTCTGACCAGCCCTGTC
TTTTTGGAGCATCCCTCACCACACATCGCATCTCGTTGCACGGGGATCAG
TGCACAGTCTTCGTCTCATTGTTAGATGTACACGCGAAGAAGCACATCCA
GCCCGACTCTTCATAACATCTCAGGACCCTGCAAACACGCATCACATCAT
GATGTTCCACCGAGTCGTCATCGGCATCGCCCTCACAATGGGCTGTGTCT
CCAGTTTCTCCTCGCCCGGTCATTCAATATTGGCACGTCCTATGCAATCA
TCCACCACTTCTCGTTTCTCGACAATGATTGAAAAGTCAGAGATTTCTGA
CAGTGTCAACAACGAAAACAAGGAGATGACATCATCTTCTGAAATGCCTA
CTGCGTGGGAATGCAATGAGGAAGCTGAGTGCGTGGAAGTTCCTGCTTGT
GATGACGAGGAATGCCGTACTACTTTGGATGTGAGGATTCATGGCAAATG
GTACGATCTTTCAGGTGAGTGCAAGTTGTGGTATGCATTGTTATAAGTTC
TATTCTGTATCGGCACACACGATATTGTGTTGTGATCAATGTTCTAACAG
CCATTTGTTCCTCCTACTTCCTCAGGATGGCGCAAAGCTCACCCTGCAGG
ACCCCACTGGATCGACTGGTACGACGGTCGTGACGCCACCGAAGTCATGG
ACGCATTTCACACCCAAAAAGGACGTGAAATGTACAAGCGTCTTCCCGCG
TCTGCCCCCGAAACGGCTGCCGTTCTTGAAGCATCTGCAGCACCTTACTC
GCAGACGGAGCTTAACTTTAGGAAGTTGAGGGATCAATTGGAAAGTGAGG
GGTGGTGGAGAGGGACTTTGTCCATGAGGGAAAGTTGCTGGCGATTTGG
GCATCGTTGGTTACAGGAGCAGCATTGACTGCGGAGAGTGCTCCTCCTCT
TTCAACTTTCTTGTTGGGATTGTCTATGACGAATGCTGGATGGTTGGGGC
ATGATTATATTCATGGTGTTGATAAGTTCAGTCAAGTTATGAGGCCTTTT
GCTGCCGTGGCTGCTGGTTTGGGACCAACTTGGTGGAGTGATAAGCACAA
CAAGCATCACGCTTTGAGTGAGTCTGACTCTTGTTGTTACTGCAAGTGTG
GTTTAAAGATTGAATCAATACCATCGTACTCATATCCTCAACATTCTTTC
AATCGCAACAGCCAACGAAATGGGAGTTGATGAAGACATTGCGACCGATC
CATTTCTCTTTCCTTATGTCCCGGATCCAAAGTACGATTCTCCACTTCGT
AAGATCCAACACTACATCTTCTACAGTCCCTTCTCCTTCCTCTTTGCCCT
CTGGCGCGTGGACACCCTTAAGGTCGCCGTAGACTCAGTTGAATCGAAAC
GTCCCGATGCAAAGAATGAATTGTGGTATCTCTTGGCACATTACTTCGTC
TTGTTGACCTTCTTCCCAGCTCAGGTGTGGGTGCCTGCTGTCTTCCTCTC
TGGCCTCATGTCTGCACTCATTGTTACTCCGACACATCAGTCGGAAGAGT
ATTTTGAGGAGTATCAGCCTGATTGGGTGACGGCTCAGTTTGAGAGCACG
AGAAATGCTGTCACGACTAATCCATTCTCTGAGTGGCTTTGGGGAGGAAT
GCAATACCAGTTGGAGCATCACTTGTTCCCTTCCATGCCCAGGTAAGCAG
CTTAATGTTTGTATCTTGTACCATTGTTGACTTCTCGTTCTCGGCTAACN
CTGTTGGAAGCGTATGAGCCTAGCACATAATGGTGTGTATGCGACCATGA
ACTCGATTTAAGGTTCAAATACCTTACTATCATCTCAGTCCGGTGCCGGA
TGACGTGTGTCCC
```

Figure 7b

| | | | | | |
|---|---|---|---|---|---|
| QPFVPPTSSG | WRKAHPAGPH | WIDWYDGRDA | TEVMDAFHTQ | KGREMYKRLP | ASAPETAAVL |
| EASAAPYSQT | ELNFRKLRDQ | LESEGWWERD | FVHEGKLLAI | WASLVTGAAL | TAESAPPLST |
| FLLGLSMTNA | GWLGHDYIHG | VDKFSQVMRP | FAAVAAGLGP | TWWSDKHNKH | HALSESDSCC |
| YCKCGLKIES | IPSYSYPQHS | FNRNSQRNGS | | | |

| | | | | | |
|---|---|---|---|---|---|
| RLNQYHRTHI | LNILSIATAN | EMGVDEDIAT | DPFLFPYVPD | PKYDSPLRKI | QHYIFYSPFS |
| FLFALWRVDT | LKVAVDSVES | KRPDAKNELW | YLLAHYFVLL | TFFPAQVWVP | AVFLSGLMSA |
| LIVTPTHQSE | EYFEEYQPDW | VTAQFESTRN | AVTTNPFSEW | LWGGMQYQLE | HHLFPSMPR |

Figure 8a

```
AAAAAAAAAAAAANNNNGGGAAGCGAGATCAATCGAGCTGGTACCATGAG
TTTCAAAAGTCAACTTCAACATTCAAGTTGTACAAAAGAGAGGGCCTCAG
ACGTGGTGAGCAAAAGCACTTCACAGGGGAATAGTAGGGGAAAAACAGAA
ATATTTGGCAAATTTATCTTAGTTCCTGATTATATCTTCAATTACTAAAG
GGAAAACAATGCAGCTCAAAAGCTACGTTTGTGTACTTCTTTGAAACCAC
CTCACCCCCGCGGCTTCGCGTCCGGGTCGGCCCGCTTGCATCCTTTCTTC
CTCTCACAATTTATCATCCAACGAGCTGATAACGTGTCATTTCACAGGGT
CAACACAATAAAACATACTAATCAACC<u>ATG</u>GGAAAAGGAGGAGACGCAGC
CGCAGCCACCAAGCGTAGTGGAGCATTGAAATTGGCGGAGAAGCCGCAGA
AGTACACCTGGCAGGAGGTGAAGAAGCACGTGAGTCTCCGCTTGTGTTGC
TGCCGTTGGATGTCCTTGTCGTTGGTTCGGATTATGCAACGAGAGTTCGT
ATTGCAACTCAATTTCAATTGTCCATCTGCAATCAACTCATCTGACCCAA
CAACTTCTGCCACCGTCCACCCATTCAGATCACCCCCGACGATGCCTGGG
TAGTCCACCAAAACAAAGTCTACGACGTCTCCAACTGGTACGACCACCCC
GGTGGAGCCGTGGTGTTCACCCACGCCGGAGACGACATGACGGACATCTT
CGCCGCCTTCCACGCCCAAGGCTCTCAGGCCATGATGAAGAAGTTTTACA
TTGGAGATTTGATTCCGGAGAGTGTGGAGCATAAGGATCAAAGACAGTTG
GATTTCGAGAAGGGATATCGTGATTTACGGGCCAAGCTTGTCATGATGGG
GATGTTCAAGTCGAGTAAGATGTATTATGCATACAAGTGCTCGTTCAATA
TGTGCATGTGGTTGGTGGCGGTGGCCATGGTGTACTACTCGGACAGTTTG
GCAATGCACATTGGATCGGCTCTCTTGTTGGGATTGTTCTGGCAGCAGTG
TGGATGGCTTGCGCACGACTTTCTTCACCACCAAGTCTTTAAGCAACGAA
AGTACGGAGATCTCGTTGGCATCTTTTGGGGAGATCTCATGCAGGGGTTC
TCGATGCAGTGGTGGAAGAACAAGCACAATGGCCACCATGCTGTTCCCAA
CTTGCACAACTCTTCCTTGGACAGTCAGGATGGTGATCCCGATATTGATA
CCATGCCACTCCTTGCTTGGAGTCTCAAGCAGGCTCAGAGTTTCAGAGAG
ATCAATAAGGGAAAGGACAGTACCTTCGTCAAGTACGCTATCAAATTCCA
GGCATTCACATACTTCCCCATCCTCCTCTTGGCTCGCATCTCTTGGTTGA
ATGAATCCTTCAAAACTGCATTCGGACTCGGAGCTGCCTCGGAGAATGCC
AAGTTGGAGTTGGAGAAGCGTGGACTTCAGTACCCACTTTTGGAGAAGCT
TGGAATCACCCTTCATTACACTTGGATGTTCGTCCTCTCTTCCGGATTTG
GAAGGTGGTCTCTTCCATATTCCATCATGTATTTCTTCACTGCCACATGC
TCCTCGGGACTTTTCCTCGCATTGGTCTTTGGATTGGGACACAACGGTAT
GTCAGTGTACGATGCCACCACCCGACCTGACTTCTGGCAACTCCAAGTCA
CCACTACACGTAACATCATTGGTGGACACGGCATTCCCCAATTCTTTGTG
GATTGGTTCTGCGGTGGATTGCAATACCAAGTGGATCACCACCTCTTCCC
CATGATGCCTAGAAACAATATCGCGAAATGCCACAAGCTTGTGGAGTCAT
TCTGTAAGGAGTGGGGTGTGAAGTACCATGAGGCCGATATGTGGGATGGT
ACCGTGGAAGTGTTGCAACATCTCTCCAAGGTGTCGGATGATTTCCTTGT
GGAGATGGTGAAGGATTTCCCTGCCATG<u>TAA</u>ACACCTATTACCAGTCGGC
AGCTTTGTCGGTTGCTGGAGATGAATGATGCGAACTCATCGTAAATACTC
ATTATTAATGAACAATGTTACCCTGCAGTCGTGAGGTTTGCCTTCGTTGT
CCCACCCCTTCTATTGTGTATTGGTGATCATTGAAACGAGATAGTCTATT
TCTACATCAGATCTCTCCATTCACCCTCGAATAGTATCCCAACAACCATC
ACATCAAACTACTTGAATCTCCTCTGTGGCAATCCCTCCCATTGTACATT
TACTCTCAAAGGTATATCTATTTGTCCCTTTATTAATTGTTGAATATTGA
AGGGGAAGATTCCATTTTCCCCTCTCTCTTCCCCGATGATCCTCTCACCT
CTAAATACCTTTCACAACACAACAACGAAACAACGCAGATCAGACAAACA
ACATGGCAGAACTATCCTCACCGTGCAAACGATCCAAAGGCGAAGAGCTA
TTCCTAGTCCATCTCCAACGCATGTCTGGCTCCAGACCCTCATCCTGAAG
AGTGAGTTGTGATGTCGCTGATGTACTTTCCGTCTTGATGTTCTCTGAGG
TGTCACAACTCAGGGTCACCAAAGCAGCTTCGCTGATCGCTAGTGGCGAG
AAGATCCGATTTCCCATCCCGAAGAAGCCTCCTGGGAAAAATGTCACTT
CTTGAAAGTCGAGGGTGACGAATAATTGGGGCGGANGN
```

Figure 8b

```
ATGGCTGGAAAAGGAGGAGACGCAGCCGCAGCTACCAAGCGTAGTGGAGCATTGAAATTG
GCGGAGAAGCCGCAGAAGTACACTTGGCAGGAGGTGAAGAAGCACATCACCCCCGACGAT
GCCTGGGTAGTCCACCAAAACAAAGTCTACGACGTCTCCAACTGGTACGACCACCCCGGT
GGAGCCGTGGTGTTCACCCACGCCGGAGACGACATGACGGACATCTTCGCCGCCTTCCAC
GCCCAAGGCTCTCAGGCCATGATGAAGAAGTTTTACATTGGAGATTTGATTCCGGAGAGT
GTGGAGCATAAGGATCAAAGACAGTTGGATTTCGAGAAGGGATATCGTGATTTACGGGCC
AAGCTTGTCATGATGGGGATGTTCAAGTCGAGTAAGATGTATTATGCATACAAGTGCTCG
TTCAATATGTGCATGTGGTTGGTGGCGGTGGCCATGGTGTACTACTCGGACAGTTTGGCA
ATGCACATTGGATCGGCTCTCTTGTTGGGATTGTTCTGGCAGCAGTGTGGATGGCTTGCG
CACGACTTTCTTCACCACCAAGTCTTTAAGCAACGAAAGTACGGAGATCTCGTTGGCATC
TTTTGGGGAGATCTCATGCAGGGGTTCTCGATGCAGTGGTGGAAGAACAAGCACAATGGC
CACCATGCTGTTCCCAACTTGCACAACTCTTCCTTGGACAGTCAGGATGGTGATCCCGAT
ATTGATACCATGCCACTCCTTGCTTGGAGTCTCAAGCAGGCTCAGAGTTTCAGAGAGATC
AATAAGGGAAAGGACAGTACCTTCGTCAAGTACGCTATCAAATTCCAGGCATTCACATAC
TTCCCCATCCTCCTCTTGGCTCGCATCTCTTGGTTGAATGAATCCTTCAAAACTGCATTC
GGACTCGGAGCTGCCTCGGAGAATGCCAAGTTGGAGTTGGAGAAGCGTGGACTTCAGTAC
CCACTTTTGGAGAAGCTTGGAATCACCCTTCACTACACTTGGATGTTCGTCCTCTCTTCC
GGATTTGGAAGGTGGTCTCTTCCATATTCCATCATGTATTTCTTCACTGCCACATGCTCC
TCGGGACTTTTCCTCGCATTGGTCTTTGGATTGGGACACAACGGTATGTCAGTGTACGAT
GCCACCACCCGACCTGACTTCTGGCAACTCCAAGTCACCACTACACGTAACATCATTGGT
GGACACGGCATTCCCCAATTCTTTGTGGATTGGTTCTGCGGTGGATTGCAATACCAAGTG
GATCACCACCTCTTCCCCATGATGCCTAGAAACAATATCGCGAAGTGCCACAAGCTTGTG
GAGTCATTCTGTAAGGAGTGGGGTGTGAAGTACCATGAGGCTGATATGTGGGATGGTACC
GTGGAAGTGTTGCAACATCTCTCCAAGGTGTCGGATGATTTCCTTGTGGAGATGGTGAAG
GATTTCCCTGCCATGTAA
```

Figure 8c

```
MAGKGGDAAA ATKRSGALKL AEKPQKYTWQ EVKKHITPDD AWVVHQNKVY DVSNWYDHPG
GAVVFTHAGD DMTDIFAAFH AQGSQAMMKK FYIGDLIPES VEHKDQRQLD FEKGYRDLRA
KLVMMGMFKS SKMYYAYKCS FNMCMWLVAV AMVYYSDSLA MHIGSALLLG LFWQQCGWLA
HDFLHHQVFK QRKYGDLVGI FWGDLMQGFS MQWWKNKHNG HHAVPNLHNS SLDSQDGDPD
IDTMPLLAWS LKQAQSFREI NKGKDSTFVK YAIKFQAFTY FPILLLARIS WLNESFKTAF
GLGAASENAK LELEKRGLQY PLLEKLGITL HYTWMFVLSS GFGRWSLPYS IMYFFTATCS
SGLFLALVFG LGHNGMSVYD ATTRPDFWQL QVTTTRNIIG GHGIPQFFVD WFCGGLQYQV
DHHLFPMMPR NNIAKCHKLV ESFCKEWGVK YHEADMWDGT VEVLQHLSKV SDDFLVEMVK
DFPAM
```

Figure 9a

```
TATGTCCACCCCCCCCTGGTTTGTCCACCTCTGTCTTCGATCTTGGGACC
CGGGTCTCGAGTTTGCGAGACCTCTCAAGCGGGCCCATAGTAGACGACTT
GATCTGTTTGCTGATACCTGACGTGCACCGATTTTTCGGGGCTAACGCCA
CTTTTCGTAACTCCACCAGGTACGACTGACTTGTGCCCGTAGATATCTCT
GATACCTCTATGGCAAAGCCGATCAAATCGAAATGATTGTACTGTAGCAA
GGATAAGCAGATGGATAGGCGGGGATCTTCATGTCGACAAGAGGAAGAG
AGAGAGTATGTCGTCGGCGAGGGTGGATAGGTTGAGAGAGAGGGGATGAC
AGATTGTACATTATCTTCCCTCCAAGACTTTACCAAGGCACGTCACTCTG
ATTAGAATCTTACATACACGTGGAGTAATAGTGGACAATAAATGACAAGT
GAAGCACCCCAGTGGACCATTTCGTCGCCACGTGGTCGTCCGCTGTGGGT
TGAGTGAACCGACGACGACGAACACAACCGCTGAATCTCCTTCGGCAACA
ACAATACACCAATATGTGCAACGGCAACCTCCCAGCATCCACCGCACAGC
TCAAGTCCACCTCGAAGCCCCAGCAGCAACATGAGCATCGCACCATCTCC
AAGTCCGAGCTCGCCCAACACAACACGCCCAAATCAGCATGGTGTGCCGT
CCACTCCACTCCCGCCACCGACCCATCCCACTCCAACAACAAACAACACG
CACACCTAGTCCTCGACATTACCGACTTTGCGTCCCGCCATCCAGGGGGA
GACCTCATCCTCCTCGCTTCCGGCAAAGACGCCTCGGTGCTGTTTGAAAC
ATACCATCCACGTGGAGTTCCGACGTCTCTCATTCAAAAGCTGCAGATTG
GAGTGATGGAGGAGGAGGCGTTTCGGGATTCGTTTTACAGTTGGACTGAT
TCTGACTTTTATACTGTGTTGAAGAGGAGGGTTGTGGAGCGGTTGGAGGA
GAGGGGGTTGGCGAGGAGGGGATCGAAAGAGATTTGGATCAAGGCTTTGT
TCTTGTTGGTTGGATTTTGGTACTGTTTGTACAAGATGTATACTACGTCG
GATATTGATCAGTACGGTATTGCCATTGCCTATTCTATTGGAATGGGAAC
CTTTGCGGCATTCATCGGCACGTGTATTCAACACGATGGAAATCACGGTG
CATTCGCTCAGAACAAGTTACTCAACAAGTTGGCTGGGTGGACGTTGGAT
ATGATTGGTGCGAGTGCGTTTACGTGGGAGCTTCAGCACATGCTGGGCA
TCATCCATATACGAATGTGTTGGATGGGGTGGAGGAGGAGAGGAAGGAGA
GGGGGGAGGATGTTGCTTTGGAAGAAAAGGATCAGGTGAGACGAGATGAC
AGAGAGAGAGAGAGTCTATTCGTGTGAAGTCGTAGATGCATGTGTGCGAT
TGAGCGACACAACTCTAACGCATTGCATTCCACTTTCAACTCGCCGACAG
GAATCAGATCCAGACGTATTCTCCTCCTTCCCTCTCATGAGAATGCATCC
CCTCCATACAACCTCATGGTATCATAAATACCAACACCTCTACGCTCCAC
CCCTCTTTGCATTGATGACACTTGCCAAAGTATTCCAACAGGATTTTGAA
GTTGCCACATCCGGACGATTATATCATATTGATGCCAATGTACGTTATGG
TTCGGTATGGAATGTCATGAGGTTTTGGGCTATGAAGGTCATTACGATGG
GATATATGATGGGATTACCAATCTACTTTCATGGAGTACTGAGGGGAGTT
GGATTGTTTGTTATTGGGCATTTGGCGTGTGGAGAGTTGTTGGCGACGAT
GTTTATTGTGAATCACGTCATTGAGGGTGTGAGTTATGGAACGAAGGATT
TGGTTGGTGGTGCGAGTCATGTAGATGAGAAGAAGATTGTCAAGCCAACG
ACTGTATTGGGAGATACACCAATGGAAAAGACTCGCGAGGAGGCATTGAA
AAGCAACAGCAATAACAACAAGAAGAAGGGAGAGAAGAACTCGGTACCAT
CCGTTCCATTCAACGACTGGGCAGCAGTCCAATGCCAGACCTCCGTGAAT
TGGTCTCCAGGCTCATGGTTCTGGAATCACTTTTCTGGGGACTCTCTCA
TCAGATTGAGCATCACTTGTTCCCCAGCATTTGTCATACAAACTACTGTC
ATATCCAGGATGTTGTGGAGAGTACGTGTGCTGAGTACGGAGTTCCGTAT
CAGAGTGAGAGTAATTTGTTTGTTGCTTATGGAAAGATGATTAGTCATTT
GAAGTTTTTGGGTAAAGCCAAGTGTGAGTAGGTGTTAGGTATTGAGAGGT
GTCGAGTTGTCTCATTCTTTAAAAATAAGCGCTGAAAGTGATTTCGAAAA
ACAAGGTTTGTCAATACCAGTCTCTTGTATTGATTGCTGCGTCGACACAT
CTCCGTGAGGAGTTTGACCTCACTCATTCTAACTTGGAATGTCTCTTTTG
CGCTGGTGAGCTTGGACGAATACACTCCGNCAGAAGAGACTGCATTGGTA
ATGCAGAGGAAAGAGGATATACTGTATGAGTCCGAAGAATCGATGACGCG
CGGTGAGGTGGTGTACATCACTTGTGAGGACCAACGTGGAACCGCATGTC
TGAAGAGGTCCATACCTAAACATTTGAGCGGTCTTGGGAGCAAACTTTAG
CAGAGATTGAATGCTCCATTCGGTATTTGTTCTTCTGTGCCANTTTGATA
AGGAACAGCAACCAACACACCGGGG
```

Figure 9b

MCNGNLPAST AQLKSTSKPQ QQHEHRTISK SELAQHNTPK SAWCAVHSTP ATDPSHSNNK
QHAHLVLDIT DFASRHPGGD LILLASGKDA SVLFETYHPR GVPTSLIQKL QIGVMEEEAF
RDSFYSWTDS DFYTVLKRRV VERLEERGLA RRGSKEIWIK ALFLLVGFWY CLYKMYTTSD
IDQYGIAIAY SIGMGTFAAF IGTCIQHDGN HGAFAQNKLL NKLAGWTLDM IGASAFTWEL
QHMLGHHPYT NVLDGVEEER KERGEDVALE EKDQVRRDDR ERESLFV QESD PDVFSSFPLM
RMHPLHTTSWYHKYQHLYAP PLFALMTLAK VFQQDFEVAT SGRLYHIDAN VRYGSVWNVM
RFWAMKVITMGYMMGLPIYF HGVLRGVGLF VIGHLACGEL LATMFIVNHV IEGVSYGTKD
LVGGASHVDEKKIVKPTTVL GDTPMEKTRE EALKSNSNNN KKKGEKNSVP SVPFNDWAAV
QCQTSVNWSPGSWFWNHFSG GLSHQIEHHL FPSICHTNYC HIQDVVESTC AEYGVPYQSE
SNLFVAYGKMISHLKFLGKA KCE

Figure 10a

ATGGACTTTCTCTCCGGCGATCCT
TTCCGGACACTCGTCCTTGCAGCACTTGTTGTCATCGGATTTGCTGCGGC
GTGGCAATGCTTCTACCCGCCGAGCATCGTCGGCAAGCCTCGTACATTAA
GCAATGGTAAACTCAATACCAGAATCCATGGCAAATTGTACGACCTCTCA
TCGTTTCAGCATCCAGGAGGCCCCGTGGCTCTTTCTCTTGTTCAAGGTCG
CGACGGAACAGCTCTATTTGAGTCACACCATCCCTTCATACCTCGAAAGA
ATCTACTTCAGATCCTCTCCAAGTACGAGGTTCCGTCGACTGAAGACTCT
GTTTCCTTCATCGCCACCCTAGACGAACTCAATGGTGAATCTCCGTACGA
TTGGAAGGACATTGAAATGATGATTTCGTATCTGACCTACGAGCTCTCG
TAATTGAGCACTTTTCTCCTCTCGCCAAGGAAAGGGGAGTTTCACTCGTT
GAGTCGTCGAAGGCAACACCTCAGCGGTGGATGGTGGTTCTACTGCTCCT
TGCGTCGTTCTTCCTCAGCATCCCATTATATTTGAGTGGTTCGTGGACTT
TCGTTGTCGTCACTCCCATCCTCGCTTGGCTGGCGGTTGTCAATTACTGG
CACGATGCTACTCACTTTGCATTGAGCAGCAACTGGATTTTGAATGCTGC
GCTCCCATATCTCCTCCCTCTCCTATCGAGTCCGTCAATGTGGTATCATC
ATCACGTCATTGGACATCACGCATACACCAACATTTCCAAAAGAGATCCA
GATCTTGCTCACGCTCCACAACTCATGAGAGAACACAAGAGTATCAAATG
GAGACCATCTCACTTAAATCAAACACAGCTTCCGCGGATTCTCTTCATCT
GGTCGATTGCAGTCGGTATTGGGTTGAACTTACTGAACGACGTGAGAGCA
CTAACCAAGCTTTCATACAACAACGTTGTTCGGGTGGAGAAGATGTCATC
GTCGCGAACATTACTCCATTTCCTTGGACGTATGTTGCACATCTTTGTGA
CTACACTTTGGCCCTTTTTGGCGTTTCCGGTGTGGAAGGCCATCGTTTGG
GCGACTGTACCGAATGCCATACTGAGTTTGTGCTTCATGCTGAATACGCA
AATCAATCACCTCATCAACACGTGTGCACATGCTTCCGATAACAACTTTT
ACAAGCATCAAGTTGTAACTGCTCAGAACTTTGGCCGATCAAGTGCCTTT
TGCTTCATCTTCTCGGGAGGTCTCAACTACCAAATTGAACATCATTTGTT
GCCGACGGTGAACCATTGCCATTTGCCAGCTTTGGCCCCGGGTGTAGAGC
GTTTGTGTAAGAAACACGGGGTGACATACAACTCTGTTGAAGGATACAGA
GAGGCCATCATTGCACACTTTGCACATACCAAAGATATGTCGACGAAGCC
TACTGATTGA

Figure 11a

```
ANNTCTCCCACCCNGCCAGCTCTTTCAGGTCGACCGGAGATACACACTTC
TTCCCACCAACTTCGTCCTCCATACGATCGGAAGAAAAGAGGAGATTATC
TTGACTTCTTGACGGAGGAGTGGGATGAAAAGAACTTGAGTGGGTAAGGG
CTGATTTTCCTGAGAAGGAGAAGTCAGCTGGAACGAAGTTCATGGAGTTT
TGTGGCAACCCTATTGAGACGTTGCTTGGTGGAGGAAGGTAGCGAGGTTG
AGCATGCAAACAGAATGGTATAAATCACTAAGATGTCACTCCCAATGACA
AGTAGGAATAGCAATGACGAGATGGTGTACAGATGTTAGAGATGGAGAGA
TTAAGCGAATGGCTGGATGATTAGGATATGCAATGCAAAACTGTATAGAT
TCTTGCTAATAGACTTTGTAGACAACGTCCGTCTGCAGAAAAGGACAATA
CTAATTAATATAAAACCGACTCGGAGAGAACATGACATGGCAAGTTGTCA
CTATGGAATTCACTACGTCGCTTGACAGGAAGCTCACGTGGCCTCGGCGA
AGAAGACAAACAAAACCGAGCCCTCACATTTCACTCTGTACAGTTCATAG
TCAACACCACCAATACGATGCCCCCAACGCCGATATCTCCCGCATCCGC
AACCGCATCCCCACCAAAACAGGTACCGTTGCCTCTGCCGACAACAACGA
CCCCGCCACCCAATCCGTCCGAACCCTCAAATCTCTCAAGGGCAACGAGG
TCGTCATCAACGGCACAATTTATGACATTGCTGACTTTGTCCATCCTGGA
GGAGAGGTTGTCAAGTTCTTTGGTGGGAATGATGTTACTATTCAGTATAA
TATGATTCATCCGTATCATACGGGGAAACATCTGGAGAAGATGAAGGCTG
TTGGAAAGGTTGTAGATTGGCAGTCGGAGTGAGTTTGAATGGTGCACACG
TTGACGTTGTTGTTGTGTCATTTCGTTCTTTGCATTTGATATCCAACTGA
CCTCTACACACCTCTTCGTTACCATAGCTACAAGTTCGACACCCCCTTTG
AACGAGAGATCAAATCAGAAGTGTTCAAGATCGTACGTCGCGGGCGTGAG
TTCGGCACAACAGGCTACTTCCTCCGTGCCTTTTTCTACATCGCTCTCTT
CTTCACCATGCAATACACTTTCGCCACATGCACCACCTTCACCACCTACG
ATCACTGGTATCAGAGTGGTGTATTCATCGCAATTGTGTTTGGTATTTCA
CAGGCATTCATTGGGTTGAATGTCCAGCACGATGCCAATCACGGAGCTGC
CAGTAAGCGTCCCTGGGTGAATGACTTGTTGGGATTTGGAACGGATTTGA
TTGGATCTAACAAATGGAATTGGATGGCACAGCATTGGACTCATCACGCT
TACACTAACCATAGTGAGAAGGATCCCGATAGCTTCAGCTCGGAACCTAT
GTTTGCATTCAATGACTATCCCATTGGACACCCGAAGAGAAAGTGGTGGC
ATAGGTTCCAGGGAGGGTACTTCCTCTTCATGCTTGGACTTTACTGGCTC
TCGACTGTATTCAATCCGCAATTCATTGATCTTCGTCAACGTGGGCTCA
GTACGTCGGAATTCAAATGGAGAATGATTTCATTGTCAAGAGGAGGAAGT
ACGCCGTTGCATTGAGGATGATGTACATTTACTTGAACATTGTCAGCCCC
TTCATGAACAATGGTTTGAGCTGGTCTACCTTTGGAATCATCATGTTGAT
GGGAATCAGCGAGAGTCTCACTCTCAGTGTGCTCTTCTCGTTGTCTCACA
ACTTCATCAATTCGGATCGTGATCCTACGGCTGACTTCAAAAAGACCGGA
GAACAAGTGTGCTGGTTCAAGTCGCAGGTGGAGACTTCGTCTACCTATGG
GGGTTTTATTTCCGGATGTCTTACGGGAGGACTCAACTTTCAGGTGGAAC
ATCATCTCTTTCCCCGTATGAGCAGTGCTTGGTATCCTTACATTGCACCT
ACGGTTCGTGAGGTTTGCAAGAAGCACGGGGTGAACTACGCTTATTATCC
TTGGATTGGGCAGAATTTGGTATCAACATTCAAATACATGCATCGCGCTG
GTAGTGGAGCCAACTGGGAGCTCAAGCCGTTGTCTGGAAGTGCCTAAAGT
TTAGTTGTACTGATTGTCGGAGGTGCTGCTGGTGCTTCAACTAATGTTAG
GAGTGCATGTTAAAAGCCTTCTTTGTGTTTTGTTGTCTTCGTATTCAGTA
TATCAGTTTCGATATGTTGCATTGTAACCTCCTCCACTTGCACTCAAAAC
AAATCTAGCATAACATTTCTCATCCCGAGTCATGTCATGAACGACTCATT
ACGCAATGCCTCTCTCATAACCCCGAAACAACTCGACCAGCTTCATACTC
TAATCGTCCATCTTTGGCAGCTGCAATCCAGCCCTAGCAGCAGCTCTCTT
ACTCAACTCCATCGGACTCAACTTCGTATCTGCCCCGCATCAATCTCAT
GCAACCGTGCCCTCTCTACCAAATCTGCCTTTAACATCCAGTAATCATAG
GCGATTCCACGTAGTACGTTTGCTCGCTCGGGAGACACTGATGCCGATGC
TTTGTATTGTGATATACTGTGCTGGTGCGCGCATCGATGCTCCGNTGTGN
GTTGNGACTGTGCATTGGATGCTGCTGTGAAACAGTCGGTGCAGTGTAGC
GGAGGTGCTGTTTCTGAACTGAGGAGATGCCCGCAAACTGATAGGGGGTG
GTGCAGCGCTATAAATTTTGCGAGCGAGTCCATTGTCCTTGCTCTCCCCA
TATGTCGGGCGAGGGCGAAGCGCGAAGGAGAAGCCACAAGGCCAATACAA
CAGAAAGTTTAAATGAAGGACGTAATTCCTACACAGTCCAGTGGCGAAGT
TACAAC
```

Figure 11b

```
ATGGCTCCCCCCAACGCCGATATCTCCCGCATCCGCAACCGCATCCCCACCAAAACAGGT
ACCGTTGCCTCTGCCGACAACAACGACCCCGCCACCCAATCCGTCCGAACCCTCAAATCT
CTCAAGGGCAACGAGGTCGTCATCAACGGCACAATTTATGACATTGCTGACTTTGTCCAT
CCTGGAGGAGAGGTTGTCAAGTTCTTTGGTGGGAATGATGTTACTATTCAGTATAATATG
ATTCATCCGTATCATACGGGGAAACATCTGGAGAAGATGAAGGCTGTTGGAAAGGTTGTA
GATTGGCAGTCGGACTACAAGTTCGACACCCCCTTTGAACGAGAGATCAAATCAGAAGTG
TTCAAGATCGTACGTCGCGGGCGTGAGTTCGGCACAACAGGCTACTTCCTCCGTGCCTTT
TTCTACATCGCTCTCTTCTTCACCATGCAATACACTTTCGCCACATGCACCACCTTCACC
ACCTACGATCACTGGTATCAGAGTGGTGTATTCATCGCAATTGTGTTTGGTATTTCACAG
GCATTCATTGGGTTGAATGTCCAGCACGATGCCAATCACGGAGCTGCCAGTAAGCGTCCC
TGGGTGAATGACTTGTTGGATTTGGAACGGATTTGATTGGATCTAACAAATGGAATTGG
ATGGCACAGCATTGGACTCATCACGCTTACACTAACCATAGTGAGAAGGATCCCGATAGC
TTCAGCTCGGAACCTATGTTTGCATTCAATGACTATCCCATTGGACACCCGAAGAGAAAG
TGGTGGCATAGGTTCCAGGGAGGGTACTTCCTCTTCATGCTTGGACTTTACTGGCTCCCG
ACTGTATTCAATCCGCAATTCATTGATCTTCGTCAACGTGGGGCTCAGTACGTCGGAATT
CAAATGGAGAATGATTTCATTGTCAAGAGGAGGAAGTACGCCGTTGCATTGAGGATGATG
TACATTTACTTGAACATTGTCAGCCCCTTCATGAACAATGGTTTGAGCTGGTCTACCTTT
GGAATCATCATGTTGATGGGAATCAGCGAGAGTCTCACTCTCAGTGTGCTCTTCTCGTTG
TCTCACAACTTCATCAATTCGGATCGTGATCCTACGGCTGACTTCAAAAAGACCGGAGAA
CAAGTGTGCTGGTTCAAGTCGCAGGTGGAGACTTCGTCTACCTATGGGGGTTTTATTTCC
GGATGTCTTACGGGAGGACTCAACTTTCAGGTGGAACATCATCTCTTTCCCCGTATGAGC
AGTGCTTGGTATCCTTACATTGCACCTACGGTTCGTGAGGTTTGCAAGAAGCACGGGATG
AGCTACGCTTATTATCCTTGGATTGGGCAGAATTTGGTATCAACATTCAAATACATGCAT
CGCGCTGGTAGTGGAGCCAACTGGGAGCTCAAGCCGTTGTCTGGAAGTGCCTAA
```

Figure 11c

```
MAPPNADISR IRNRIPTKTG TVASADNNDP ATQSVRTLKS LKGNEVVING TIYDIADFVH
PGGEVVKFFG GNDVTIQYNM IHPYHTGKHL EKMKAVGKVV DWQSDYKFDT PFEREIKSEV
FKIVRRGREF GTTGYFLRAF FYIALFFTMQ YTFATCTTFT TYDHWYQSGV FIAIVFGISQ
AFIGLNVQHD ANHGAASKRP WVNDLLGFGT DLIGSNKWNW MAQHWTHHAY TNHSEKDPDS
FSSEPMFAFN DYPIGHPKRK WWHRFQGGYF LFMLGLYWLP TVFNPQFIDL RQRGAQYVGI
QMENDFIVKR RKYAVALRMM YIYLNIVSPF MNNGLSWSTF GIIMLMGISE SLTLSVLFSL
SHNFINSDRD PTADFKKTGE QVCWFKSQVE TSSTYGGFIS GCLTGGLNFQ VEHHLFPRMS
SAWYPYIAPT VREVCKKHGM SYAYYPWIGQ NLVSTFKYMH RAGSGANWEL KPLSGSA
```

Figure 11d

```
ATGGCTCCCCCCAACGCCGATATCTCCCGCATCCGCAACCGCATCCCCACCAAAACAGGT
ACCTCTGCCGACAACAACGACCCCGCCACCCAATCCGTCCGAACCCTCAAATCTCTCAAG
GGCAACGAGGTCGTCATCAACGGCACAATTTATGACATTGCTGACTTTGTCCATCCTGGA
GGAGAGGTTGTCAAGTTCTTTGGTGGGAATGATGTTACTATTCAGTATAATATGATTCAT
CCGTATCATACGGGGAAACATCTGGAGAAGATGAAGGCTGTTGGAAAGGTTGTAGATTGG
CAGTCGGACTACAAGTTCGACACCCCCTTTGAACGAGAGATCAAATCAGAAGTGTTCAAG
ATCGTACGTCGCGGGCGTGAGTTCGGCACAACAGGCTACTTCCTCCGTGCCTTTTTCTAC
ATCGCTCTCTTCTTCACCATGCAATACACTTTCGCCACATGCACCACCTTCACCACCTAC
GATCACTGGTATCAGAGTGGTGTATTCATCGCAATTGTGTTTGGTATTTCACAGGCATTC
ATTGGGTTGAATGTCCAGCACGATGCCAATCACGGAGCTGCCAGTAAGCGTCCCTGGGTG
AATGACTTGTTGGGATTTGGAACGGATTTGATTGGATCTAACAAATGGAATTGGATGGCA
CAGCATTGGACTCATCACGCTTACACTAACCATAGTGAGAAGGATCCCGATAGCTTCAG
CTCGGAACCTATGTTTGCATTCAATGACTATCCCATTGGACACCCGAAGAGAAAGTGGT
GGCATAGGTTCCAGGGAGGGTACTTCCTCTTCATGCTTGGACTTTACTGGCTCTCGACTG
TATTCAATCCGCAATTCATTGATCTTCGTCAACGTGGGGCTCAGTACGTCGGAATTCAAA
TGGAGAATGATTTCATTGTCAAGAGGAGGAAGTACGCCGTTGCATTGAGGATGATGTACA
TTTACTTGAACATTGTCAGCCCCTTCATGAACAATGGTTTGAGCTGGTCTACCTTTGGAA
TCATCATGTTGATGGGAATCAGCGAGAGTCTCACTCTCAGTGTGCTCTTCTCGTTGTCTC
ACAACCTCATCAATTCGGATCGTGATCCTACGGCTGACTTCAAAAAGACCGGAGAACAAG
TGTGCTGGTTCAAGTCGCAGGTGGAGACTTCGTCTACCTATGGGGGTTTTATTTCCGGAT
GTCTTACGGGAGGACTCAACTTTCAGGTGGAACATCATCTCTTTCCCCGTATGAGCAGTG
CTTGGTATCCTTACATTGCACCTACGGTTCGTGAGGTTTGCAAGAAGCACGGGGTGAACT
ACGCTTATTATCCTTGGATTGGGCAGAATTTGGTATCAACATTCAAATACATGCATCGCG
CTGGTAGTGGAGCCAACTGGGAGCTCAAGCCGTTGTCTGGAAGTGCCTAA
```

Figure 11e

```
MAPPNADISR IRNRIPTKTG TSADNNDPAT QSVRTLKSLK GNEVVINGTI YDIADFVHPG
GEVVKFFGGN DVTIQYNMIH PYHTGKHLEK MKAVGKVVDW QSDYKFDTPF EREIKSEVFK
IVRRGREFGT TGYFLRAFFY IALFFTMQYT FATCTTFTTY DHWYQSGVFI AIVFGISQAF
IGLNVQHDAN HGAASKRPWV NDLLGFGTDL IGSNKWNWMA QHWTHHAYTN HSEKDPDSFS
SEPMFAFNDY PIGHPKRKWW HRFQGGYFLF MLGLYWLSTV FNPQFIDLRQ RGAQYVGIQM
ENDFIVKRRK YAVALRMMYI YLNIVSPFMN NGLSWSTFGI IMLMGISESL TLSVLFSLSH
NLINSDRDPT ADFKKTGEQV CWFKSQVETS STYGGFISGC LTGGLNFQVE HHLFPRMSSA
WYPYIAPTVR EVCKKHGVNY AYYPWIGQNL VSTFKYMHRA GSGANWELKP LSGSA
```

DESATURASE ENZYMES

FIELD OF THE INVENTION

The invention relates to transgenic cells transformed with nucleic acid molecules which encode enzymes with desaturase activity and the use of these cells and enzymes in biocatalysis.

BACKGROUND OF THE INVENTION

Desaturases are enzymes involved in the synthesis of long chain polyunsaturated fatty acids (PUFAs). PUFAs are fatty acids (FAs) which are essential to the normal functioning of a cell and their nutritional properties are well known. An example of a PUFA is docosahexaenoic acid (DHA). DHA is a n-3 fatty acid that can be obtained directly from the diet or derived from metabolism of dietary linoleic and α-linolenic acid. The n-3 fatty acids are associated with health promoting properties. For example n-3 fatty acids have been described as anti-inflammatory, antithrombotic, antiarrhythmic, hypolipidemic and vasodilatory. As such, the role of DHA in the prevention and/or treatment of diseases such as coronary heart disease, hypertension, type II diabetes, ocular diseases, arthritis, cystic fibrosis and schizophrenia has been the focus of a great deal of medical research.

The production of PUFAs involves a consecutive series of desaturations and elongations of the fatty acyl chain to generate arachidonic acid (20:4Δ5,8,11,14) and docosahexaenoic acid (22:6Δ4,7,10,13,16,19). Several desaturases involved in this metabolic process have been isolated from marine microalgae, including *Phaeodactylum tricornutum* [5], *Euglena gracilis* [6] and *Pavlova lutheri* [7]. These membrane-bound desaturases are specific with respect to both chain length of the substrate and the double bond positions on the fatty acid. They belong to the class known as front-end fatty acid desaturases due to the fact that they introduce double bonds between the carboxy-group and pre-existing bond(s) of the fatty acid [1]. These desaturases contain a cytochrome b5 domain at their N-terminus and three histidine motifs that are important for catalytic activity [10].

Desaturase enzymes and the genes which encode them are known in the art. For example, WO03/064596 describes, amongst other things, transgenic cells transformed with omega 3 and delta 12 desaturase nucleic acid molecules and the use of these cells in the production of fatty acids. In particular the use of the omega 3 desaturase in the conversion of arachidonic acid to eicosapentaenoic acid and the use of the delta 12 desaturase in the conversion of oleic acid to linoleic acid. WO03/099216 also describes fungal desaturases and in particular transgenic plants modified to express fungal delta 15 desaturase enzymes.

Furthermore, US2003/0157144 and US2003/0167525 disclose delta 5 and delta 6 desaturase genes in the conversion of dihomoylinolenic acid to arachidonic acid and linoleic acid to γ-linolenic acid respectively. Moreover, US2003/134400 discloses delta 4 desaturase genes which are involved in the conversion of adrenic acid to ω6-docosapentaenoic acid and in the conversion of ω3-docosapentaenoic acid to docosahexaenoic acid. These rare fatty acids are used in pharmaceutical and cosmetic compositions and can be essential nutritional fatty acids.

Besides the common FAs 16:0, 16:1Δ9, 18:0 and 18:1Δ9 found in most living organisms, trace amounts of more unusual fatty acids can be found in a wide range of species. For instance, presence of 16:1Δ11 has been reported in several species of *Pavlova*, in the Eustigmatophyte *Nannochloropsis oculata*, and in the diatoms *Phaeodactylum tricornutum* and *Thalassiosira pseudonana* [11,12,13]. This FA accounted for a very small portion of the total FAs in these microalgae, and its specific role in the algal cells is unknown. However, this FA is a very important precursor in the synthesis of sex pheromones in insects. Sex pheromones are species-specific blends of unsaturated fatty acid (UFA) derivatives that differ in terminal functional group and in the number, position and configuration (Z or E) of the double bond(s), which are produced by various acyl-CoA desaturases [14,15]. Simple monoene Δ11 UFAs are the most prevalent precursors in the formation of major sex pheromone components in the modern *Lepidoptera* [16,17]. For instance, in the corn earworm *Helicoverpa zea*, which produces a pheromone mixture of Z11-16:Ald and Z9-16:Ald in a 30:1 ratio, the most abundant desaturase-encoding transcript is HzeaLPAQ (also called HzPGDs1) which encodes a Δ11-desaturase that does not possess a cytochrome b5 extension, and therefore requires free cytochrome b5 for activity. Many acyl-CoA Δ11-desaturases with different specificities have been isolated from insects [14,15], but none from other species.

DESCRIPTION OF THE INVENTION

We describe the first characterisation of a cytochrome b5 desaturase exhibiting Δ11-desaturase activity.

According to an aspect of the invention there is provided a transgenic cell comprising a nucleic acid molecule which comprises a nucleic acid sequence which nucleic acid molecule consists of the sequences as represented in FIG. 5a, 5b, 6a, 6c, 7a, 8a, 8b, 9a, 10a, 11a, 11b, 11d or nucleic acid molecules which hybridise to these sequences, wherein said nucleic acid molecules encode a polypeptide which has desaturase activity.

In a preferred embodiment of the invention said hybridisation conditions are stringent hybridisation conditions.

In a preferred embodiment of the invention said nucleic acid molecule comprises a nucleic acid sequence which has at least 30% homology to the nucleic acid sequence represented in FIG. 5a, 5b, 6a, 6c, 7a, 8a, 8b, 9a, 10a, 11a, 11b, or 11d. Preferably said homology is at least 40%, 50%, 60%, 70%, 80%, 90%, or at least 99% identity with the nucleic acid sequence represented in FIG. 5a, 5b, 6a, 7a, 8a, 8b, 9a, 10a, 11a, or 11b and which encodes a polypeptide which has desaturase activity.

The sequence of desaturase nucleic acids may be modified to produce variant enzymes with enhanced expression in cells. For example, the addition of a codon that encodes an alanine amino acid may facilitate recombinant expression in microbial systems e.g. yeast. These modifications may not be required in all expression systems but is sometimes desirable.

In a preferred embodiment of the invention said nucleic acid molecule comprises the nucleic acid sequence as represented in FIG. 5a, 5b, 6a, 6c 7a, 8a, 8b, 9a, 10a, 11a, 11b, or 11d. Preferably said nucleic acid molecule consists of the nucleic acid sequence as represented in FIG. 5a, 5b, 6a, 7a, 8a, 8b, 9a, 10a, 11a, or 11b.

In a further preferred embodiment of the invention said cell over-expresses said desaturase encoded by said nucleic acid molecule.

In a preferred embodiment of the invention said over-expression is at least 2-fold higher when compared to a non-transformed reference cell of the same species.

Preferably said over-expression is: at least 3-fold, 4-fold, 5-fold, 6-fold, 7-fold, 8-fold, 9-fold, or at least 10-fold when compared to a non-transformed reference cell of the same species.

In a preferred embodiment of the invention said nucleic acid molecule is a cDNA.

In yet a further preferred embodiment of the invention said nucleic acid molecule is a genomic DNA.

In a preferred embodiment of the invention said transgenic cell is transfected with a nucleic acid molecule comprising a nucleic acid sequence as represented by FIG. 10a and which encodes a desaturase polypeptide wherein said polypeptide has Δ11-desaturase activity, or a nucleic acid molecule which hybridises to the nucleic acid molecule in FIG. 10a and encodes a polypeptide with Δ11-desaturase activity.

In an alternative preferred embodiment of the invention said transgenic cell is transfected with a nucleic acid molecule comprising a nucleic acid sequence as represented by FIG. 8a and which encodes a desaturase polypeptide wherein said polypeptide has Δ6-desaturase activity, or a nucleic acid molecule which hybridises to the nucleic acid molecule in FIG. 8a and encodes a polypeptide with Δ6-desaturase activity.

In a preferred embodiment of the invention said transgenic cell is a eukaryotic cell.

In an alternative preferred embodiment of the invention said cell is a prokaryotic cell.

In a further preferred embodiment of the invention said eukaryotic cell is a plant cell.

Plants which include a plant cell according to the invention are also provided as are seeds produced by said plants.

In a preferred embodiment of the invention said plant is selected from: corn (*Zea mays*), canola (*Brassica napus, Brassica rapa* ssp.), flax (*Linum usitatissimum*), alfalfa (*Medicago sativa*), rice (*Oryza sativa*), rye (*Secale cerale*), sorghum (*Sorghum bicolor, Sorghum vulgare*), sunflower (*Helianthus annus*), wheat (*Tritium aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Iopmoea batatus*), cassaya (*Manihot esculenta*), coffee (*Cofea* spp.), coconut (*Cocos nucifera*), pineapple (*Anana comosus*), citrus tree (*Citrus* spp.) cocoa (*Theobroma cacao*), tea (*Camellia senensis*), banana (*Musa* spp.), avacado (*Persea americana*), fig (*Ficus casica*), guava (*Psidium guajava*), mango (*Mangifer indica*), olive (*Olea europaea*), papaya (*Carica papaya*), cashew (*Anacardium occidentale*), macadamia (*Macadamia intergrifolia*), almond (*Prunus amygdalus*), sugar beets (*Beta vulgaris*), oats, barley, vegetables and ornamentals.

Preferably, plants of the present invention are crop plants (for example, cereals and pulses, maize, wheat, potatoes, tapioca, rice, sorghum, millet, cassaya, barley, pea), and other root, tuber or seed crops. Important seed crops are oil-seed rape, sugar beet, maize, sunflower, soybean, sorghum, and flax (linseed). Horticultural plants to which the present invention may be applied may include lettuce, endive, and vegetable brassicas including cabbage, broccoli, and cauliflower. The present invention may be applied in tobacco, cucurbits, carrot, strawberry, sunflower, tomato, or pepper.

Grain plants that provide seeds of interest include oil-seed plants and leguminous plants. Seeds of interest include grain seeds, such as corn, wheat, barley, rice, sorghum, rye, etc. Oil seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava been, lentils, chickpea, etc.

According to a further aspect of the invention there is provided a seed comprising a plant cell according to the invention. Preferably said seed is from an oil seed plant.

According to a yet further aspect of the invention there is provided a reaction vessel comprising at least one polypeptide according to the invention, fatty acid substrates and co-factors wherein said vessel is adapted for the desaturation of said fatty acids substrates.

In a preferred embodiment of the invention said polypeptide is expressed by a cell according to the invention.

Preferably said cell is a eukaryotic cell, for example a yeast cell.

In an alternative preferred embodiment of the invention said cell is a prokaryotic cell.

According to a further aspect of the invention there is provided a method to desaturate a fatty acid substrate comprising the steps of:
  i) providing a reaction vessel according to the invention; and
  ii) growing said cells contained in said reaction vessel under conditions which allow the desaturation of at least one fatty acid substrate.

An embodiment of the invention will now be described by example only and with reference to the following tables and figures:

Table 1 illustrates the composition of major fatty acids in *T. pseudonana*;

Table 2 illustrates the major fatty acids of pYES and pYDESN yeast transformants with and without addition of exogenous saturated fatty acids;

Table 3 illustrates the Δ6 desaturase activity of TpDESI compared to that of an homologous *Phaeodactylum tricornutum* desaturase;

FIG. 1 illustrates the predicted protein sequences with homology to front-end desaturases derived from the *T. pseudonana* draft genome. Sequence alignments of 12 putative *T. pseudonana* desaturases with other functionally characterised front-end desaturase enzymes identified three main blocks of homology that represent the functional domains of front-end acyl desaturases (A). The darker shaded box highlights the cytochrome b5 haem-binding domain and shaded boxes indicate three histidine boxes. See Material and Methods for Genbank accession number and source species of the functionally characterised enzymes. A phylogenetic tree of nine *T. pseudonana* desaturases with other enzymes was constructed (B). By removing the regions containing gaps (ambiguous alignment region), a dataset was created from an alignment originally made with clustalX. The tree was constructed from the dataset using Phylip3.5c software package and bootstrap analyses were carried out with 1000 replicates. Only well supported nodes (over 70%) are indicated with bootstrap values. All branches are drawn to scale as indicated by the scale bar (=0.1 substitutions/site). TpDESN sequence is 477 amino acids long (C). The cytochrome b5 haem-binding domain is on a shaded background and the three histidine-boxes are framed;

FIG. 2 illustrates RT-PCR expression analysis of TpdesN. Cells were harvested at different stages of growth for total RNA extraction and cDNA synthesis (A). PCR was performed on cDNA derived from reverse transcribed RNA using TpdesN and 18s rRNA specific primer pairs (B). PCR was carried out on undiluted (lane 1) and five-fold serial dilutions (lane 2-4) of each cDNA. The 18S rRNA gene was used as a control of cDNA synthesis. EE: early exponential phase, LE: late exponential phase, ES: early stationary phase;

FIG. 3 illustrates GC analysis of FAMEs (fatty acid methyl esters) from yeast transformed with the empty plasmid pYES2 or the plasmid containing TpDESN. Invsc1 yeast strain transformed with either pYES2 (A) or pYDESN (B) were induced for three days at 20° C. without supplementation before sampling for fatty acid analysis. I. S. internal standard (17:0). The experiment was repeated three times and results of a representative experiment are shown;

FIG. 4 illustrates mass spectra of DMDS FAME adducts from pYDESN transformed yeast. Mass spectrum of the DMDS adduct of 16:1Δ9 FAME, present in all yeast samples (A). Mass spectrum of the DMDS adduct of 16:1Δ11 FAME, which was only found in yeast transformed with pYDESN (B). Picolinyl esters with spectra characteristic of 16:1Δ11 were also identified in these samples (data not shown); and FIG. 5a is the genomic nucleic acid sequence of the desaturase A (SEQ ID NO: 2) from *T. pseudonana*; FIG. 5b is the cDNA sequence of desaturase A (SEQ ID NO: 3); FIG. 5c amino acid sequence (SEQ ID NO: 4);

FIG. 6a (SEQ ID NO: 5) is the genomic nucleic acid sequence of desaturase B from *Thalassiosira pseudonana*; FIG. 6b is the partial amino acid sequence (SEQ ID NO: 6); FIG. 6c is the cDNA sequence of desaturase B (SEQ ID NO: 20); and FIG. 6d is the amino acid sequence of said cDNA sequence (SEQ ID NO: 21);

FIG. 7a is the nucleic acid sequence of desaturase E from *Thalassiosira pseudonana* (SEQ ID NO: 7); FIG. 7b is the amino acid sequence (SEQ ID NO: 8);

FIG. 8a is the nucleic acid sequence of desaturase I from *Thalassiosira pseudonana* (SEQ ID NO: 9); FIG. 8b is the cDNA sequence (SEQ ID NO: 10); and FIG. 8c is the amino acid sequence (SEQ ID NO: 11);

FIG. 9a is the nucleic acid sequence of desaturase K from *Thalassiosira pseudonana* (SEQ ID NO: 12); FIG. 9b is the amino acid sequence (SEQ ID NO: 13);

FIG. 10a is the nucleic acid sequence of desaturase N from *Thalassiosira pseudonana* (SEQ ID NO: 14);

Figure 12A:
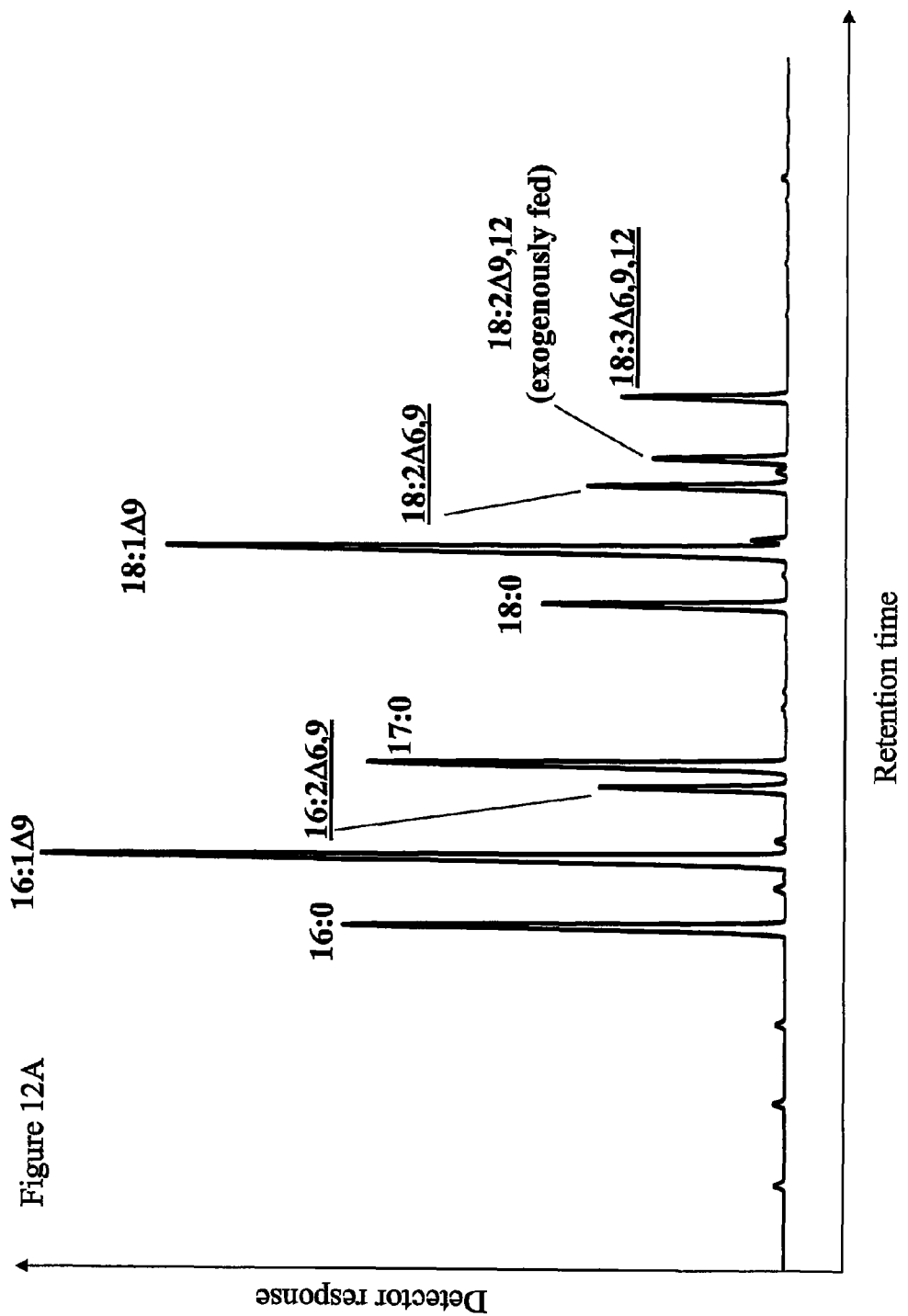
Figure 12B:
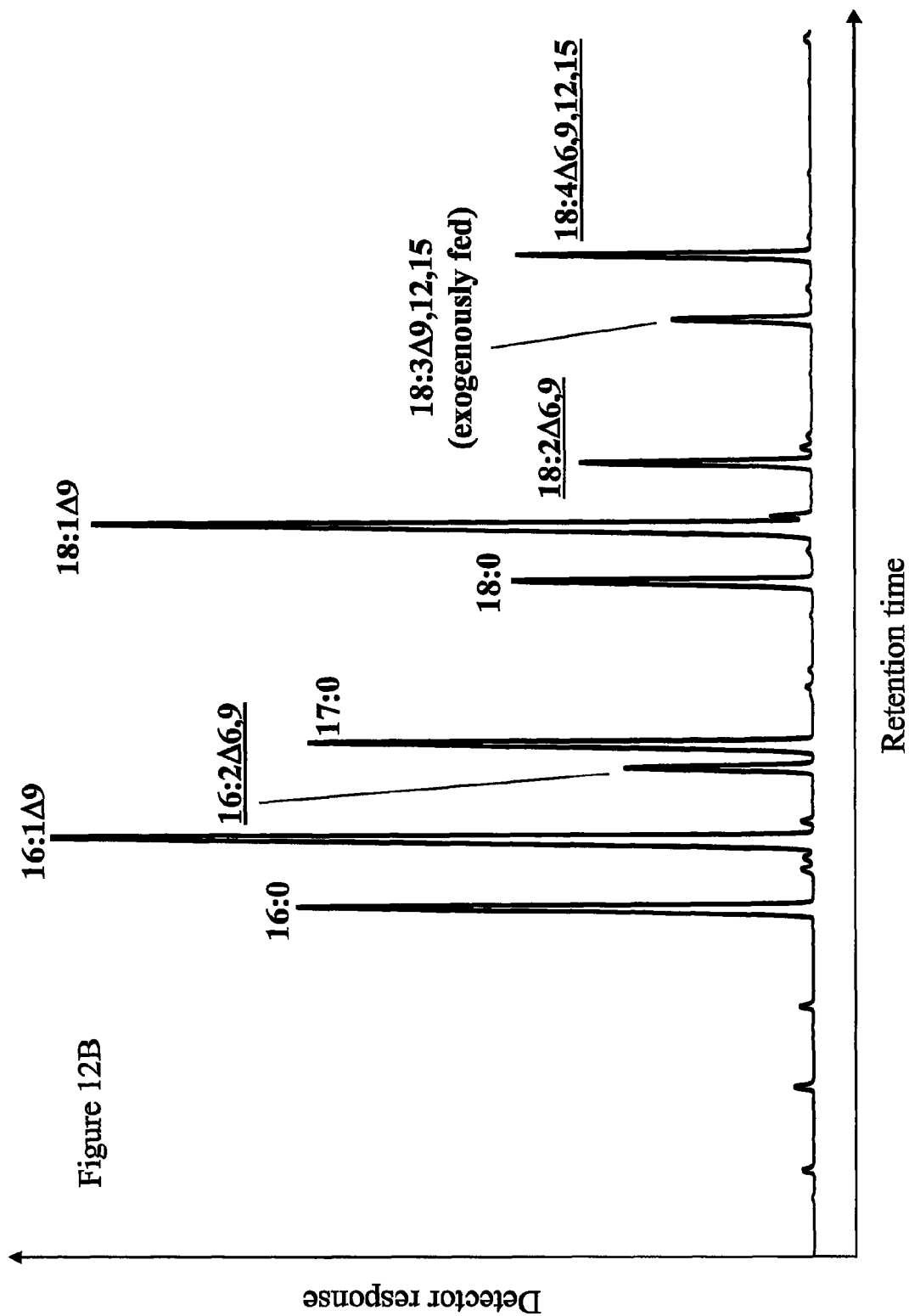
Figure 12C:
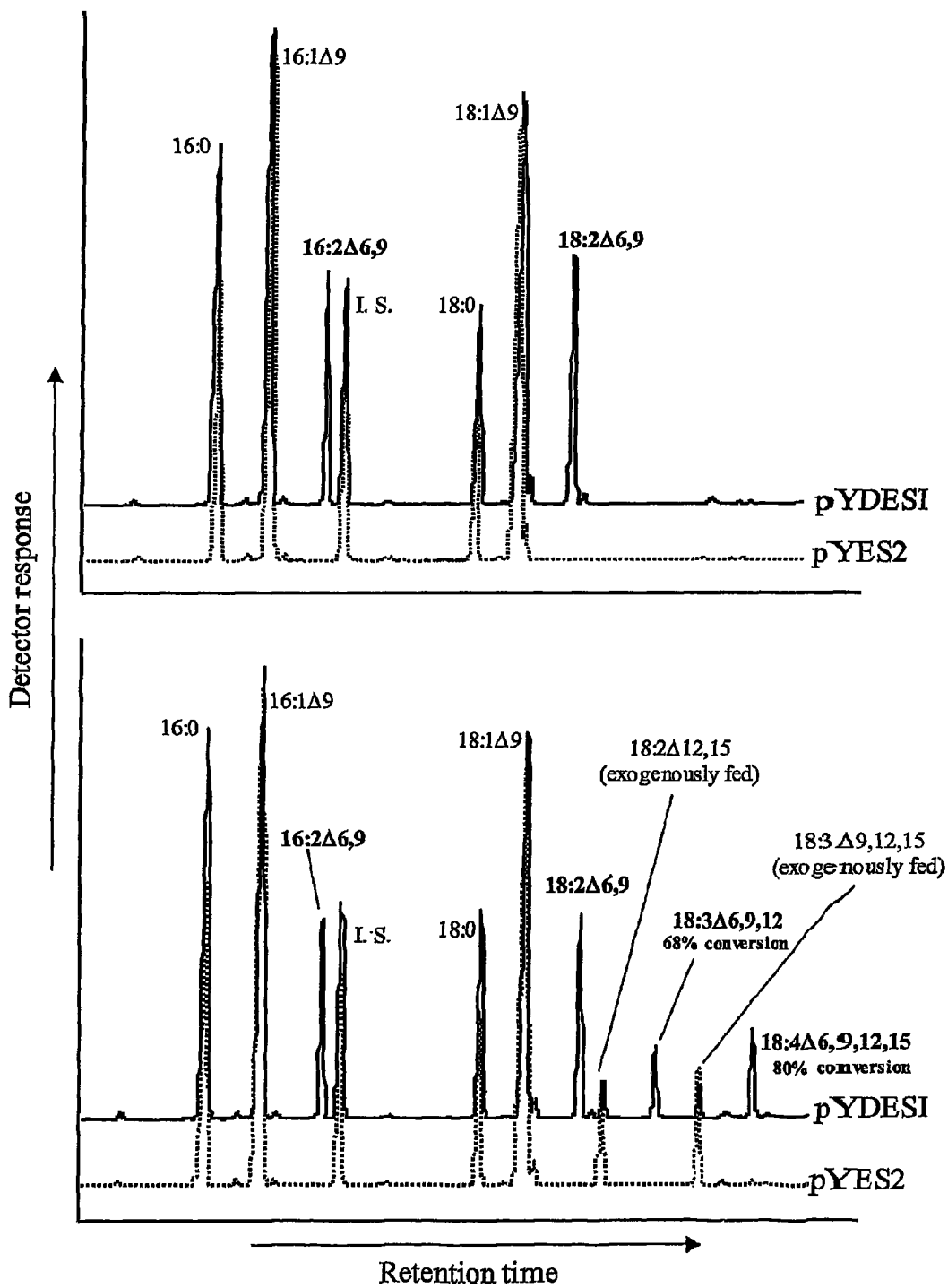
Figure 13:
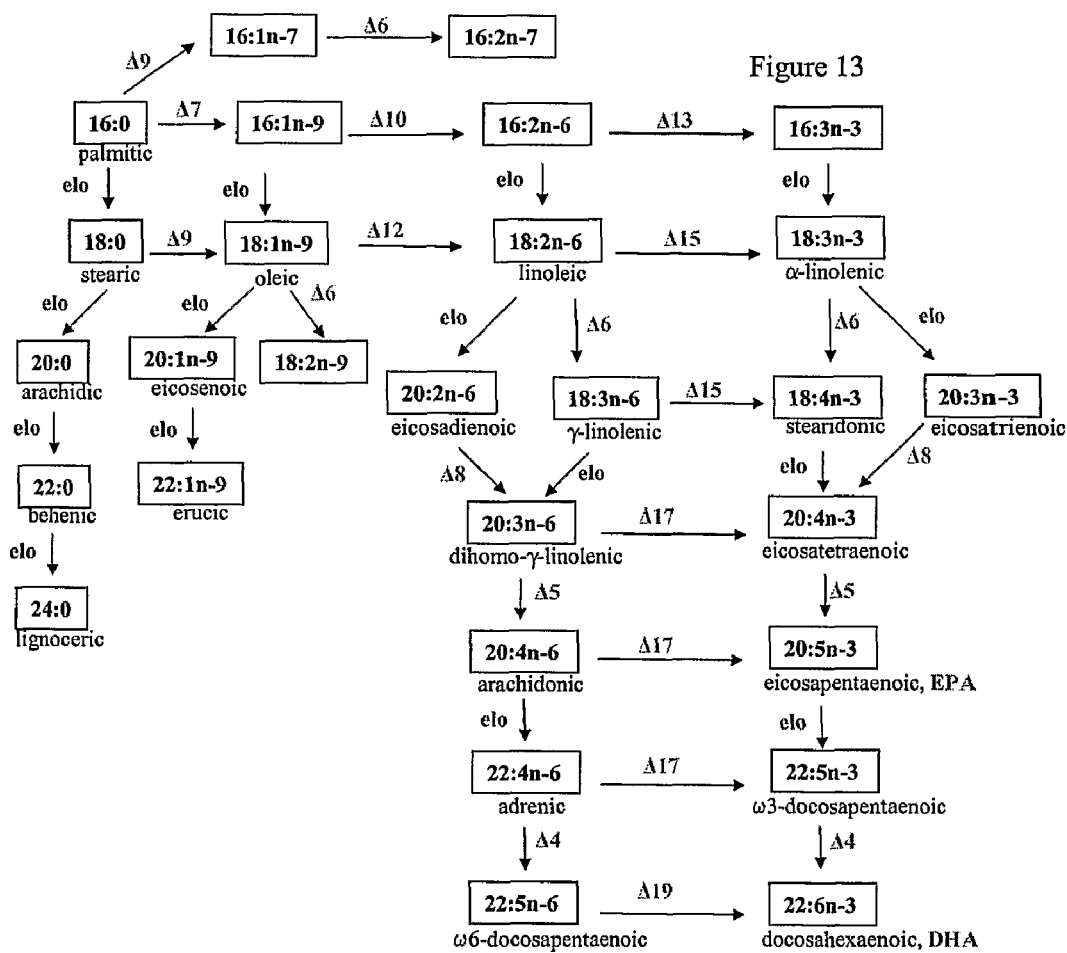

FIG. 11a is the nucleic acid sequence of desaturase O from *Thalassiosira pseudonana* (SEQ ID NO: 15); FIG. 11b is the cDNA sequence (SEQ ID NO: 16); FIG. 11c is the amino acid sequence (SEQ ID NO: 17); FIG. 11d is the nucleic acid sequence of desaturase O variant sequence from *Thalassiosira pseudonana* (SEQ ID NO: 18); and FIG. 11e is the amino acid sequence of said variant desaturase O (SEQ ID NO: 19);

FIGS. 12A and 12B is a GC analysis of FAMEs from yeast expressing TpDESI with exogenous substrates 18:2Δ9,12 (A) and 18:3Δ9,12,15 (B). New FAs produced from endogenous and exogenous substrates are underlined; FIG. 12C is a GC analysis of FAMEs from yeast transformed with a vector only control compared to yeast transformed with TpDESI;

FIG. 13 is an illustration of fatty acid synthesis pathways; and

Figure 14:
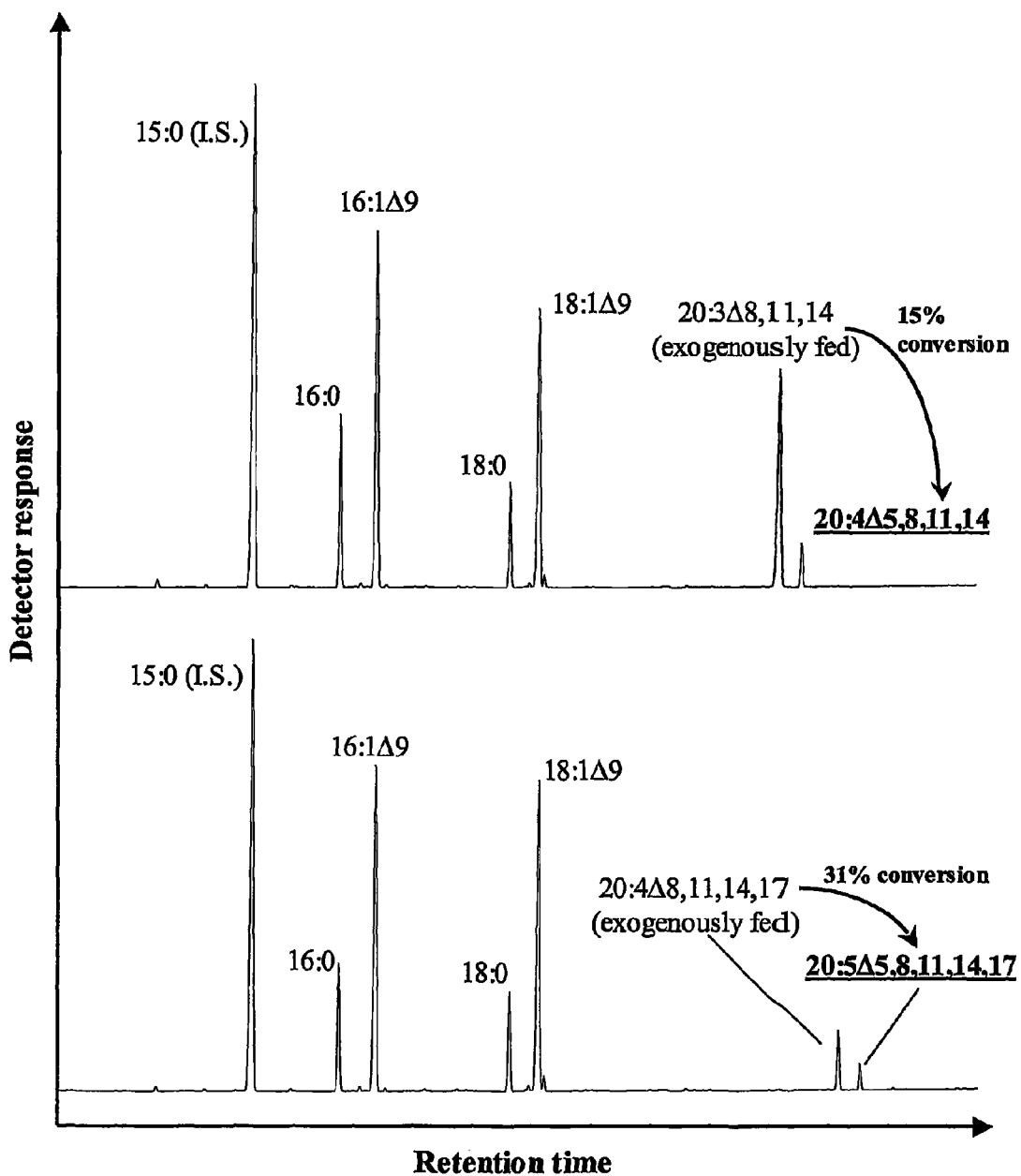

FIG. 14 is a GC analysis of FAMEs from yeast expressing TpDESO.

MATERIALS AND METHODS

Identification of Putative *Thalassiosira Pseudonana* Desaturase-Coding Sequences and Phylogenetic Analysis with Other Functionally Characterised Desaturases The draft genome of the diatom *T. pseudonana* has been sequenced to approximately nine times coverage by the whole genome shotgun method. Sequence data were produced by the US Department of Energy Joint Genome Institute (http://www.jgi.doe.gov/) and the raw sequence data were downloaded and installed on a local server. Batch tblastn searches were carried out using protein sequences of the following 13 known desaturases as query, including P1DES1 (AY332747, *Pavlova lutheri*), TFAD4 (AF489589, *Thraustochytrium* sp. ATCC 21685), TFAD5 (AF489588, *Thraustochytrium* sp. ATCC 21685), PtDEL5 (AY082392, *Phaeodactylum tricornutum*), PtDEL6 (AY082393, *Phaeodactylum tricornutum*), EgDEL8 (AF139720, *Euglena gracilis*), EgDEL4 (AY278558, *Euglena gracilis*), ZfDEL (AF309556, *Danio rerio*), BoDEL6 (U79010, *Borago officinalis*), HsDEL5 (AF084558, *Homo sapiens*), HsDEL6 (AF084559, *Homo sapiens*), CeDEL6 (AF031477, *Caenorhabditis elegans*) and CeDEL5 (AF078796, *Caenorhabditis elegans*).

All non-redundant sequences with an E value less than 0.001 were retrieved and assembled into contigs using the CAP3 sequence assembly program [18]. The contigs were translated into amino sequences in three frames in the orientation *indicated* by tblastn *result*. Putative desaturase gene models were constructed manually *based* on sequence homology and in frame GT-AG intron boundaries were *identified*.

Deduced amino acid sequences of all 12 putative desaturase sequences of *T. pseudonana* were aligned with the above 13 functionally characterised desaturases from other species, using ClustalX version 1.8 [19]. The alignment was then reconciled and further adjusted. Only nine near full-length *Thalassiosira* sequences were retained for further analyses.

A dataset of 250 conserved residue positions was used for construction of the phylogenetic tree. Distance analysis used the program protdist of the Phylip 3.5c package with a PAM250 substitution matrix and a tree was then built from the matrix using fitch (Fitch-Margoliash method). Bootstrap analyses were carried out with 1000 replicates using the neighbour-joining algorithm.

Cultivation of *T. Pseudonana*

*T. pseudonana* (CCAP 1085/12) was obtained from the Culture Collection of Algae and Protozoa (Dunstaffnage Marine Lab., Oban, PA34 4AD, Scotland, U.K.). The growth medium used was enriched artificial seawater medium (EASW), made up in 20 l batches as described previously [4]. The cultures were grown in one liter flasks at 15° C. with 50 µE m$^{-2}$ s$^{-1}$ constant illumination, and aeration provided by shaking the flasks at 150 rpm.

Cell density was monitored by counting cells with a haemocytometer. Nitrate concentration was determined periodically during the culture time by measuring the change of the medium absorbance at 220 nm [20].

RNA Extraction, cDNA Synthesis and RT-PCR Analysis

Total RNA was extracted from frozen cells harvested at different stages of growth with an RNeasy plant mini kit (Qiagen). First strand cDNA was synthesised from three µg of DNAse treated RNA using a Prostar First-strand RT-PCR kit (Stratagene). PCR was performed using undiluted and five-fold dilutions of cDNAs as followed: the reactions were heated to 95° C. for 5 min followed by 35 cycles at 95° C. for 30 s, 50° C. or 65° C. (for 18S rRNA and TpdesN respectively) for 30 s and 72° C. for 2 min, then a single 72° C. for 10 min As a marker for constitutive expression, the 18S rRNA gene was amplified with the primer TH18S5' (5'-GGTAAC-GAATTGTTAG-3') (SEQ ID NO: 22) and TH18S3' (5'-GTCGGCATAGTTTATG-3') (SEQ ID NO: 23). TpdesN cDNA was amplified using primers DESNR2 (5'-GT-GAGAGCACTAACCAAGCTT-3') (SEQ ID NO: 24) and DESN2 (5'-CAATCAGTAGGCTTCGTC G-3') (SEQ ID NO: 25). Aliquots of PCR reaction were electrophoresed through a 1% agarose gel. Identity of the diagnostic fragment amplified with TpdesN specific primers was verified by sequencing after cloning in the pGEM-T EasyVector (Promega).

Functional Characterisation of TpDESI in Yeast

The entire TpdesI coding region was amplified from *T. pseudonana* cDNA with primers DesINB 5'-GCG GGATCCACCATGGCTGGAAAAGGAGGAGAC-3' (SEQ ID NO: 26) (ORF start codon is indicated by bold type; underlined sequence is a BamHI site; italic sequence is an added alanine codon, not present in the original sequence of Pldes1) and DesICE 5'-GCGAATTC*TTA*CATGGCAGGGAAATC-3' (SEQ ID NO: 27) (ORF stop codon is indicated in bold type; underlined sequence is a EcoRI site). The Expand High Fidelity PCR system (Roche) was employed to minimise potential PCR errors. The amplified product was gel purified, restricted and cloned into the corresponding sites behind the galactose-inducible GAL1 promoter of pYES2 (Invitrogen) to yield the plasmid pYDES1. This vector was transformed into *S. cerevisiae* strain Invsc 1 (Invitrogen) by a lithium acetate method, and transformants were selected on minimal medium plates lacking uracil.

For functional expression, cultures were grown at 25° C. in the presence of 2% (w/v) raffinose and 1% (w/v) Tergitol NP-40 (Sigma). Expression of the transgene was induced when $OD_{600nm}$ reached 0.2-0.3 by supplementing galactose to 2% (w/v). At that time, the appropriate fatty acids were added to a final concentration of 50 µM. Incubation was carried out at 25° C. for three days.

Functional Characterisation of TpDESN in Yeast

Genomic DNA from *T. pseudonana* cells was extracted using the DNA isolation kit Puregene (Gentra Systems) and 100 ng was used to amplify the entire TpdesN coding region with primers DesNNB 5'-GCGGGATCCACCATGGCTGAC*TTT*CTCTCCGGC-3' (SEQ ID NO: 28) (ORF start codon is indicated by bold type; underlined sequence is a BamHI site; italic sequence is an added alanine codon, not present in the original sequence of TpdesN) and DesNCE 5'-GCGAATTCTCAATCAGTAGGCTTCGT-3' (SEQ ID NO: 29) (ORF stop codon is indicated in bold type; underlined sequence is a EcoRI site). The Expand High Fidelity PCR system (Roche) was employed to minimise potential PCR errors. The amplified product was gel purified, restricted with EcoRI and BamHI and cloned into the corresponding sites behind the galactose-inducible GAL1 promoter of pYES2 (Invitrogen) to yield the plasmid pYDESN. The fidelity of the cloned PCR product was checked by sequencing. The vector pYDESN was then transformed into *S. cerevisiae* strain Invsc1 (Invitrogen) by a lithium acetate method, and transformants were selected on minimal medium plates lacking uracil.

For the feeding experiment with PUFAs, cultures were grown at 22° C. in the presence of 2% (w/v) raffinose and 1% (w/v) Tergitol NP-40 (Sigma). Expression of the transgene was induced when $OD_{600nm}$ reached 0.2-0.3 by supplementing galactose to 2% (w/v). At that time, the appropriate fatty acids were added to a final concentration of 50 µM. Incubation was carried out at 22° C. for three days and then 15° C. for another three days. For the feeding experiment with saturated fatty acids, a single Invsc1 colony transformed with pYES2 (empty plasmid, control) or pYDESN was inoculated in 10 ml of minimal media minus uracil containing 2% raffinose and grown overnight at 30° C. with shaking (300 rpm). After 16-24 h, cells were collected by spinning at 4500 rpm for 10 min After discarding the supernatant, the cell pellet was resuspended in the same medium mentioned above supplemented with 2% galactose and 1% tergitol, to obtain a cell density of $5 \times 10^7$ cells/ml. Fifteen ml of this cell suspension were added to a 100 ml-flask with or without addition of saturated fatty acids (as mentioned in the text) at 500 µM final concentration. Desaturase induction was then carried out at 20° C. with shaking (300 rpm) for three days.

Fatty Acid Analysis

Microalgae or yeast cells were harvested by centrifugation. Total fatty acids were extracted and transmethylated as previously described [4]. Most FAMEs were identified by comparison of retention times to a 37 FAME mix (Supelco). PUFA FAMEs were also identified by comparison to a sample of standard Menhaden oil (Supelco) transmethylated as per the samples.

Dimethyl disulphide (DMDS) adducts were used to determine the double bond position in identified and unidentified monounsaturated FAMEs. These were made by adding together 50 µl DMDS (Aldrich), 100-1000 ng FAMEs dissolved in 50 µl hexane, and 5 µl 150 mg ml$^{-1}$ iodine in diethyl ether. This solution was heated at 40° C. for 15 h and partitioned with 200 µl hexane and 100 µl 5% (w/v) sodium thiosulphate. The hexane phase was removed, dried under vacuum, reconstituted in 50 µl fresh hexane and used for GC-MS analysis. A Trace GC 2000 (ThermoQuest) fitted with a 30 m×0.25 mm×0.5 µm film thickness ZB-1 column (Phenomenex) was used to chromatograph 2 µl DMDS adducts injected at 250° C. and a 50:1 split ratio with He as carrier gas at 0.6 ml min$^{-1}$ in constant flow mode. The oven program was 120° C. for 1 min then to 340° C. at 5° C. min$^{-1}$ Mass spectra were obtained using a GCQ (ThermoQuest) mass spectrometer operating in full scan mode over 50-500 m/z. Picolinyl esters were also made from FAMEs to confirm their identities. These were obtained by adding 15 µl freshly prepared 2:1 (v/v) 3-(hydroxymethyl)-pyridine (Aldrich): potassium tert butoxide 1 M solution in tetrahydrofuran (Aldrich) to 50 µl FAMEs dissolved in dichloromethane. This solution was heated at 40° C. for 30 min and partitioned with 200 µl hexane and 100 µl 2.5% (w/v) sodium hydrogen carbonate. The hexane phase was removed, dried under vacuum and reconstituted in 50 µl fresh hexane. Picolinyl esters were injected and separated by GC-MS using the same conditions as for DMDS adducts; Sperling P., Zahringer U. and Heinz E. (1998) A sphingolipid desaturase from higher plants. J. Biol. Chem. 273, 28590-28596; Sperling P., Libisch B., Zahringer U., Napier J. A. and Heinz E. (2001) Functional identification of a D8-sphingolipid desaturase from *Borago officinalis*. Arch. Biochem. Biophys. 388, 293-298; Whitney H. M., Michaelson, L. V., Sayanova, O., Pickett J. A. and Napier, J. A. (2003) Functional characterization of two two cytochrome b5-fusion desaturases from *Anemone leveillei*: The unexpected identification of a fatty acid Δ6-desaturase. Planta 217, 983-992; each of which are incorporated by reference.

EXAMPLES

Example 1

Figure 1A:
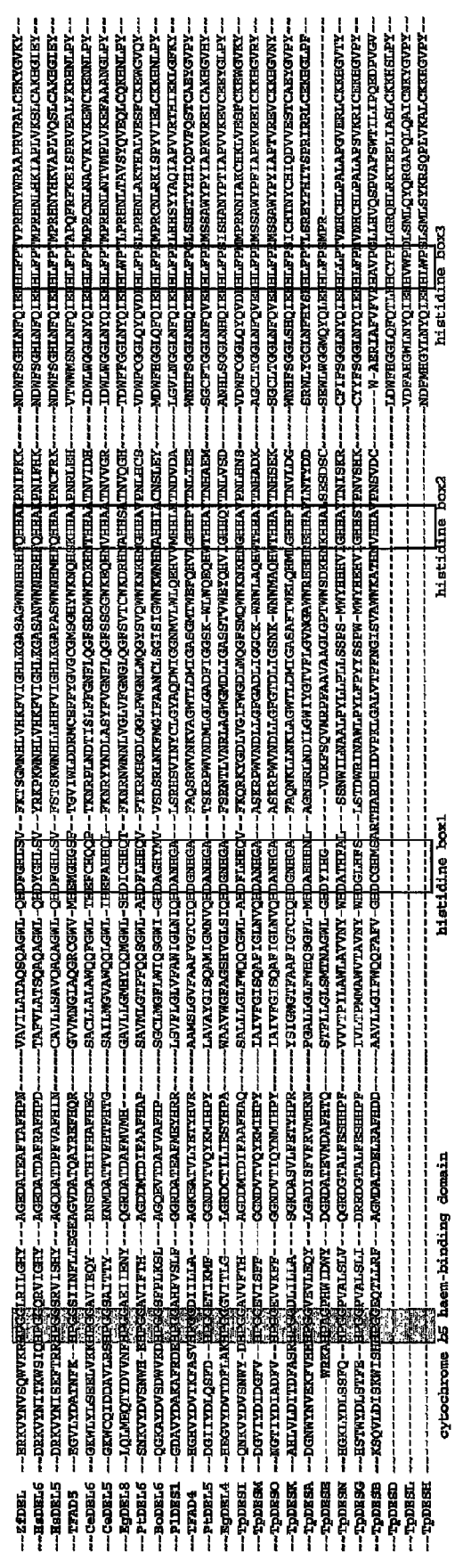

Identification and Phylogenetic Analysis of Putative *T. Pseudonana* Desaturase Sequences with Other Functionally Characterised Desaturases Tblastn searches with 13 functionally characterised desaturases revealed 427 non-redundant raw sequences with E values less than 0.001. Twelve unique contigs were assembled after retrieving these sequences and gene models were constructed manually based on sequence homology. These 12 gene contigs were arbitrarily designated TpdesA to TpdesL. All 12 showed significant sequence similarity to query sequences with 9 containing near full length open reading frames compared to other known desaturases (FIG. 1A) (SEQ ID NO: 30 to SEQ ID NO: 38). Interestingly, the predicted amino acid sequence of all nine T. pseudonana desaturases have a characteristic fused cytochrome b5 haem-binding domain (HP[G/A]G) at their N-terminus and three histidine boxes (H[X]3-4H, H[X]2-3HH AND Q[X]2-3HH) with the replacement of the first histidine by glutamine in the third histidine box in all but two of the predicted proteins (TpDESA and TpDESB). These are common characteristics of a large subgroup of front-end acyl group desaturases [21]. These histidine-box motifs are critical for desaturase activity, most likely because they serve to coordinate the diiron-oxo component of the active site. Three remaining sequences (TpDESD, TpDESL and TpDESH) appear to be partial, covering only the C-terminal end of desaturases, but nevertheless they do contain a typical third histidine box of the above mentioned subgroup of desaturases (FIG. 1A) (SEQ ID NO: 30 to SEQ ID NO: 38).

Figure 1B:
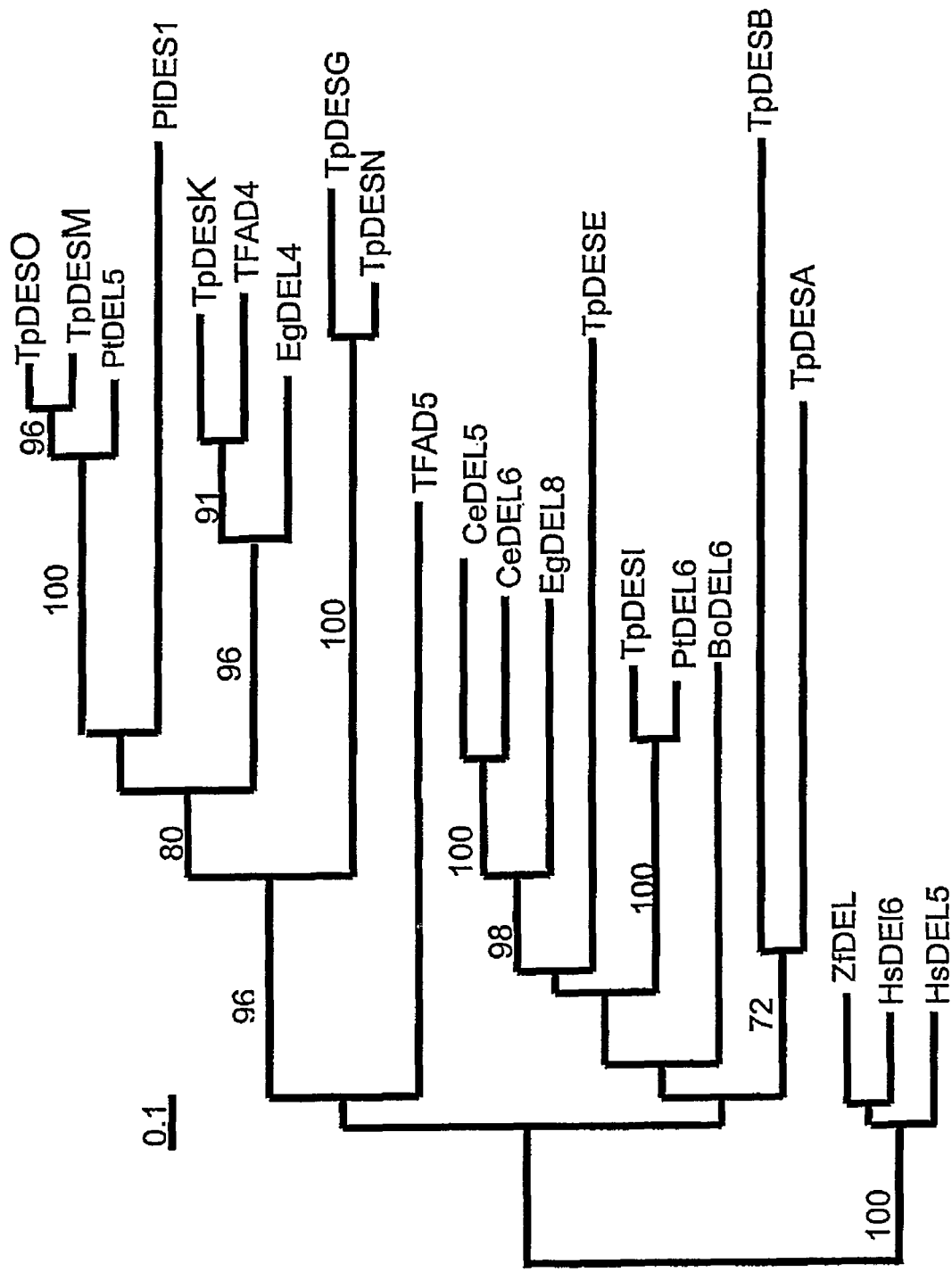

In order to gain insight into the relationships of these *T. pseudonana* sequences to other functionally characterised desaturases and especially algal desaturases, we constructed an unrooted phylogenetic tree using a Fitch-Margoliash method with statistical confidence measured by bootstrap analysis (FIG. 1B). Relationships of four putative *T. pseudonana* desaturases are in well supported (>70% bootstrap value) subgroups with at least one functionally characterised desaturase from other species. Both TpDESM and TpDESO grouped with PtDEL5, a Δ5-desaturase from another diatom, *P. tricornutum* [5], suggesting these two enzymes may also have a Δ5-desaturase activity. Similarly TpDESK is grouped with two Δ4-desaturases TFAD4 and EgDEL4 from *Thraustochytrium* sp. ATCC21685 [22] and *E. gracilis* respectively. TpDESI grouped with PtDEL6, a Δ6-desaturase from *P. tricornutum*. This indicates that TpDESK and TpDESI may have Δ4 and Δ6-desaturase activities respectively. However, as enzymes with different regioselectivities are also found in a well supported subgroup (EgDEL8, CeDEL5 and CeDEL6; Δ8, Δ5 and Δ6-desaturase respectively) and regioselectivity may even derive independently after a more recent duplication (CeDEL5 and CeDEL6) [23] predictions based on homology can be misleading and it is essential to functionally characterise each enzyme.

The remaining five *T. pseudonana* sequences fall into three separate subgroups (TpDESE; TpDESA and TpDESB; TpDESG and TpDESN) which do not group with any other known functional desaturases with high confidence. It is therefore possible that these proteins exhibit novel regioselectivity. The current study focussed on the characterisation of one of these proteins, TpDESN.

Example 2

Temporal Expression of TpDESN Gene

Figure 2:
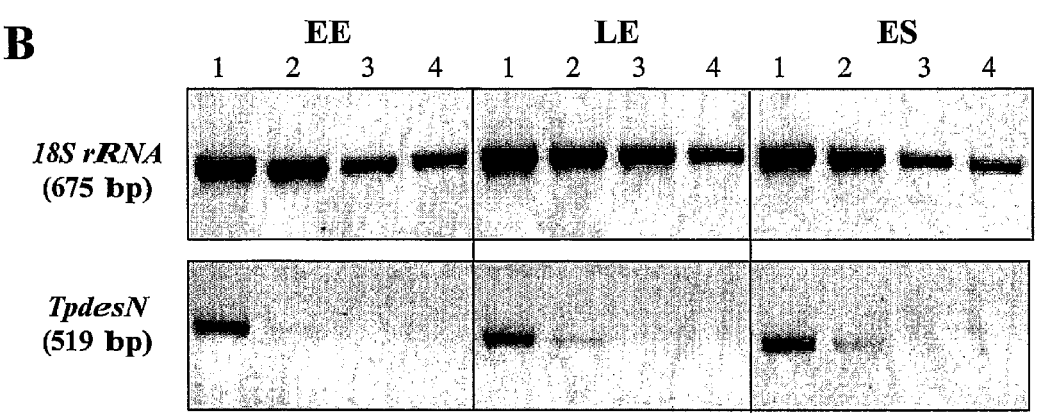

RT-PCR analysis of TpdesN transcript was conducted at different stages of algal growth in order to establish if and when this gene is expressed. After RNA extraction and cDNA synthesis, TpdesN specific PCR products were amplified. PCR amplification of the 18S rDNA gene was performed as a control for the quantity of cDNA used during PCR reactions. FIG. 2 shows that the diagnostic 519 by cDNA amplification product expected for TpdesN was present at similar level at the different stages of cultivation of the microalga cells. Thus, TpdesN is transcriptionally active at a constitutive level during *Thalassiosira* growth, suggesting that it may encode a desaturase with a housekeeping function.

Example 3

Functional Characterisation of TpDESN in Yeast

The putative desaturase sequence annotated TpdesN was contained on a genomic DNA contig of 2580 by on which no introns was detected. To establish the function of the protein encoded by this gene, the full-length sequence was amplified from genomic DNA. An alanine codon containing a G as the first letter was added immediately downstream of the start codon of TpdesN to ensure optimal translation in yeast [24]. The TpdesN ORF is 1434 by long, and encodes a 477 amino acid protein TpDESN (FIG. 1C) (SEQ ID NO: 1), having a molecular weight of 53.8 kDa. Analysis of the secondary structure of TpDESN using SOSUI software (http://sosui.proteome.bio.tuat.ac.jp/sosuiframe0.html) [25] predicted four transmembrane regions (not shown). Alignment of TpDESN with functionally characterised desaturase sequences mentioned above indicated an overall identity of 25%, with the cytochrome b5-like domain and the three conserved histidine-rich motif areas showing greatest homology.

Figure 3:
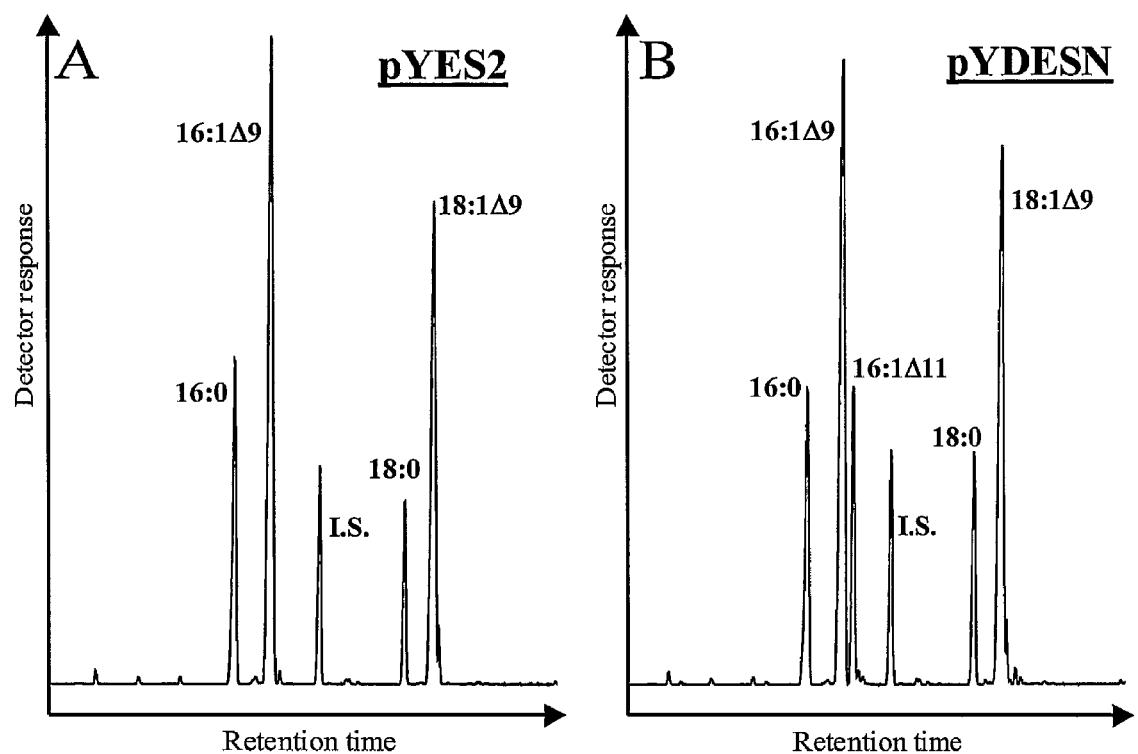
Figure 4:
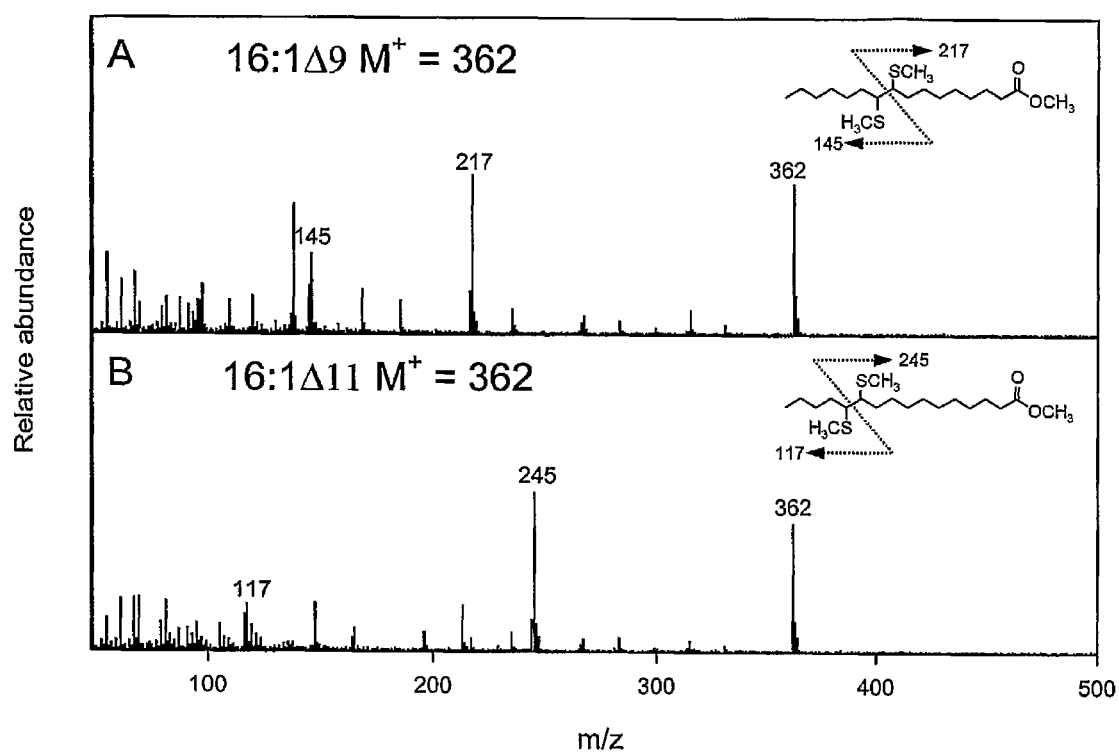

The primary sequence of TpDESN exhibited typical features of front-end desaturases involved in PUFA synthesis. In order to characterise the specificity of this protein, PUFAs (18:2Δ9,12; 20:2Δ11,14; 20:3Δ8,11,14; 22:4Δ5,8,11,14; 18:3Δ9,12,15; 20:3Δ11,14,17; 20:4Δ8,11,14,17; 22:5Δ7,10,13,16,19) where first fed to the host yeast transformed with pYDESN and the vector alone (pYES2) as a control. Unexpectedly, after six days of incubation, TpDESN did not desaturate any of the supplemented PUFA substrate. Furthermore, there did not appear to be any production of 18:2Δ9,12 from endogenous 18:1Δ9. However, a significant increase was observed for a peak eluting in the range of sixteen carbon monounsaturated FAMEs in the yeast transformed with pYDESN (FIG. 3). The position of the double bond in this product was determined by GC-MS analysis of FAMEs derived to DMDS adducts [26] and picolinyl esters. The DMDS adduct of 16:1Δ9 FAME yielded two major fragments at m/z 145 and 217 (FIG. 4A). Fragmentation of the increased FAME peak found in unfed or fed yeast transformed with pYDESN produced two diagnostic fragments at m/z 117 and 245 (FIG. 4B). This fragmentation pattern was indicative of an Δ11 monounsaturated sixteen carbon FAME, 16:1Δ11, suggesting that TpDESN encoded a new Δ11-desaturase. Small amounts of this FA have also been measured in Thalassiosira cells (Table 1). To further substantiate these results, yeast transformed with pYDESN and the control empty vector, pYES2, were cultivated in medium supplemented with saturated FA (14:0; 16:0; 18:0) representing potential substrates for the synthesis of the monounsaturated product. Yeast fatty acid profiles were analysed after three days of incubation at 20° C. Results in Table 2 showed that a small amount of 16:1Δ11 (0.23% of total FAs) was detected in yeast transformed with pYES2, suggesting endogenous synthesis of this FA from 16:0. This FA accumulated at a higher level in both types of transformed yeast after feeding with 14:0, with values up to 5.84% in pYDESN transformants. A possible explanation for this increase in the pYES2 transformants is that the endogenous yeast 49-desaturase was able to use additional 14:0 to produce 14:1Δ9 that was subsequently elongated to 16:1Δ11. Moreover, it has been reported that wild type yeast cells cultivated in media supplemented with 14:1Δ9 synthesised 16:1Δ11 by Elo1p-dependent carboxy terminal elongation [27]. After 18:0 supplementation, the percentage of 16:1Δ11, of about 6% total FAs, was similar to that observed after feeding with 16:0. Presence of extra 18:0 could lead to an inhibition of the 16:0 chain elongation system, which might allow more 16:0 to be available for Δ11-desaturation. On the other hand, 18:1Δ11 represents 1.2% of the total FAs in transgenic yeast. No variation in its proportion was monitored under the different conditions of incubation, even after supplementation with 18:0 in pYDESN transformants. This suggests that this FA originates from elongation of 16:1Δ9 rather than Δ11-desaturation of 18:0.

Example 4

Functional Characterisation of TpDESI in Yeast

To establish the function of TpDESI, the full-length cDNA was expressed in the yeast Invsc1 under the control of an inducible galactose promoter. Potential substrates of front-end desaturases (18:2Δ9,12; 18:3Δ9,12,15; 20:3Δ8,11,14; 20:4Δ8,11,14,17; 22:4Δ7,10,13,16; 22:5Δ7,10,13,16,19) were tested. FIGS. 12A and 12B show that after supplementation of the medium with $18:2\Delta^{9,12}$ and $18:3\Delta^{9,12,15}$ respectively, and after three days of incubation, yeast cells containing pYDESI had extra fatty acids. Extra peaks observed when cells were fed with 18:2Δ9,12 had a retention time identical to 16:2Δ6,9, 18:2Δ6,12 and 18:3Δ6,9,12 (FIG. 12A). Extra peaks observed when cells were fed with 18:3Δ9,12,15 had a retention time identical to 16:2Δ6,9, 18:2Δ6,12 and 18:4Δ6,9,12,15 (FIG. 12B). These results demonstrate that TpdesI encodes a Δ6-desaturase which can introduce double bond in exogenously fed 18:2Δ9,12 and 18:3Δ9,12,15 fatty acids, but also in endogenous 16:1Δ9 and 18:1Δ9 fatty acids. Percentages of conversion of these different substrates are given in Table 3.

Fatty acid profiling of marine microalgae had shown that *T. pseudonana* represents a good candidate to discover genes involved in the production and storage of PUFAs [4]. Analysis of the recently completed draft genome of this microalga revealed the presence of many candidate genes for elongase and desaturase activities most probably involved in catalysing different steps of the PUFA biosynthetic process. We have identified 12 possible desaturase genes, 9 of which there is sufficient sequence information to demonstrate that they exhibit typical features of front-end desaturases, i.e. a cytochrome b5 domain in the N-terminus and three histidine clusters located at highly conserved regions. Phylogenetic analysis revealed that several of the genes are closely related to a number of previously characterised front-end desaturases involved in PUFA synthesis. However, the current work highlights the fact that desaturase function, in terms of regioselectivity, cannot solely be based on prediction from primary amino acid sequence homology.

The fatty acid profile of *T. pseudonana* cells is quite diverse (Table 1), with the health beneficial EPA (20:5Δ5,8,11,14,17) and DHA (22:6Δ4,7,10,13,16,19) accounting for a large proportion. However, the number of desaturase gene sequences found in the genome was higher than we expected based on the number of different desaturation reactions required to produce the diversity of FA in this microalga. This suggested that non-obvious desaturation reactions might also occur in the *Thalassiosira* cells. As a first step to establishing function of the many putative desaturase sequences, we focused on the TpdesN contig due to the fact that the sequence was full-length and intronless. A temporal expression study showed that TpdesN was constitutively transcribed during algal cultivation. Expression of the TpdesN ORF in yeast supplemented with PUFAs as potential substrates for desaturation revealed no new products. There was also no evidence of activity with the endogenous 18:1Δ9 which excludes the possibility that TpDESN acts as a Δ12-desaturase. However, an increase in the peak area of a FAME eluting in the range of the sixteen carbon FAMEs was identified and GC-MS based analysis revealed this to be 16:1Δ11 fatty acid. Small amounts of this FA are also present in wild type yeast. However, quantitative comparison of FA levels in the empty vector pYES2 and pYDESN transformants showed that proportions of 16:1Δ11 increased in the presence of TpdesN in both unfed cells and cells that had been fed different saturated FA. No other changes in either peak area or new peaks were detected in pYDESN transformants, indicating that TpDESN is specifically involved in conversion of 16:0 to 16:1Δ11.

The presence of small amounts of 16:1Δ11 have previously been reported in many microalgae, including *T. pseudonana*. However, a function for this FA in algal cells has not been established. The low quantity observed in many marine microalgae suggests that it may act as an intermediate in an as yet unidentified biosynthetic pathway. In insect cells, 16:1Δ11 represents an important precursor for pheromone synthesis, where it is produced by an acyl-CoA Δ11'-desaturase. Interestingly, the insect Δ11-desaturases do not possess a cytochrome b5 domain in their N-terminal region. This represents a major primary structure difference compared with TpDESN. The cytochrome b5 domain is not a determinant of the substrate specificity [28]. Alignment of the desaturase domain of TpDESN with the full sequence of insect Δ11-desaturases showed an identity of 20% (data not shown). In insect cells, Δ11-desaturases are more or less specific depending on the origin of the sequence and well-documented reviews exist on this subject [14,15].

In conclusion therefore, although the TpDESN primary sequence is very similar to front-end desaturases, it should not be considered a member of this family of desaturases because it acts only on 16:0. Identification of such a novel enzyme expands the functional repertoire of the membrane-bound desaturases and it should provide useful comparative information for understanding phylogenetic relationships between these enzymes. One question that remains to be answered regards whether cytochrome b5 was independently fused to desaturases that had already acquired their different specificities, or whether an ancestral fusion protein for proximal lipid modification duplicated and subsequently evolved into different desaturases. Studies of the primary structure of the different PUFA desaturases support the fact that enzyme conversion (i.e. change of specificity) can be achieved through a relatively few structural changes [29]. The high degree of homology between the many potential front-end desaturases identified in the genome of *T. pseudonana* support this notion. Given the FA profile of *T. pseudonana* cells and the complexity of the desaturase gene family it is likely that different genes will encode Δ4, Δ5 and Δ6 desaturases. It will now be very interesting to functionally characterise these remaining putative desaturase genes and study the relationship between regioselectivity, primary amino acid sequence and phylogenetic relationship. A crystal structure for these enzymes is still not available due to technical difficulties in obtaining sufficient quantities of purified membrane-bound protein. Molecular genetic approaches involving site-directed mutagenesis have provided new insight into structure-function relationships, including for example that residues in close proximity to the histidine motifs have been found to be involved in shifting the ratio of desaturation/hydroxylation activities [30]. Detailed comparative analyses and computer modeling of these diverse desaturases from *T. pseudonana* may further guide site-directed mutagenesis studies aimed at defining key residues controlling substrate specificity and regioselectivity of the introduced double bond.

REFERENCES

[1] Napier, J. A., Sayanova, O., Sperling, P. and Heinz, E. (1999) Trends Plant. Sci. 4, 2-4.
[2] van de Loo, F. J., Fox, B. G. and Somerville, C. R. (1993) in: Unusual fatty acids (Moore, T. S., ed.) Lipid Metabolism in Plants, pp. 91-126.
[3] Vazhappilly, R. and Chen, F. (1998) J. Am. Oil Chem. Soc. 75, 393-397.
[4] Tonon, T., Harvey, D, Larson, T. R. and Graham, I. A. (2002) Phytochemistry 61, 15-24.
[5] Domergue, F., Lerchl, J., Zahringer, U. and Heinz, E. (2002) Eur. J. Biochem. 269, 4105-4113.
[6] Meyer, A., Cirpus, P., Ott, C., Schlecker, R., Zahringer, U. and Heinz, E. (2003) Biochemistry 42, 9779-9788.
[7] Tonon, T., Harvey, D., Larson, T. R. and Graham, I. A. (2003) FEBS Lett. 553, 440-444.
[8] Lopez Alonso, D., Garcia-Maroto, F., Rodriguez-Ruiz, J., Garrido, J. A. and Vilches, M. A. (2003) Biochem. Syst. Ecol. 31, 1111-1124.
[9] Pereira, S. L., Leonard, A. E. and Mukerji, P. (2003) Prost. Leuko. Essent. Fatty Acids 68, 97-106.
[10] Shanklin, J., Whittle, E. and Fox, D. C. (1994) Biochemistry 33, 12787-12794.
[11] Volkman, J. K., Dunstan, G. A., Jeffrey, S. W. and Kearney P. S. (1991) Phytochemistry 30, 1855-1859.
[12] Dunstan, G. A., Volkman, J. K., Barrett, S. M. and Garland, C. D. (1993) J. Appl. Phycol. 5, 71-83.
[13] Brown, M. R., Dunstan, G. A., Norwood, S. J. and Miller K. A. (1996) J. Phycol. 32, 64-73.
[14] Knipple, D. C., Rosenfield, C.-L., Nielsen, R., You, K. M. and Jeong, S. E. (2002) Genetics 162, 1737-1752.
[15] Roelofs, W. L., Liu, W., Hao, G., Jiao, H., Rooney, A. P. and Linn Jr, C. E. (2002) Proc. Natl. Acad. Sci. USA 99, 13621-13626.
[16] Roelofs, W. L. and Bjostad, L. (1984) Bioorg. Chem. 12, 279-298.
[17] Roelofs, W. L. and Wolf, W. A. (1988) J. Chem. Ecol. 14, 2019-2031.
[18] Huang, X. and Madan, A. (1999) Genome Res. 9, 868-877.
[19] Thompson, J. D., Gibson, T. J., Plewniak, F., Jeanmougin, F. and Higgins, D. G. (1997) Nucleic Acids Res. 25, 4876-4882.
[20] Collos, Y., Momet, F., Sciandra, A., Waser, N., Larson, A. and Harrison, P. J. (1999) J. Appl. Phycol. 11, 179-184.
[21] Sperling, P., Ternes, P., Zank, T. K. and Heinz, E. (2003) Prost. Leuko. Essent. Fatty Acids 68, 73-95.
[22] Qiu, X., Hong, H. and MacKenzie, S. L. (2001) J. Biol. Chem. 276, 31561-31566.
[23] Michaelson, L. V., Napier, J. A., Lewis, M., Griffiths, G., Lazarus, C. and Stobart A. K. (1998) FEBS Lett. 439, 215-218.
[24] Kozak, M. (1987) Nucleis Acid Res. 15, 8125-8148.
[25] Hirokawa, T., Seah, B. C. and Mitahu, S. (1998) Bioinformatics 14, 378-379.
[26] Buser, H. R., Arn, H., Guerin P. and Rauscher, S. (1983) Anal. Chem. 55, 818-822.
[27] Schneiter, R., Tatzer, V., Gogg, G., Leitner, E. and Kohlwein, S. D. (2000) J. Bact. 182, 3655-3660.
[28] Libisch, B., Michaelson, L. V., Lewis, M. J., Shewry, P. R. and Napier, J. A. (2000) Biochem. Biophys. Res. Commun. 279, 779-85.
[29] Cahoon, E. B., Lindquist, Y., Schneider, G. and Shanklin, J. (1997) Proc. Natl. Acad. Sci. USA 94, 4872-4877.
[30] Broun, P., Shanklin, J., Whittle, E. and Somerville, C. (1998) Science 282, 1315-1317.

SEQUENCE LISTING

```
<160> NUMBER OF SEQ ID NOS: 38

<210> SEQ ID NO 1
<211> LENGTH: 477
<212> TYPE: PRT
<213> ORGANISM: Thalassiosira pseudonana

<400> SEQUENCE: 1

Met Asp Phe Leu Ser Gly Asp Pro Phe Arg Thr Leu Val Leu Ala Ala
1               5                   10                  15

Leu Val Val Ile Gly Phe Ala Ala Ala Trp Gln Cys Phe Tyr Pro Pro
                20                  25                  30

Ser Ile Val Gly Lys Pro Arg Thr Leu Ser Asn Gly Lys Leu Asn Thr
            35                  40                  45

Arg Ile His Gly Lys Leu Tyr Asp Leu Ser Ser Phe Gln His Pro Gly
        50                  55                  60

Gly Pro Val Ala Leu Ser Leu Val Gln Gly Arg Asp Gly Thr Ala Leu
65                  70                  75                  80

Phe Glu Ser His His Pro Phe Ile Pro Arg Lys Asn Leu Leu Gln Ile
                85                  90                  95

Leu Ser Lys Tyr Glu Val Pro Ser Thr Glu Asp Ser Val Ser Phe Ile
                100                 105                 110

Ala Thr Leu Asp Glu Leu Asn Gly Glu Ser Pro Tyr Asp Trp Lys Asp
            115                 120                 125
```

```
Ile Glu Asn Asp Asp Phe Val Ser Asp Leu Arg Ala Leu Val Ile Glu
130                 135                 140

His Phe Ser Pro Leu Ala Lys Glu Arg Gly Val Ser Leu Val Glu Ser
145                 150                 155                 160

Ser Lys Ala Thr Pro Gln Arg Trp Met Val Leu Leu Leu Leu Leu Ala
                165                 170                 175

Ser Phe Phe Leu Ser Ile Pro Leu Tyr Leu Ser Gly Ser Trp Thr Phe
            180                 185                 190

Val Val Val Thr Pro Ile Leu Ala Trp Leu Ala Val Val Asn Tyr Trp
        195                 200                 205

His Asp Ala Thr His Phe Ala Leu Ser Ser Asn Trp Ile Leu Asn Ala
210                 215                 220

Ala Leu Pro Tyr Leu Leu Pro Leu Leu Ser Ser Pro Ser Met Trp Tyr
225                 230                 235                 240

His His His Val Ile Gly His Ala Tyr Thr Asn Ile Ser Lys Arg
                245                 250                 255

Asp Pro Asp Leu Ala His Ala Pro Gln Leu Met Arg Glu His Lys Ser
                260                 265                 270

Ile Lys Trp Arg Pro Ser His Leu Asn Gln Thr Gln Leu Pro Arg Ile
            275                 280                 285

Leu Phe Ile Trp Ser Ile Ala Val Gly Ile Gly Leu Asn Leu Leu Asn
        290                 295                 300

Asp Val Arg Ala Leu Thr Lys Leu Ser Tyr Asn Asn Val Val Arg Val
305                 310                 315                 320

Glu Lys Met Ser Ser Ser Arg Thr Leu Leu His Phe Leu Gly Arg Met
                325                 330                 335

Leu His Ile Phe Val Thr Thr Leu Trp Pro Phe Leu Ala Phe Pro Val
                340                 345                 350

Trp Lys Ala Ile Val Trp Ala Thr Val Pro Asn Ala Ile Leu Ser Leu
            355                 360                 365

Cys Phe Met Leu Asn Thr Gln Ile Asn His Leu Ile Asn Thr Cys Ala
        370                 375                 380

His Ala Ser Asp Asn Asn Phe Tyr Lys His Gln Val Val Thr Ala Gln
385                 390                 395                 400

Asn Phe Gly Arg Ser Ser Ala Phe Cys Phe Ile Phe Ser Gly Gly Leu
                405                 410                 415

Asn Tyr Gln Ile Glu His His Leu Leu Pro Thr Val Asn His Cys His
            420                 425                 430

Leu Pro Ala Leu Ala Pro Gly Val Glu Arg Leu Cys Lys Lys His Gly
        435                 440                 445

Val Thr Tyr Asn Ser Val Glu Gly Tyr Arg Glu Ala Ile Ile Ala His
450                 455                 460

Phe Ala His Thr Lys Asp Met Ser Thr Lys Pro Thr Asp
465                 470                 475
```

<210> SEQ ID NO 2
<211> LENGTH: 2914
<212> TYPE: DNA
<213> ORGANISM: Thalassiosira pseudonana
<220> FEATURE:
<221> NAME/KEY: misc_feature
<222> LOCATION: (274)..(274)
<223> OTHER INFORMATION: n is a, c, g, or t

```
<400> SEQUENCE: 2
cggagggcgc actggagagg ttcccggagg tttgatgtaa ttggaggttg ggtcaaatac     60
agattctgcc ctaacatttt ccggaaattg gcttcagttt gattcaagcg aggaggcgct    120
cggcaggagg gcccgtcacc tttttgcata tttgggactt caatggtttc tacatttttt    180
cctttctgga acccaaacgc tgtccttcaa ttctccttcc catactcacg gatggatccc    240
cgaaaatgcc accaccaatc acccttgtca atcncaaacc tcgtcatcct tcacattttc    300
ttagcaccat tggccggtgt acccttcccc gcgactgcca gtctatgggt cagtatatct    360
cccacatttg gagaggtatt gctaaaacgt gtcaatcata catatgataa ctggagagtg    420
cacacgaaga gatcaatgct tgagctagga gggtggctat tggctgtgag cggcagcttt    480
cacttaagat attacggcac ggcaagtcta ctcgacaata caaccgatgc tgcaggttta    540
tgcaatagct caagttgtat caacaacaaa acgtgcgaga atgacgacag tgcttacgaa    600
gatgatgcca tgagagctgt ttgggcattg ctatgggcgt tgcagctggg aacgttggtc    660
ggttgtgcgt tagtgttagg agtgcatcat ttcagtggag ataacctgac caaacaatct    720
gcgataccaa caaaatcttc aaaagcaaag ccaatatctg atcaaaaagc agctgtgaca    780
tccggcagta cctgcgctgt gagagagaag gcacgaaaag acggtctagt actcctcgat    840
ggcaactggt acaacgttga aaagttcgtc catcatcatc ctggaggtgt agaagtgttg    900
gagcagtatc tcggggcaga tatctcgttt gtgtttagag tgatgcatag aaatccaact    960
caaatcatga atatcgcaa gccggtacga gctgccaccc cagaagaact tgaggctctc   1020
acaagccgcc gtcaagaggt ttgtcttgat atgatggacg actttgttac caattccatt   1080
gatatcgctt ctccagaaat gcttcccaag ccaacgcagt ttgacctgaa gtcatttgag   1140
aaggacttca ttgacttata tgaagagttt gttgctcagg gatacttcaa gccctcaaca   1200
acatggctac tctggaacac agcggtactg attagtatca tcgcgttatc tgtcatctca   1260
atgaaagtgc taccaccaac ttcgtttgtc ctacctggag cattgcttgg tctcttttgg   1320
caccaaagtg gattcctcat gcacgatgcc gagcaccata atttggctgg aaacgaacgg   1380
ctgaatgaca ttttgggttg gatctatggc actgtcttct gggtgtcaa tggcgcttgg   1440
tggagagagg agcatagaga acatcatgct ttcctcaaca cttacgatga tgaaagtggt   1500
ttcaaagatc cccaggtgtg tcagcgtcac tgtagacgac ttcaaagtta cttgttcctc   1560
tcgttgctca cacattcgat tttattcatt cactcacaga tgagagagga cgtctggata   1620
cagaacaaga agttgattcc gttcttcggt gacgagatca ttcatttctt aacaaacttt   1680
cagcacattc tgttccttcc gatcatcttt atcgttggcc gcgttggtat tgtcgtagat   1740
tctacactga ctgagaggaa gttccgtcct tggagtaagt gtcaattggt attcattgag   1800
aaggaactgc tgatttgact ttcatactaa ctaactgcat cgccacttca tcacgacgat   1860
agcaatactt ggtaatgttt gtcatatcct actacactac gcaatcttat ctcagacgag   1920
tcgtcctatc cccgtgtaca tcatcggctc tcttggcaa gctattctct ctttgcaatt   1980
gcttgggaat cactacgtca agccttggaa tagactcaac gatgccacag agggaaactt   2040
ctgcgtttgg cagatactaa gcactcaaga cttgcatgt ccacgttggt ctcggtggct   2100
gtacggaggt ctcaacttc actattccca tcatctattc ccaacgttgt ctagagagta   2160
ctttcacatt acatcaccac gcattcgggt gagtgctcgt gtttagtgtt gctacattca   2220
tatcaatgat actcatagct ccatttcttt cgacagagac tatgtgagaa gcacgggctt   2280
ccgtttattg agattgcgtt cattgattgc gttgttggaa tggtcaacaa ctttaacgaa   2340
```

```
gtgaggaaag acttcgctac gaaaggccac gggagtgtgg ctttcatgta cacgtgatct    2400
taagtgtcga gacgatatag aggttgatat ttactgtttt gtcaccagta gttcgtctaa    2460
tatgatgtag caaccgcagc ttgtggaatt agtttagtgt actatgtaac tgaaaaagtt    2520
acgtcgatct actctctgca catctacatc gtgtgaagcc attccgttca agaagtatcc    2580
taatccctcg aaccaaacag tctcgtccta tacccatcat taatcagccg cctctacccg    2640
atgttgctgt tgttgcggct gctgctgaac cccctcgccg cccgataatg gcgaagggca    2700
gtcggacact tgataatctt cttcacagag tttatgagct gggtgtttgt accaatacct    2760
cctttatatg gtactaatgg acccgtgtcc attattgctt ggccgcgttt ccaccgtttg    2820
gaccgatagg tggccaaagg cccacacaga agagcaccat aaaggcgcag ccttgaggaa    2880
actcaagaaa ccccgatggt ccacgtatta aaac                                2914

<210> SEQ ID NO 3
<211> LENGTH: 1551
<212> TYPE: DNA
<213> ORGANISM: Thalassiosira pseudonana

<400> SEQUENCE: 3
atggctagag ctgtttgggc attgctatgg gcgttgcagc tgggaacgtt ggtcggttgt      60
gcgttagtgt taggagtgca tcatttcagt ggagataacc tgaccaaaca atctgcgata     120
ccaacaaaat cttcaaaagc aaagccaata tctgatcaaa aagcagctgt gacatccggc     180
agtacctgcg ctgtgagaga gaaggcacga aaagacggtc tagtactcct cgatggcaac     240
tggtacaacg ttgaaaagtt cgtccatcat catcctggag gtgtagaagt gttggagcag     300
tacctcgggg cagatatctc gtttgtgttt agagtgatgc atagaaatcc aactcaaatc     360
atgaaatatc gcaagccggt acgagctgcc accccagaag aacttgaggc tctcacaagc     420
cgccgtcaag aggtttgtct tgatatgatg gacgactttg ttaccaattc cattgatatc     480
gcttctccag aaatgcttcc caagccaacg cagtttgacc tgaagtcatt tgagaaggac     540
ttcattgact tatatgaaga gtttgttgct cagggatact tcaagccctc aacaacatgg     600
ctactctgga cacagcggt actgattagt atcatcgcgt tatctgtcat ctcaatgaaa     660
gtgctaccac caacttcgtt tgtcctacct ggagcattgc ttggtctctt ttggcaccaa     720
agtggattcc tcatgcacga tgccgagcac cataatttgg ctggaaacga acggctgaat     780
gacattttgg gttggatcta tggcactgtc ttcttgggtg tcaatggcgc ttggtggaga     840
gaggagcata gagaacatca tgcttttcctc aacacttacg atgatgaaag tggtttcaaa     900
gatccccaga tgagagagga cgtctggata cagaacaaga agttgattcc gttcttcggt     960
gacgagatca ttcatttctt aacaaacttt cagcacattc tgttccttcc gatcatcttt    1020
atcgttggcc gcgttggtat tgtcgtagat tctacactga ctgagaggaa gttccgtcct    1080
tggacaatac ttggtaatgt ttgtcatatc ctactacact acgcaatctt atctcagacg    1140
agtcgtccta tccccgtgta catcatcggc tctctttggc aagctattct ctctttgcaa    1200
ttgcttggga atcactacgt caagccttgg aatagactca acgatgccac agagggaaac    1260
ttctgcgttt ggcagatact aagcactcaa gactttgcat gtccacgttg gtctcggtgg    1320
ctgtacggag gtctcaactt tcactattcc catcatctgt tcccaacgtt gtctagagag    1380
tactttcaca ttcatcacc acgcattcgg agactatgtg agaagcacgg gcttccgttt    1440
attgagattc gtttattga ttgcgttgtt ggaatggtca caactttaa cgaagtgagg    1500 aaagacttcg ctacgaaagg ccacgggagt gtggctttca tgtacacgtg a              1551
```

-continued

```
<210> SEQ ID NO 4
<211> LENGTH: 516
<212> TYPE: PRT
<213> ORGANISM: Thalassiosira pseudonana

<400> SEQUENCE: 4

Met Ala Arg Ala Val Trp Ala Leu Leu Trp Ala Leu Gln Leu Gly Thr
1               5                   10                  15

Leu Val Gly Cys Ala Leu Val Leu Gly Val His His Phe Ser Gly Asp
            20                  25                  30

Asn Leu Thr Lys Gln Ser Ala Ile Pro Thr Lys Ser Ser Lys Ala Lys
        35                  40                  45

Pro Ile Ser Asp Gln Lys Ala Ala Val Thr Ser Gly Ser Thr Cys Ala
    50                  55                  60

Val Arg Glu Lys Ala Arg Lys Asp Gly Leu Val Leu Leu Asp Gly Asn
65                  70                  75                  80

Trp Tyr Asn Val Glu Lys Phe Val His His Pro Gly Gly Val Glu
                85                  90                  95

Val Leu Glu Gln Tyr Leu Gly Ala Asp Ile Ser Phe Val Phe Arg Val
            100                 105                 110

Met His Arg Asn Pro Thr Gln Ile Met Lys Tyr Arg Lys Pro Val Arg
        115                 120                 125

Ala Ala Thr Pro Glu Glu Leu Glu Ala Leu Thr Ser Arg Arg Gln Glu
    130                 135                 140

Val Cys Leu Asp Met Met Asp Asp Phe Val Thr Asn Ser Ile Asp Ile
145                 150                 155                 160

Ala Ser Pro Glu Met Leu Pro Lys Pro Thr Gln Phe Asp Leu Lys Ser
                165                 170                 175

Phe Glu Lys Asp Phe Ile Asp Leu Tyr Glu Gly Phe Val Ala Gln Gly
            180                 185                 190

Tyr Phe Lys Pro Ser Thr Thr Trp Leu Leu Trp Asn Thr Ala Val Leu
        195                 200                 205

Ile Ser Ile Ile Ala Leu Ser Val Ile Ser Met Lys Val Leu Pro Pro
    210                 215                 220

Thr Ser Phe Val Leu Pro Gly Ala Leu Leu Gly Leu Phe Trp His Gln
225                 230                 235                 240

Ser Gly Phe Leu Met His Asp Ala Glu His His Asn Leu Ala Gly Asn
                245                 250                 255

Glu Arg Leu Asn Asp Ile Leu Gly Trp Ile Tyr Gly Thr Val Phe Leu
            260                 265                 270

Gly Val Asn Gly Ala Trp Trp Arg Glu Glu His Arg Glu His His Ala
        275                 280                 285

Phe Leu Asn Thr Tyr Asp Asp Glu Ser Gly Phe Lys Asp Pro Gln Met
    290                 295                 300

Arg Glu Asp Val Trp Ile Gln Asn Lys Lys Leu Ile Pro Phe Phe Gly
305                 310                 315                 320

Asp Glu Ile Ile His Phe Leu Thr Asn Phe Gln His Ile Leu Phe Leu
                325                 330                 335

Pro Ile Ile Phe Ile Val Gly Arg Val Gly Ile Val Val Asp Ser Thr
            340                 345                 350

Leu Thr Glu Arg Lys Phe Arg Pro Trp Thr Ile Leu Gly Asn Val Cys
        355                 360                 365

His Ile Leu Leu His Tyr Ala Ile Leu Ser Gln Thr Ser Arg Pro Ile
    370                 375                 380
```

Pro Val Tyr Ile Ile Gly Ser Leu Trp Gln Ala Ile Leu Ser Leu Gln
385                 390                 395                 400

Leu Leu Gly Asn His Tyr Val Lys Pro Trp Asn Arg Leu Asn Asp Ala
            405                 410                 415

Thr Glu Gly Asn Phe Cys Val Trp Gln Ile Leu Ser Thr Gln Asp Phe
        420                 425                 430

Ala Cys Pro Arg Trp Ser Arg Trp Leu Tyr Gly Gly Leu Asn Phe His
    435                 440                 445

Tyr Ser His His Leu Phe Pro Thr Leu Ser Arg Glu Tyr Phe His Ile
    450                 455                 460

Thr Ser Pro Arg Ile Arg Arg Leu Cys Glu Lys His Gly Leu Pro Phe
465                 470                 475                 480

Ile Glu Ile Ala Phe Ile Asp Cys Val Val Gly Met Val Asn Asn Phe
                485                 490                 495

Asn Glu Val Arg Lys Asp Phe Ala Thr Lys Gly His Gly Ser Val Ala
                500                 505                 510

Phe Met Tyr Thr
        515

<210> SEQ ID NO 5
<211> LENGTH: 1900
<212> TYPE: DNA
<213> ORGANISM: Thalassiosira pseudonana
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
<223> OTHER INFORMATION: n is a, c, g, or t

<400> SEQUENCE: 5
nanccatatg cgggaatacg gccagggtat acccacagcg cctccgttgc agcaaactcc      60
tatccaatac ctccccatga accccccctt cggccaccct atatgcgaga ctcgttcgtc    120
tggacctgca gatgatgact ggtgaggcca aattagttgg gaatgcgtgc agatggaggc    180
cttattcttt tgcaatcagg ggcgtcgtca agaggagatc catgttgttg tgtgattcga    240
cttgcttggg gcgtgcatga tgtgtgcgtg cgtgtacgat gttgataggt agaaagagat    300
cgaggcggtg attcaactat tcaggatact gaaagagttg atatagcagc agtaatatat    360
cctagttgtt tgtgtttgtg ttgtggtgta tcaagtattc aatgacgcaa caataacgtt    420
ggtagtgtat gggtgaacag gtgttcggga caaaggcttt tcataaaatc tatttaacgt    480
gttcgttaaa acgacgaaaa gaagccactc tgcaccattc cagcgcagac aagaccagca    540
ggcacagaac agcacgacac accgacccga gccgaaaaag ccaacaacaa cgacaccgac    600
ccgagccgat acagccgaca ggcaaaggct ctctgctaca atctacaaaa cggcaacatc    660
aaatcatgcc accctccatc aaagacacac tcgacgagcc cttcgtctcg cccgcatcca    720
ccaagtcgcc caccaccaaa cccctcctcc cccgccgcaa accctcaaa cgatactccc     780
cctcccaaat ctcccaacac aacactccca ccgatgcatg gctcatttac aaatcccaag    840
tccttgacat ttccaaatgg atatcgcacc atccaggtgg agagcagacg ctgttgaggt    900
ttgccggtat ggatgctacc gatgaattga gggcatttca tgatgattgg gttttggagg    960
agaagttgcc tcattttgtg attggggagg tggattggac tactaccggc ggggcagaga   1020
atactgtcac gaaggatgga caggtttcgg agcttatcaa ggatttcaga gagttgggtg   1080
aacacttcga caggttgggg tactttcacg tcagtccatg gtattacgtc cgtaaggtgg   1140

-continued

```
ctaccgtctt cgccatcttt ggatgtgcac tcggactcct cttcaatacc gattccatcc    1200
cagcacacat gctcgcggcg gtactcctcg gtatattctg gcaacaattt gcattcgtcg    1260
gacatgactg tggtcacatg tcggcgcgga ctcatgcccg tgatcatatc gatgtaccta    1320
agctgggagc actggtgacc ttcttcaatg ggatttcggt agcgtggtgg aaggctacgc    1380
acaatgttca tcatgctgtg ccaaatagtg ttgattgtga cccggacatt gctcatttgc    1440
cggtgtttgc gttgcatgag cacatgttta cgtcgttgtt taacaagtat catgggaggg    1500
tgatggagtt tgattggctg cgcgtaatg tctttgtgcc atttcaacac ttttggtact    1560
atcccataat ggcggtggcg aggttcaatc tgtacattca atcagcattg tttttggcgt    1620
cgaagaacga tgggcatgca ggaagaaggg gatcctctag attggatttg ctggcgttca    1680
atcgtgttct tctgttggtt agcggtgctg gtgtcatgca tcccgagctg gcggagcgt    1740 atcgcattcg tcttcgtcag acatgctgta cctgggttac tgcatgtgca atcacctgtc    1800
gccttctctt ggacaatctt gatcccacaa gaggacccgg ttggggtgct ctttccgaag    1860
cccggttctg ggcttttgcc acattggcgt cccgggtcca                         1900
```

<210> SEQ ID NO 6
<211> LENGTH: 411
<212> TYPE: PRT
<213> ORGANISM: Thalassiosira pseudonana

<400> SEQUENCE: 6

```
Met Pro Pro Ser Ile Lys Asp Thr Leu Asp Glu Pro Phe Val Ser Pro
1               5                   10                  15

Ala Ser Thr Lys Ser Pro Thr Thr Lys Pro Leu Leu Pro Arg Arg Lys
                20                  25                  30

Pro Leu Lys Arg Tyr Ser Pro Ser Gln Ile Ser Gln His Asn Thr Pro
            35                  40                  45

Thr Asp Ala Trp Leu Ile Tyr Lys Ser Gln Val Leu Asp Ile Ser Lys
        50                  55                  60

Trp Ile Ser His His Pro Gly Gly Glu Gln Thr Leu Leu Arg Phe Ala
65                  70                  75                  80

Gly Met Asp Ala Thr Asp Glu Leu Arg Ala Phe His Asp Asp Trp Val
                85                  90                  95

Leu Glu Glu Lys Leu Pro His Phe Val Ile Gly Glu Val Asp Trp Thr
            100                 105                 110

Thr Thr Gly Gly Ala Glu Asn Thr Val Thr Lys Asp Gly Gln Val Ser
        115                 120                 125

Glu Leu Ile Lys Asp Phe Arg Glu Leu Gly Glu His Phe Asp Arg Leu
    130                 135                 140

Gly Tyr Phe His Val Ser Pro Trp Tyr Tyr Val Arg Lys Val Ala Thr
145                 150                 155                 160

Val Phe Ala Ile Phe Gly Cys Ala Leu Gly Leu Leu Phe Asn Thr Asp
                165                 170                 175

Ser Ile Pro Ala His Met Leu Ala Ala Val Leu Leu Gly Ile Phe Trp
            180                 185                 190

Gln Gln Phe Ala Phe Val Gly His Asp Cys Gly His Met Ser Ala Arg
        195                 200                 205

Thr His Ala Arg Asp His Ile Asp Val Pro Lys Leu Gly Ala Leu Val
    210                 215                 220

Thr Phe Phe Asn Gly Ile Ser Val Ala Trp Trp Lys Ala Thr His Asn
225                 230                 235                 240
```

-continued

```
Val His His Ala Val Pro Asn Ser Val Asp Cys Asp Pro Asp Ile Ala
                245                 250                 255

His Leu Pro Val Phe Ala Leu His Glu His Met Phe Thr Ser Leu Phe
            260                 265                 270

Asn Lys Tyr His Gly Arg Val Met Glu Phe Asp Trp Leu Ala Arg Asn
        275                 280                 285

Val Phe Val Pro Phe Gln His Phe Trp Tyr Tyr Pro Ile Met Ala Val
    290                 295                 300

Ala Arg Phe Asn Leu Tyr Ile Gln Ser Ala Leu Phe Leu Ala Ser Lys
305                 310                 315                 320

Asn Asp Gly His Ala Gly Arg Arg Gly Ser Ser Arg Leu Asp Leu Leu
                325                 330                 335

Ala Phe Asn Arg Val Leu Leu Leu Val Ser Gly Ala Gly Val Met His
            340                 345                 350

Pro Glu Leu Gly Gly Ala Tyr Arg Ile Arg Leu Arg Gln Thr Cys Cys
        355                 360                 365

Thr Trp Val Thr Ala Cys Ala Ile Thr Cys Arg Leu Leu Leu Asp Asn
    370                 375                 380

Leu Asp Pro Thr Arg Gly Pro Gly Trp Gly Ala Leu Ser Glu Ala Arg
385                 390                 395                 400

Phe Trp Ala Phe Ala Thr Leu Ala Ser Arg Val
                405                 410
```

<210> SEQ ID NO 7
<211> LENGTH: 1913
<212> TYPE: DNA
<213> ORGANISM: Thalassiosira pseudonana
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (1800)..(1800)
<223> OTHER INFORMATION: n is a, c, g, or t

<400> SEQUENCE: 7

```
canctaaccg ggaagagggc cttatttgcc accacagtga taaccttcgg ctgtgaccac      60
gggagcagcc gtggcgagcc cgcgtctgac cagccctgtc tttttggagc atccctcacc     120
acacatcgca tctcgttgca cggggatcag tgcacagtct tcgtctcatt gttagatgta     180
cacgcgaaga agcacatcca gcccgactct tcataacatc tcaggaccct gcaaacacgc     240
atcacatcat gatgttccac cgagtcgtca tcggcatcgc cctcacaatg ggctgtgtct     300
ccagtttctc ctcgcccggt cattcaatat tggcacgtcc tatgcaatca tccaccactt     360
ctcgtttctc gacaatgatt gaaaagtcag agatttctga cagtgtcaac aacgaaaaca     420
aggagatgac atcatcttct gaaatgccta ctgcgtggga atgcaatgag gaagctgagt     480
gcgtggaagt tcctgcttgt gatgacgagg aatgccgtac tactttggat gtgaggattc     540
atggcaaatg gtacgatctt tcaggtgagt gcaagttgtg gtatgcattg ttataagttc     600
tattctgtat cggcacacac gatattgtgt tgtgatcaat gttctaacag ccatttgttc     660
ctcctacttc ctcaggatgg cgcaaagctc accctgcagg accccactgg atcgactggt     720
acgacggtcg tgacgccacc gaagtcatgg acgcatttca cacccaaaaa ggacgtgaaa     780
tgtacaagcg tcttcccgcg tctgcccccg aaacggctgc cgttcttgaa gcatctgcag     840
caccttactc gcagacggag cttaacttta ggaagttgag ggatcaattg aaagtgaggg     900
ggtggtggga gagggacttt gtccatgagg gaaagttgct ggcgatttgg gcatcgttgg     960
```

```
ttacaggagc agcattgact gcggagagtg ctcctcctct ttcaactttc ttgttgggat    1020
tgtctatgac gaatgctgga tggttggggc atgattatat tcatggtgtt gataagttca    1080
gtcaagttat gaggcctttt gctgccgtgg ctgctggttt gggaccaact tggtggagtg    1140
ataagcacaa caagcatcac gctttgagtg agtctgactc ttgttgttac tgcaagtgtg    1200
gtttaaagat tgaatcaata ccatcgtact catatcctca acattctttc aatcgcaaca    1260
gccaacgaaa tgggagttga tgaagacatt gcgaccgatc catttctctt tccttatgtc    1320
ccggatccaa agtacgattc tccacttcgt aagatccaac actacatctt ctacagtccc    1380
ttctccttcc tctttgccct ctggcgcgtg acacccctta aggtcgccgt agactcagtt    1440
gaatcgaaac gtcccgatgc aaagaatgaa ttgtggtatc tcttggcaca ttacttcgtc    1500
ttgttgacct tcttcccagc tcaggtgtgg gtgcctgctg tcttcctctc tggcctcatg    1560
tctgcactca ttgttactcc gacacatcag tcggaagagt attttgagga gtatcagcct    1620
gattgggtga cggctcagtt tgagagcacg agaaatgctg tcacgactaa tccattctct    1680
gagtggcttt ggggaggaat gcaataccag ttggagcatc acttgttccc ttccatgccc    1740
aggtaagcag cttaatgttt gtatcttgta ccattgttga cttctcgttc tcggctaacn    1800
ctgttggaag cgtatgagcc tagcacataa tggtgtgtat gcgaccatga actcgattta    1860
aggttcaaat accttactat catctcagtc cggtgccgga tgacgtgtgt ccc           1913

<210> SEQ ID NO 8
<211> LENGTH: 389
<212> TYPE: PRT
<213> ORGANISM: Thalassiosira pseudonana

<400> SEQUENCE: 8

Gln Pro Phe Val Pro Pro Thr Ser Ser Gly Trp Arg Lys Ala His Pro
1               5                   10                  15

Ala Gly Pro His Trp Ile Asp Trp Tyr Asp Gly Arg Asp Ala Thr Glu
            20                  25                  30

Val Met Asp Ala Phe His Thr Gln Lys Gly Arg Glu Met Tyr Lys Arg
        35                  40                  45

Leu Pro Ala Ser Ala Pro Glu Thr Ala Ala Val Leu Glu Ala Ser Ala
    50                  55                  60

Ala Pro Tyr Ser Gln Thr Glu Leu Asn Phe Arg Lys Leu Arg Asp Gln
65                  70                  75                  80

Leu Glu Ser Glu Gly Trp Trp Glu Arg Asp Phe Val His Glu Gly Lys
                85                  90                  95

Leu Leu Ala Ile Trp Ala Ser Leu Val Thr Gly Ala Ala Leu Thr Ala
            100                 105                 110

Glu Ser Ala Pro Pro Leu Ser Thr Phe Leu Leu Gly Leu Ser Met Thr
        115                 120                 125

Asn Ala Gly Trp Leu Gly His Asp Tyr Ile His Gly Val Asp Lys Phe
    130                 135                 140

Ser Gln Val Met Arg Pro Phe Ala Ala Val Ala Ala Gly Leu Gly Pro
145                 150                 155                 160

Thr Trp Trp Ser Asp Lys His Asn Lys His His Ala Leu Ser Glu Ser
                165                 170                 175

Asp Ser Cys Cys Tyr Cys Lys Cys Gly Leu Lys Ile Glu Ser Ile Pro
            180                 185                 190

Ser Tyr Ser Tyr Pro Gln His Ser Phe Asn Arg Asn Ser Gln Arg Asn
        195                 200                 205
```

-continued

```
Gly Ser Arg Leu Asn Gln Tyr His Arg Thr His Ile Leu Asn Ile Leu
            210                 215                 220

Ser Ile Ala Thr Ala Asn Glu Met Gly Val Asp Glu Asp Ile Ala Thr
225                 230                 235                 240

Asp Pro Phe Leu Phe Pro Tyr Val Pro Asp Pro Lys Tyr Asp Ser Pro
                245                 250                 255

Leu Arg Lys Ile Gln His Tyr Ile Phe Tyr Ser Pro Phe Ser Phe Leu
                260                 265                 270

Phe Ala Leu Trp Arg Val Asp Thr Leu Lys Val Ala Val Asp Ser Val
            275                 280                 285

Glu Ser Lys Arg Pro Asp Ala Lys Asn Glu Leu Trp Tyr Leu Leu Ala
290                 295                 300

His Tyr Phe Val Leu Leu Thr Phe Phe Pro Ala Gln Val Trp Val Pro
305                 310                 315                 320

Ala Val Phe Leu Ser Gly Leu Met Ser Ala Leu Ile Val Thr Pro Thr
                325                 330                 335

His Gln Ser Glu Glu Tyr Phe Glu Glu Tyr Gln Pro Asp Trp Val Thr
                340                 345                 350

Ala Gln Phe Glu Ser Thr Arg Asn Ala Val Thr Thr Asn Pro Phe Ser
            355                 360                 365

Glu Trp Leu Trp Gly Gly Met Gln Tyr Gln Leu Glu His His Leu Phe
370                 375                 380

Pro Ser Met Pro Arg
385

<210> SEQ ID NO 9
<211> LENGTH: 2689
<212> TYPE: DNA
<213> ORGANISM: Thalassiosira pseudonana
<220> FEATURE:
<221> NAME/KEY: misc_feature
<222> LOCATION: (14)..(17)
<223> OTHER INFORMATION: n is a, c, g, or t
<220> FEATURE:
<221> NAME/KEY: misc_feature
<222> LOCATION: (2687)..(2687)
<223> OTHER INFORMATION: n is a, c, g, or t
<220> FEATURE:
<221> NAME/KEY: misc_feature
<222> LOCATION: (2689)..(2689)
<223> OTHER INFORMATION: n is a, c, g, or t

<400> SEQUENCE: 9
aaaaaaaaaa aaannnnggg aagcgagatc aatcgagctg gtaccatgag tttcaaaagt    60
caacttcaac attcaagttg tacaaagag agggcctcag acgtggtgag caaaagcact    120
tcacagggga atagtagggg aaaaacagaa atatttggca aatttatctt agttcctgat    180
tatatcttca attactaaag ggaaaacaat gcagctcaaa agctacgttt gtgtacttct    240
ttgaaaccac ctcaccccg cggcttcgcg tccgggtcgg cccgcttgca tcctttcttc    300
ctctcacaat ttatcatcca acgagctgat aacgtgtcat tcacagggt caacacaata    360 aaacatacta atcaaccatg ggaaaggag gagacgcagc cgcagccacc aagcgtagtg    420
gagcattgaa attggcggag aagccgcaga agtacacctg caggaggtg aagaagcacg    480 tgagtctccg cttgtgttgc tgccgttgga tgtccttgtc gttggttcgg attatgcaac    540
gagagttcgt attgcaactc aatttcaatt gtccatctgc aatcaactca tctgacccaa    600
caacttctgc caccgtccac ccattcagat cacccccgac gatgcctggg tagtccacca    660
aaacaaagtc tacgacgtct ccaactggta cgaccacccc ggtggagccg tggtgttcac    720
```

```
ccacgccgga gacgacatga cggacatctt cgccgccttc cacgcccaag gctctcaggc    780
catgatgaag aagttttaca ttggagattt gattccggag agtgtggagc ataaggatca    840
aagacagttg gatttcgaga agggatatcg tgatttacgg gccaagcttg tcatgatggg    900
gatgttcaag tcgagtaaga tgtattatgc atacaagtgc tcgttcaata tgtgcatgtg    960
gttggtggcg gtggccatgg tgtactactc ggacagtttg gcaatgcaca ttggatcggc   1020
tctcttgttg ggattgttct ggcagcagtg tggatggctt cgcacgact ttcttcacca   1080 ccaagtcttt aagcaacgaa agtacggaga tctcgttggc atcttttggg gagatctcat   1140
gcaggggttc tcgatgcagt ggtggaagaa caagcacaat ggccaccatg ctgttcccaa   1200
cttgcacaac tcttccttgg acagtcagga tggtgatccc gatattgata ccatgccact   1260
ccttgcttgg agtctcaagc aggctcagag tttcagagag atcaataagg gaaaggacag   1320
taccttcgtc aagtacgcta tcaaattcca ggcattcaca tacttcccca tcctcctctt   1380
ggctcgcatc tcttggttga atgaatcctt caaaactgca ttcggactcg agctgcctc   1440 ggagaatgcc aagttggagt tggagaagcg tggacttcag tacccacttt tggagaagct   1500
tggaatcacc cttcattaca cttggatgtt cgtcctctct tccggatttg aaggtggtc   1560 tcttccatat tccatcatgt atttcttcac tgccacatgc tcctcgggac ttttcctcgc   1620
attggtcttt ggattgggac acaacggtat gtcagtgtac gatgccacca cccgacctga   1680
cttctggcaa ctccaagtca ccactacacg taacatcatt ggtggacacg gcattcccca   1740
attctttgtg gattggttct gcggtggatt gcaataccaa gtggatcacc acctcttccc   1800
catgatgcct agaaacaata tcgcgaaatg ccacaagctt gtggagtcat tctgtaagga   1860
gtggggtgtg aagtaccatg aggccgatat gtgggatggt accgtggaag tgttgcaaca   1920
tctctccaag gtgtcggatg atttccttgt ggagatggtg aaggatttcc ctgccatgta   1980
aacacctatt accagtcggc agctttgtcg gttgctggag atgaatgatg cgaactcatc   2040
gtaaatactc attattaatg aacaatgtta ccctgcagtc gtgaggtttg ccttcgttgt   2100
cccacccctt ctattgtgta ttggtgatca ttgaaacgag atagtctatt tctacatcag   2160
atctctccat tcaccctcga atagtatccc aacaaccatc acatcaaact acttgaatct   2220
cctctgtggc aatccctccc attgtacatt tactctcaaa ggtatatcta tttgtccctt   2280
tattaattgt tgaatattga aggggaagat tccatttccc cctctctctt ccccgatgat   2340
cctctcacct ctaaatacct ttcacaacac aacaacgaaa caacgcagat cagacaaaca   2400
acatggcaga actatcctca ccgtgcaaac gatccaaagg cgaagagcta ttcctagtcc   2460
atctccaacg catgtctggc tccagaccct catcctgaag agtgagttgt gatgtcgctg   2520
atgtactttc cgtcttgatg ttctctgagg tgtcacaact cagggtcacc aaagcagctt   2580
cgctgatcgc tagtggcgag aagatccgat ttcccatccc gaagaaagcc tcctgggaaa   2640
aatgtcactt cttgaaagtc gagggtgacg aataattggg ggcggangn             2689
```

<210> SEQ ID NO 10
<211> LENGTH: 1458
<212> TYPE: PRT
<213> ORGANISM: Thalassiosira pseudonana

<400> SEQUENCE: 10

Ala Thr Gly Gly Cys Thr Gly Gly Ala Ala Ala Gly Gly Ala Gly
1               5                   10                  15

Gly Ala Gly Ala Cys Gly Cys Ala Gly Cys Cys Gly Cys Ala Gly Cys
            20                  25                  30

-continued

```
Thr Ala Cys Cys Ala Ala Gly Cys Gly Thr Ala Gly Thr Gly Gly Ala
        35                  40                  45

Gly Cys Ala Thr Thr Gly Ala Ala Ala Thr Thr Gly Gly Cys Gly Gly
    50                  55                  60

Ala Gly Ala Ala Gly Cys Cys Gly Cys Ala Gly Ala Ala Gly Thr Ala
65                  70                  75                  80

Cys Ala Cys Thr Thr Gly Gly Cys Ala Gly Gly Ala Gly Gly Thr Gly
                85                  90                  95

Ala Ala Gly Ala Ala Gly Cys Ala Cys Ala Thr Cys Ala Cys Cys Cys
            100                 105                 110

Cys Cys Gly Ala Cys Gly Ala Thr Gly Cys Cys Thr Gly Gly Gly Thr
        115                 120                 125

Ala Gly Thr Cys Cys Ala Cys Cys Ala Ala Ala Ala Cys Ala Ala Ala
    130                 135                 140

Gly Thr Cys Thr Ala Cys Gly Ala Cys Gly Thr Cys Thr Cys Cys Ala
145                 150                 155                 160

Ala Cys Thr Gly Gly Thr Ala Cys Gly Ala Cys Cys Ala Cys Cys Cys
                165                 170                 175

Cys Gly Gly Thr Gly Gly Ala Gly Cys Cys Gly Thr Gly Gly Thr Gly
            180                 185                 190

Thr Thr Cys Ala Cys Cys Cys Ala Cys Gly Cys Cys Gly Gly Ala Gly
        195                 200                 205

Ala Cys Gly Ala Cys Ala Thr Gly Ala Cys Gly Gly Ala Cys Ala Thr
    210                 215                 220

Cys Thr Thr Cys Gly Cys Cys Gly Cys Cys Thr Thr Cys Cys Ala Cys
225                 230                 235                 240

Gly Cys Cys Cys Ala Ala Gly Gly Cys Thr Cys Thr Cys Ala Gly Gly
                245                 250                 255

Cys Cys Ala Thr Gly Ala Thr Gly Ala Ala Gly Ala Ala Gly Thr Thr
            260                 265                 270

Thr Thr Ala Cys Ala Thr Thr Gly Gly Ala Gly Ala Thr Thr Thr Gly
        275                 280                 285

Ala Thr Thr Cys Cys Gly Gly Ala Gly Ala Gly Thr Gly Thr Gly Gly
    290                 295                 300

Ala Gly Cys Ala Thr Ala Ala Gly Gly Ala Thr Cys Ala Ala Ala Gly
305                 310                 315                 320

Ala Cys Ala Gly Thr Thr Gly Gly Ala Thr Thr Thr Cys Gly Ala Gly
                325                 330                 335

Ala Ala Gly Gly Ala Thr Ala Thr Cys Gly Thr Gly Ala Thr Thr
            340                 345                 350

Thr Ala Cys Gly Gly Gly Cys Cys Ala Ala Gly Cys Thr Thr Gly Thr
        355                 360                 365

Cys Ala Thr Gly Ala Thr Gly Gly Gly Gly Ala Thr Gly Thr Thr Cys
    370                 375                 380

Ala Ala Gly Thr Cys Gly Ala Gly Thr Ala Ala Gly Ala Thr Gly Thr
385                 390                 395                 400

Ala Thr Thr Ala Thr Gly Cys Ala Thr Ala Cys Ala Ala Gly Thr Gly
                405                 410                 415

Cys Thr Cys Gly Thr Thr Cys Ala Ala Thr Ala Thr Gly Thr Gly Cys
            420                 425                 430

Ala Thr Gly Thr Gly Gly Thr Thr Gly Gly Thr Gly Gly Cys Gly Gly
        435                 440                 445

Thr Gly Gly Cys Cys Ala Thr Gly Gly Thr Gly Thr Ala Cys Thr Ala
    450                 455                 460
```

-continued

```
Cys Thr Cys Gly Gly Ala Cys Ala Gly Thr Thr Gly Gly Cys Ala
465                 470                 475                 480

Ala Thr Gly Cys Ala Cys Ala Thr Thr Gly Ala Thr Cys Gly Gly
                485                 490                 495

Cys Thr Cys Thr Cys Thr Thr Gly Thr Thr Gly Gly Gly Ala Thr
                500                 505                 510

Gly Thr Thr Cys Thr Gly Gly Cys Ala Gly Cys Ala Gly Thr Gly
                515                 520                 525         Thr

Gly Gly Ala Thr Gly Gly Cys Thr Thr Gly Cys Gly Cys Ala Cys Gly
530                 535                 540

Ala Cys Thr Thr Thr Cys Thr Thr Cys Ala Cys Cys Ala Cys Cys Ala
545                 550                 555                 560

Ala Gly Thr Cys Thr Thr Thr Ala Ala Gly Cys Ala Ala Cys Gly Ala
                565                 570                 575

Ala Ala Gly Thr Ala Cys Gly Gly Ala Gly Ala Thr Cys Thr Cys Gly
                580                 585                 590

Thr Thr Gly Gly Cys Ala Thr Cys Thr Thr Thr Gly Gly Gly Gly
                595                 600                 605

Ala Gly Ala Thr Cys Thr Cys Ala Thr Gly Cys Ala Gly Gly Gly
610                 615                 620

Thr Thr Cys Thr Cys Gly Ala Thr Gly Cys Ala Gly Thr Gly Gly Thr
625                 630                 635                 640

Gly Gly Ala Ala Gly Ala Ala Cys Ala Ala Gly Cys Ala Cys Ala Ala
                645                 650                 655

Thr Gly Gly Cys Cys Ala Cys Cys Ala Thr Gly Cys Thr Gly Thr Thr
                660                 665                 670

Cys Cys Cys Ala Ala Cys Thr Thr Gly Cys Ala Cys Ala Ala Cys Thr
                675                 680                 685

Cys Thr Thr Cys Cys Thr Thr Gly Gly Ala Cys Ala Gly Thr Cys Ala
                690                 695                 700

Gly Gly Ala Thr Gly Gly Thr Gly Ala Thr Cys Cys Cys Gly Ala Thr
705                 710                 715                 720

Ala Thr Thr Gly Ala Thr Ala Cys Cys Ala Thr Gly Cys Cys Ala Cys
                725                 730                 735

Thr Cys Cys Thr Thr Gly Cys Thr Thr Gly Gly Ala Gly Thr Cys Thr
                740                 745                 750

Cys Ala Ala Gly Cys Ala Gly Gly Cys Thr Cys Ala Gly Ala Gly Thr
                755                 760                 765

Thr Thr Cys Ala Gly Ala Gly Ala Gly Ala Thr Cys Ala Ala Thr Ala
                770                 775                 780

Ala Gly Gly Gly Ala Ala Ala Gly Gly Ala Cys Ala Gly Thr Ala Cys
785                 790                 795                 800

Cys Thr Thr Cys Gly Thr Cys Ala Ala Gly Thr Ala Cys Gly Cys Thr
                805                 810                 815

Ala Thr Cys Ala Ala Thr Thr Cys Cys Ala Gly Gly Cys Ala Thr
                820                 825                 830

Thr Cys Ala Cys Ala Thr Ala Cys Thr Cys Cys Cys Ala Thr
                835                 840                 845

Cys Cys Thr Cys Thr Cys Thr Thr Gly Gly Cys Thr Cys Gly Cys
                850                 855                 860

Ala Thr Cys Thr Cys Thr Thr Gly Gly Thr Thr Gly Ala Ala Thr Gly
865                 870                 875                 880

Ala Ala Thr Cys Cys Thr Thr Cys Ala Ala Ala Ala Cys Thr Gly Cys
                885                 890                 895
```

-continued

```
Ala Thr Thr Cys Gly Gly Ala Cys Thr Cys Gly Gly Ala Cys Thr
                900                 905                 910
Gly Cys Cys Thr Cys Gly Gly Ala Gly Ala Ala Thr Gly Cys Cys Ala
            915                 920                 925
Ala Gly Thr Thr Gly Gly Ala Gly Thr Thr Gly Gly Ala Gly Ala Ala
        930                 935                 940
Gly Cys Gly Thr Gly Gly Ala Cys Thr Thr Cys Ala Gly Thr Ala Cys
945                 950                 955                 960
Cys Cys Ala Cys Thr Thr Thr Gly Gly Ala Gly Ala Ala Gly Cys
                965                 970                 975
Thr Thr Gly Gly Ala Ala Thr Cys Ala Cys Cys Thr Thr Cys Ala
            980                 985                 990
Cys Thr Ala Cys Ala Cys Thr Thr Gly Gly Ala Thr Gly Thr Thr Cys
        995                 1000                1005
Gly Thr Cys Cys Thr Cys Thr Cys Thr Thr Cys Cys Gly Gly Ala
    1010                1015                1020
Thr Thr Thr Gly Gly Ala Ala Gly Gly Thr Gly Gly Thr Cys Thr
        1025                1030                1035
Cys Thr Thr Cys Cys Ala Thr Ala Thr Thr Cys Cys Ala Thr Cys
    1040                1045                1050
Ala Thr Gly Thr Ala Thr Thr Cys Thr Thr Cys Ala Cys Thr
    1055                1060                1065
Gly Cys Cys Ala Cys Ala Thr Gly Cys Thr Cys Cys Thr Cys Gly
    1070                1075                1080
Gly Gly Ala Cys Thr Thr Thr Cys Cys Thr Cys Gly Cys Ala
    1085                1090                1095
Thr Thr Gly Gly Thr Cys Thr Thr Thr Gly Gly Ala Thr Thr Gly
    1100                1105                1110
Gly Gly Ala Cys Ala Cys Ala Ala Cys Gly Gly Thr Ala Thr Gly
    1115                1120                1125
Thr Cys Ala Gly Thr Gly Thr Ala Cys Gly Ala Thr Gly Cys Cys
    1130                1135                1140
Ala Cys Cys Ala Cys Cys Gly Ala Cys Cys Thr Gly Ala Cys
    1145                1150                1155
Thr Thr Cys Thr Gly Gly Cys Ala Ala Cys Thr Cys Cys Ala Ala
    1160                1165                1170
Gly Thr Cys Ala Cys Ala Cys Thr Ala Cys Ala Cys Gly Thr
    1175                1180                1185
Ala Ala Cys Ala Thr Cys Ala Thr Thr Gly Gly Thr Gly Gly Ala
    1190                1195                1200
Cys Ala Cys Gly Gly Cys Ala Thr Thr Cys Cys Cys Ala Ala
    1205                1210                1215
Thr Thr Cys Thr Thr Thr Gly Thr Gly Gly Ala Thr Thr Gly Gly
    1220                1225                1230
Thr Thr Cys Thr Gly Cys Gly Gly Thr Gly Gly Ala Thr Thr Gly
    1235                1240                1245
Cys Ala Ala Thr Ala Cys Cys Ala Ala Gly Thr Gly Gly Ala Thr
    1250                1255                1260
Cys Ala Cys Cys Ala Cys Thr Cys Thr Thr Cys Cys Cys Cys
    1265                1270                1275
Ala Thr Gly Ala Thr Gly Cys Cys Thr Ala Gly Ala Ala Ala Cys
    1280                1285                1290
Ala Ala Thr Ala Thr Cys Gly Cys Gly Ala Ala Gly Thr Gly Cys
    1295                1300                1305
```

-continued

```
Cys Ala  Cys Ala Ala Gly Cys Thr Thr Gly Thr Gly Gly Ala Gly
    1310             1315                1320

Thr Cys  Ala Thr Thr Cys Thr Gly Thr Ala Ala Gly Gly Ala Gly
    1325             1330                1335

Thr Gly  Gly Gly Gly Thr Gly Thr Gly Ala Ala Gly Thr Ala Cys
    1340             1345                1350

Cys Ala  Thr Gly Ala Gly Cys Thr Gly Ala Thr Ala Thr Gly
    1355             1360                1365

Thr Gly  Gly Gly Ala Thr Gly Thr Ala Cys Cys Gly Thr Gly
    1370             1375                1380

Gly Ala  Ala Gly Thr Gly Thr Thr Gly Cys Ala Ala Cys Ala Thr
    1385             1390                1395

Cys Thr  Cys Thr Cys Cys Ala Ala Gly Gly Thr Gly Thr Cys Gly
    1400             1405                1410

Gly Ala  Thr Gly Ala Thr Thr Cys Cys Thr Thr Gly Thr Gly
    1415             1420                1425

Gly Ala  Gly Ala Thr Gly Gly Thr Gly Ala Ala Gly Gly Ala Thr
    1430             1435                1440

Thr Thr  Cys Cys Cys Thr Gly Cys Cys Ala Thr Gly Thr Ala Ala
    1445             1450                1455
```

```
<210> SEQ ID NO 11
<211> LENGTH: 485
<212> TYPE: PRT
<213> ORGANISM: Thalassiosira pseudonana

<400> SEQUENCE: 11
```

```
Met Ala Gly Lys Gly Gly Asp Ala Ala Ala Thr Lys Arg Ser Gly
1               5                   10                  15

Ala Leu Lys Leu Ala Glu Lys Pro Gln Lys Tyr Thr Trp Gln Glu Val
            20                  25                  30

Lys Lys His Ile Thr Pro Asp Asp Ala Trp Val Val His Gln Asn Lys
        35                  40                  45

Val Tyr Asp Val Ser Asn Trp Tyr Asp His Pro Gly Gly Ala Val Val
    50                  55                  60

Phe Thr His Ala Gly Asp Asp Met Thr Asp Ile Phe Ala Ala Phe His
65                  70                  75                  80

Ala Gln Gly Ser Gln Ala Met Met Lys Lys Phe Tyr Ile Gly Asp Leu
                85                  90                  95

Ile Pro Glu Ser Val Glu His Asp Gln Arg Gln Leu Asp Phe Glu
            100                 105                 110

Lys Gly Tyr Arg Asp Leu Arg Ala Lys Leu Val Met Met Gly Met Phe
        115                 120                 125

Lys Ser Ser Lys Met Tyr Tyr Ala Tyr Lys Cys Ser Phe Asn Met Cys
    130                 135                 140

Met Trp Leu Val Ala Val Ala Met Val Tyr Tyr Ser Asp Ser Leu Ala
145                 150                 155                 160

Met His Ile Gly Ser Ala Leu Leu Gly Leu Phe Trp Gln Gln Cys
                165                 170                 175

Gly Trp Leu Ala His Asp Phe Leu His His Gln Val Phe Lys Gln Arg
            180                 185                 190

Lys Tyr Gly Asp Leu Val Gly Ile Phe Trp Gly Asp Leu Met Gln Gly
        195                 200                 205

Phe Ser Met Gln Trp Trp Lys Asn Lys His Asn Gly His His Ala Val
    210                 215                 220
```

```
Pro Asn Leu His Asn Ser Ser Leu Asp Ser Gln Asp Gly Asp Pro Asp
225                 230                 235                 240

Ile Asp Thr Met Pro Leu Leu Ala Trp Ser Leu Lys Gln Ala Gln Ser
            245                 250                 255

Phe Arg Glu Ile Asn Lys Gly Lys Asp Ser Thr Phe Val Lys Tyr Ala
        260                 265                 270

Ile Lys Phe Gln Ala Phe Thr Tyr Phe Pro Ile Leu Leu Leu Ala Arg
    275                 280                 285

Ile Ser Trp Leu Asn Glu Ser Phe Lys Thr Ala Phe Gly Leu Gly Ala
290                 295                 300

Ala Ser Glu Asn Ala Lys Leu Glu Leu Gly Lys Arg Gly Leu Gln Tyr
305                 310                 315                 320

Pro Leu Leu Glu Lys Leu Gly Ile Thr Leu His Tyr Thr Trp Met Phe
                325                 330                 335

Val Leu Ser Ser Gly Phe Gly Arg Trp Ser Leu Pro Tyr Ser Ile Met
            340                 345                 350

Tyr Phe Phe Thr Ala Thr Cys Ser Ser Gly Leu Phe Leu Ala Leu Val
        355                 360                 365

Phe Gly Leu Gly His Asn Gly Met Ser Val Tyr Asp Ala Thr Thr Arg
    370                 375                 380

Pro Asp Phe Trp Gln Leu Gln Val Thr Thr Thr Arg Asn Ile Ile Gly
385                 390                 395                 400

Gly His Gly Ile Pro Gln Phe Phe Val Asp Trp Phe Cys Gly Gly Leu
                405                 410                 415

Gln Tyr Gln Val Asp His His Leu Phe Pro Met Met Pro Arg Asn Asn
            420                 425                 430

Ile Ala Lys Cys His Lys Leu Val Glu Ser Phe Cys Lys Glu Trp Gly
        435                 440                 445

Val Lys Tyr His Glu Ala Asp Met Trp Asp Gly Thr Val Glu Val Leu
    450                 455                 460

Gln His Leu Ser Lys Val Ser Asp Asp Phe Leu Val Glu Met Val Lys
465                 470                 475                 480

Asp Phe Pro Ala Met
                485

<210> SEQ ID NO 12
<211> LENGTH: 2775
<212> TYPE: DNA
<213> ORGANISM: Thalassiosira pseudonana
<220> FEATURE:
<221> NAME/KEY: misc_feature
<222> LOCATION: (2530)..(2530)
<223> OTHER INFORMATION: n is a, c, g, or t
<220> FEATURE:
<221> NAME/KEY: misc_feature
<222> LOCATION: (2743)..(2743)
<223> OTHER INFORMATION: n is a, c, g, or t

<400> SEQUENCE: 12
tatgtccacc ccccctggt tgtccacct ctgtcttcga tcttgggacc cgggtctcga      60
gtttgcgaga cctctcaagc gggcccatag tagacgactt gatctgtttg ctgatacctg   120
acgtgcaccg attttcggg gctaacgcca cttttcgtaa ctccaccagg tacgactgac   180
ttgtgcccgt agatatctct gatacctcta tggcaaagcc gatcaaatcg aaatgattgt   240
actgtagcaa ggataagcag atggataggc ggggatcttc catgtcgaca agaggaagag   300
agagagtatg tcgtcggcga gggtggatag gttgagagag aggggatgac agattgtaca   360
ttatcttccc tccaagactt taccaaggca cgtcactctg attagaatct tacatacacg   420
```

```
tggagtaata gtggacaata aatgacaagt gaagcacccc agtggaccat ttcgtcgcca    480
cgtggtcgtc cgctgtgggt tgagtgaacc gacgacgacg aacacaaccg ctgaatctcc    540
ttcggcaaca acaatacacc aatatgtgca acggcaacct cccagcatcc accgcacagc    600
tcaagtccac ctcgaagccc cagcagcaac atgagcatcg caccatctcc aagtccgagc    660
tcgcccaaca caacacgccc aaatcagcat ggtgtgccgt ccactccact cccgccaccg    720
acccatccca ctccaacaac aaacaacacg cacacctagt cctcgacatt accgactttg    780
cgtcccgcca tccaggggga gacctcatcc tcctcgcttc cggcaaagac gcctcggtgc    840
tgtttgaaac ataccatcca cgtggagttc cgacgtctct cattcaaaag ctgcagattg    900
gagtgatgga ggaggaggcg tttcgggatt cgttttacag ttggactgat tctgactttt    960
atactgtgtt gaagaggagg gttgtggagc ggttggagga gaggggttg gcgaggaggg   1020 gatcgaaaga gatttggatc aaggctttgt tcttgttggt tggattttgg tactgtttgt   1080
acaagatgta tactacgtcg gatattgatc agtacggtat tgccattgcc tattctattg   1140
gaatgggaac ctttgcggca ttcatcggca cgtgtattca acacgatgga aatcacggtg   1200
cattcgctca gaacaagtta ctcaacaagt tggctgggtg gacgttggat atgattggtg   1260
cgagtgcgtt tacgtgggag cttcagcaca tgctggggca tcatccatat acgaatgtgt   1320
tggatggggt ggaggaggag aggaaggaga gggggagga tgttgctttg gaagaaaagg    1380
atcaggtgag acgagatgac agagagagag agagtctatt cgtgtgaagt cgtagatgca   1440
tgtgtgcgat tgagcgacac aactctaacg cattgcattc cactttcaac tcgccgacag   1500
gaatcagatc cagacgtatt ctcctccttc cctctcatga gaatgcatcc cctccataca   1560
acctcatggt atcataaata ccaacaccte tacgctccac ccctctttgc attgatgaca   1620
cttgccaaag tattccaaca ggattttgaa gttgccacat ccggacgatt atatcatatt   1680
gatgccaatg tacgttatgg ttcggtatgg aatgtcatga ggttttgggc tatgaaggtc   1740
attacgatgg gatatatgat gggattacca atctactttc atggagtact gaggggagtt   1800
ggattgtttg ttattgggca tttgcgtgt ggagagttgt tggcgacgat gtttattgtg   1860
aatcacgtca ttgagggtgt gagttatgga acgaaggatt tggttggtgg tgcgagtcat   1920
gtagatgaga agaagattgt caagccaacg actgtattgg gagatacacc aatggaaaag   1980
actcgcgagg aggcattgaa aagcaacagc aataacaaca agaagaaggg agagaagaac   2040
tcggtaccat ccgttccatt caacgactgg gcagcagtcc aatgccagac ctccgtgaat   2100
tggtctccag gctcatggtt ctggaatcac ttttctgggg gactctctca tcagattgag   2160
catcacttgt tccccagcat ttgtcataca aactactgtc atatccagga tgttgtggag   2220
agtacgtgtg ctgagtacgg agttccgtat cagagtgaga gtaatttgtt tgttgcttat   2280
ggaaagatga ttagtcattt gaagttttg ggtaaagcca agtgtgagta ggtgttaggt   2340
attgagaggt gtcgagttgt ctcattcttt aaaaataagc gctgaaagtg atttcgaaaa   2400
acaaggtttg tcaataccag tctcttgtat tgattgctgc gtcgacacat ctccgtgagg   2460
agtttgacct cactcattct aacttggaat gtctcttttg cgctggtgag cttggacgaa   2520
tacactccgn cagaagagac tgcattggta atgcagagga aagaggatat actgtatgag   2580
tccgaagaat cgatgacgcg cggtgaggtg gtgtacatca cttgtgagga ccaacgtgga   2640
accgcatgtc tgaagaggtc catacctaaa catttgagcg gtcttgggag caaactttag   2700
cagagattga atgctccatt cggtatttgt tcttctgtgc canttgata aggaacagca   2760 accaacacac cgggg                                                    2775
```

<210> SEQ ID NO 13
<211> LENGTH: 564
<212> TYPE: PRT
<213> ORGANISM: Thalassiosira pseudonana

<400> SEQUENCE: 13

```
Met Cys Asn Gly Asn Leu Pro Ala Ser Thr Ala Gln Leu Lys Ser Thr
1               5                   10                  15

Ser Lys Pro Gln Gln Gln His Glu His Arg Thr Ile Ser Lys Ser Glu
            20                  25                  30

Leu Ala Gln His Asn Thr Pro Lys Ser Ala Trp Cys Ala Val His Ser
        35                  40                  45

Thr Pro Ala Thr Asp Pro Ser His Ser Asn Asn Lys Gln His Ala His
    50                  55                  60

Leu Val Leu Asp Ile Thr Asp Phe Ala Ser Arg His Pro Gly Gly Asp
65                  70                  75                  80

Leu Ile Leu Leu Ala Ser Gly Lys Asp Ala Ser Val Leu Phe Glu Thr
                85                  90                  95

Tyr His Pro Arg Gly Val Pro Thr Ser Leu Ile Gln Lys Leu Gln Ile
            100                 105                 110

Gly Val Met Glu Glu Ala Phe Arg Asp Ser Phe Tyr Ser Trp Thr
        115                 120                 125

Asp Ser Asp Phe Tyr Thr Val Leu Lys Arg Arg Val Val Glu Arg Leu
130                 135                 140

Glu Glu Arg Gly Leu Ala Arg Arg Gly Ser Lys Glu Ile Trp Ile Lys
145                 150                 155                 160

Ala Leu Phe Leu Leu Val Gly Phe Trp Tyr Cys Leu Tyr Lys Met Tyr
                165                 170                 175

Thr Thr Ser Asp Ile Asp Gln Tyr Gly Ile Ala Ile Ala Tyr Ser Ile
            180                 185                 190

Gly Met Gly Thr Phe Ala Ala Phe Ile Gly Thr Cys Ile Gln His Asp
        195                 200                 205

Gly Asn His Gly Ala Phe Ala Gln Asn Lys Leu Leu Asn Lys Leu Ala
    210                 215                 220

Gly Trp Thr Leu Asp Met Ile Gly Ala Ser Ala Phe Thr Trp Glu Leu
225                 230                 235                 240

Gln His Met Leu Gly His His Pro Tyr Thr Asn Val Leu Asp Gly Val
                245                 250                 255

Glu Glu Glu Arg Lys Glu Arg Gly Glu Asp Val Ala Leu Glu Glu Lys
            260                 265                 270

Asp Gln Val Arg Arg Asp Arg Glu Arg Glu Ser Leu Phe Val Gln
        275                 280                 285

Glu Ser Asp Pro Asp Val Phe Ser Ser Phe Pro Leu Met Arg Met His
    290                 295                 300

Pro Leu His Thr Thr Ser Trp Tyr His Lys Tyr Gln His Leu Tyr Ala
305                 310                 315                 320

Pro Pro Leu Phe Ala Leu Met Thr Leu Ala Lys Val Phe Gln Gln Asp
                325                 330                 335

Phe Glu Val Ala Thr Ser Gly Arg Leu Tyr His Ile Asp Ala Asn Val
            340                 345                 350

Arg Tyr Gly Ser Val Trp Asn Val Met Arg Phe Trp Ala Met Lys Val
        355                 360                 365

Ile Thr Met Gly Tyr Met Met Gly Leu Pro Ile Tyr Phe His Gly Val
    370                 375                 380
```

```
Leu Arg Gly Val Gly Leu Phe Val Ile Gly His Leu Ala Cys Gly Glu
385                 390                 395                 400

Leu Leu Ala Thr Met Phe Ile Val Asn His Val Ile Glu Gly Val Ser
            405                 410                 415

Tyr Gly Thr Lys Asp Leu Val Gly Gly Ala Ser His Val Asp Glu Lys
        420                 425                 430

Lys Ile Val Lys Pro Thr Thr Val Leu Gly Asp Thr Pro Met Glu Lys
    435                 440                 445

Thr Arg Glu Glu Ala Leu Lys Ser Asn Ser Asn Asn Asn Lys Lys Lys
450                 455                 460

Gly Glu Lys Asn Ser Val Pro Ser Val Pro Phe Asn Asp Trp Ala Ala
465                 470                 475                 480

Val Gln Cys Gln Thr Ser Val Asn Trp Ser Pro Gly Ser Trp Phe Trp
            485                 490                 495

Asn His Phe Ser Gly Leu Ser His Gln Ile Glu His His Leu Phe
            500                 505                 510

Pro Ser Ile Cys His Thr Asn Tyr Cys His Ile Gln Asp Val Val Glu
    515                 520                 525

Ser Thr Cys Ala Glu Tyr Gly Val Pro Tyr Gln Ser Glu Ser Asn Leu
530                 535                 540

Phe Val Ala Tyr Gly Lys Met Ile Ser His Leu Lys Phe Leu Gly Lys
545                 550                 555                 560

Ala Lys Cys Glu

<210> SEQ ID NO 14
<211> LENGTH: 1434
<212> TYPE: DNA
<213> ORGANISM: Thalassiosira pseudonana

<400> SEQUENCE: 14
atggactttc tctccggcga tcctttccgg acactcgtcc ttgcagcact tgttgtcatc      60
ggatttgctg cggcgtggca atgcttctac ccgccgagca tcgtcggcaa gcctcgtaca     120
ttaagcaatg gtaaactcaa taccagaatc catggcaaat tgtacgacct tcatcgtttt     180
cagcatccag gaggccccgt ggctcttttct cttgttcaag gtcgcgacgg aacagctcta    240
tttgagtcac accatccctt catacctcga agaatctact tcagatcct ctccaagtac      300 gaggttccgt cgactgaaga ctctgtttcc ttcatcgcca ccctagacga actcaatggt     360
gaatctccgt acgattggaa ggacattgaa aatgatgatt tcgtatctga cctacgagct     420
ctcgtaattg agcactttc tcctctcgcc aaggaaaggg gagtttcact cgttgagtcg     480
tcgaaggcaa cacctcagcg gtggatggtg gttctactgc tccttgcgtc gttcttcctc     540
agcatcccat tatatttgag tggttcgtgg actttcgttg tcgtcactcc catcctcgct     600
tggctggcgg ttgtcaatta ctggcacgat gctactcact tgcattgag cagcaactgg    660 attttgaatg ctgcgctccc atatctcctc cctctcctat cgagtccgtc aatgtggtat     720
catcatcacg tcattggaca tcacgcatac accaacattt ccaaaagaga tccagatctt     780
gctcacgctc cacaactcat gagagaacac aagagtatca aatggagacc atctcactta     840
aatcaaacac agcttccgcg gattctcttc atctggtcga ttgcagtcgg tattgggttg     900
aacttactga acgacgtgag agcactaacc aagctttcat acaacaacgt tgttcgggtg     960
gagaagatgt catcgtcgcg aacattactc catttccttg gacgtatgtt gcacatcttt    1020
gtgactacac tttgggccctt tttggcgttt ccggtgtgga aggccatcgt ttgggcgact    1080
gtaccgaatg ccatactgag tttgtgcttc atgctgaata cgcaaatcaa tcacctcatc    1140
```

-continued

| | |
|---|---|
| aacacgtgtg cacatgcttc cgataacaac ttttacaagc atcaagttgt aactgctcag | 1200 |
| aactttggcc gatcaagtgc cttttgcttc atcttctcgg gaggtctcaa ctaccaaatt | 1260 |
| gaacatcatt tgttgccgac ggtgaaccat tgccatttgc cagctttggc cccgggtgta | 1320 |
| gagcgtttgt gtaagaaaca cggggtgaca tacaactctg ttgaaggata cagagaggcc | 1380 |
| atcattgcac actttgcaca taccaaagat atgtcgacga agcctactga ttga | 1434 |

```
<210> SEQ ID NO 15
<211> LENGTH: 2906
<212> TYPE: DNA
<213> ORGANISM: Thalassiosira pseudonana
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (2645)..(2645)
<223> OTHER INFORMATION: n is a, c, g, or t
<220> FEATURE:
<221> NAME/KEY: misc_feature
<222> LOCATION: (2650)..(2650)
<223> OTHER INFORMATION: n is a, c, g, or t
<220> FEATURE:
<221> NAME/KEY: misc_feature
<222> LOCATION: (2655)..(2655)
<223> OTHER INFORMATION: n is a, c, g, or t

<400> SEQUENCE: 15
```

| | |
|---|---|
| anntctccca cccngccagc tctttcaggt cgaccggaga tacacacttc ttcccaccaa | 60 |
| cttcgtcctc catacgatcg gaagaaaaga ggagattatc ttgacttctt gacggaggag | 120 |
| tgggatgaaa agaacttgag tgggtaaggg ctgattttcc tgagaaggag aagtcagctg | 180 |
| gaacgaagtt catggagttt tgtggcaacc ctattgagac gttgcttggt ggaggaaggt | 240 |
| agcgaggttg agcatgcaaa cagaatggta taaatcacta agatgtcact cccaatgaca | 300 |
| agtaggaata gcaatgacga gatggtgtac agatgttaga gatggagaga ttaagcgaat | 360 |
| ggctggatga ttaggatatg caatgcaaaa ctgtatagat tcttgctaat agactttgta | 420 |
| gacaacgtcc gtctgcagaa aaggacaata ctaattaata taaaaccgac tcggagagaa | 480 |
| catgacatgg caagttgtca ctatggaatt cactacgtcg cttgacagga agctcacgtg | 540 |
| gcctcggcga agaagacaaa caaaaccgag ccctcacatt tcactctgta cagttcatag | 600 |
| tcaacaccac caatacgatg ccccccaacg ccgatatctc ccgcatccgc aaccgcatcc | 660 |
| ccaccaaaac aggtaccgtt gcctctgccg acaacaacga ccccgccacc caatccgtcc | 720 |
| gaaccctcaa atctctcaag ggcaacgagg tcgtcatcaa cggcacaatt tatgacattg | 780 |
| ctgactttgt ccatcctgga ggagaggttg tcaagttctt tggtgggaat gatgttacta | 840 |
| ttcagtataa tatgattcat ccgtatcata cggggaaaca tctggagaag atgaaggctg | 900 |
| ttggaaaggt tgtagattgg cagtcggagt gagtttgaat ggtgcacacg ttgacgttgt | 960 |
| tgttgtgtca tttcgttctt tgcatttgat atccaactga cctctacaca cctcttcgtt | 1020 |
| accatagcta caagttcgac accccctttg aacgagagat caaatcagaa gtgttcaaga | 1080 |
| tcgtacgtcg cgggcgtgag ttcggcacaa caggctactt cctccgtgcc tttttctaca | 1140 |
| tcgctctctt cttcaccatg caatacactt tcgccacatg caccaccttc accacctacg | 1200 |
| atcactggta tcagagtggt gtattcatcg caattgtgtt tggtatttca caggcattca | 1260 |

```
ttgggttgaa tgtccagcac gatgccaatc acggagctgc cagtaagcgt ccctgggtga    1320
atgacttgtt gggatttgga acggatttga ttggatctaa caaatggaat tggatggcac    1380
agcattggac tcatcacgct tacactaacc atagtgagaa ggatcccgat agcttcagct    1440
cggaacctat gtttgcattc aatgactatc ccattggaca cccgaagaga aagtggtggc    1500
ataggttcca gggagggtac ttcctcttca tgcttggact ttactggctc tcgactgtat    1560
tcaatccgca attcattgat cttcgtcaac gtggggctca gtacgtcgga attcaaatgg    1620
agaatgattt cattgtcaag aggaggaagt acgccgttgc attgaggatg atgtacattt    1680
acttgaacat tgtcagcccc ttcatgaaca atggtttgag ctggtctacc tttggaatca    1740
tcatgttgat gggaatcagc gagagtctca ctctcagtgt gctcttctcg ttgtctcaca    1800
acttcatcaa ttcggatcgt gatcctacgg ctgacttcaa aaagaccgga gaacaagtgt    1860
gctggttcaa gtcgcaggtg gagacttcgt ctacctatgg gggttttatt tccggatgtc    1920
ttacgggagg actcaacttt caggtggaac atcatctctt tccccgtatg agcagtgctt    1980
ggtatcctta cattgcacct acggttcgtg aggtttgcaa gaagcacggg gtgaactacg    2040
cttattatcc ttggattggg cagaatttgg tatcaacatt caaatacatg catcgcgctg    2100
gtagtggagc caactgggag ctcaagccgt tgtctggaag tgcctaaagt ttagttgtac    2160
tgattgtcgg aggtgctgct ggtgcttcaa ctaatgttag gagtgcatgt taaaagcctt    2220 cttttgtgttt tgttgtcttc gtattcagta tatcagtttc gatatgttgc attgtaacct    2280
cctccacttg cactcaaaac aaatctagca taacatttct catcccgagt catgtcatga    2340
acgactcatt acgcaatgcc tctctcataa ccccgaaaca actcgaccag cttcatactc    2400
taatcgtcca tctttggcag ctgcaatcca gccctagcag cagctctctt actcaactcc    2460
atcggactca acttcgtatc tgcccccgca tcaatctcat gcaaccgtgc cctctctacc    2520
aaatctgcct ttaacatcca gtaatcatag gcgattccac gtagtacgtt tgctcgctcg    2580
ggagacactg atgccgatgc tttgtattgt gatatactgt gctggtgcgc gcatcgatgc    2640
tccgntgtgn gttgngactg tgcattggat gctgctgtga acagtcggt gcagtgtagc     2700 ggaggtgctg tttctgaact gaggagatgc ccgcaaactg ataggggtg gtgcagcgct     2760 ataaattttg cgagcgagtc cattgtcctt gctctcccca tatgtcgggc gagggcgaag    2820
cgcgaaggag aagccacaag gccaatacaa cagaaagttt aaatgaagga cgtaattcct    2880
acacagtcca gtggcgaagt tacaac                                         2906
```

<210> SEQ ID NO 16
<211> LENGTH: 1434
<212> TYPE: DNA
<213> ORGANISM: Thalassiosira pseudonana

<400> SEQUENCE: 16

```
atggctcccc ccaacgccga tatctcccgc atccgcaacc gcatccccac caaaacaggt      60
accgttgcct ctgccgacaa caacgacccc gccacccaat ccgtccgaac cctcaaatct     120
ctcaagggca acgaggtcgt catcaacggc acaatttatg acattgctga ctttgtccat     180
cctggaggag aggttgtcaa gttctttggt gggaatgatg ttactattca gtataatatg     240
attcatccgt atcatacggg gaaacatctg gagaagatga aggctgttgg aaaggttgta     300
gattggcagt cggactacaa gttcgacacc ccctttgaac gagagatcaa atcagaagtg     360
ttcaagatcg tacgtcgcgg gcgtgagttc ggcacaacag gctacttcct ccgtgccttt     420
ttctacatcg ctctcttctt caccatgcaa tacactttcg ccacatgcac caccttcacc     480
```

-continued

```
acctacgatc actggtatca gagtggtgta ttcatcgcaa ttgtgtttgg tatttcacag    540
gcattcattg ggttgaatgt ccagcacgat gccaatcacg gagctgccag taagcgtccc    600
tgggtgaatg acttgttggg atttggaacg gatttgattg gatctaacaa atggaattgg    660
atggcacagc attggactca tcacgcttac actaaccata gtgagaagga tcccgatagc    720
ttcagctcgg aacctatgtt tgcattcaat gactatccca ttggacaccc gaagagaaag    780
tggtggcata ggttccaggg agggtacttc ctcttcatgc ttggacttta ctggctcccg    840
actgtattca atccgcaatt cattgatctt cgtcaacgtg gggctcagta cgtcggaatt    900
caaatggaga atgatttcat tgtcaagagg aggaagtacg ccgttgcatt gaggatgatg    960
tacatttact tgaacattgt cagccccttc atgaacaatg gtttgagctg gtctaccttt   1020
ggaatcatca tgttgatggg aatcagcgag agtctcactc tcagtgtgct cttctcgttg   1080
tctcacaact tcatcaattc ggatcgtgat cctacggctg acttcaaaaa gaccggagaa   1140
caagtgtgct ggttcaagtc gcaggtggag acttcgtcta cctatggggg ttttatttcc   1200
ggatgtctta cggaggact caactttcag gtggaacatc atctctttcc ccgtatgagc   1260
agtgcttggt atccttacat tgcacctacg gttcgtgagg tttgcaagaa gcacgggatg   1320
agctacgctt attatccttg gattgggcag aatttggtat caacattcaa atacatgcat   1380
cgcgctggta gtggagccaa ctgggagctc aagccgttgt ctggaagtgc ctaa          1434
```

<210> SEQ ID NO 17
<211> LENGTH: 477
<212> TYPE: PRT
<213> ORGANISM: Thalassiosira pseudonana

<400> SEQUENCE: 17

```
Met Ala Pro Pro Asn Ala Asp Ile Ser Arg Ile Arg Asn Arg Ile Pro
1               5                   10                  15

Thr Lys Thr Gly Thr Val Ala Ser Ala Asp Asn Asn Asp Pro Ala Thr
            20                  25                  30

Gln Ser Val Arg Thr Leu Lys Ser Leu Lys Gly Asn Glu Val Val Ile
        35                  40                  45

Asn Gly Thr Ile Tyr Asp Ile Ala Asp Phe Val His Pro Gly Gly Glu
    50                  55                  60

Val Val Lys Phe Phe Gly Gly Asn Asp Val Thr Ile Gln Tyr Asn Met
65                  70                  75                  80

Ile His Pro Tyr His Thr Gly Lys His Leu Glu Lys Met Lys Ala Val
                85                  90                  95

Gly Lys Val Val Asp Trp Gln Ser Asp Tyr Lys Phe Asp Thr Pro Phe
            100                 105                 110

Glu Arg Glu Ile Lys Ser Glu Val Phe Lys Ile Val Arg Arg Gly Arg
        115                 120                 125

Glu Phe Gly Thr Thr Gly Tyr Phe Leu Arg Ala Phe Phe Tyr Ile Ala
    130                 135                 140

Leu Phe Phe Thr Met Gln Tyr Thr Phe Ala Thr Cys Thr Thr Phe Thr
145                 150                 155                 160

Thr Tyr Asp His Trp Tyr Gln Ser Gly Val Phe Ile Ala Ile Val Phe
                165                 170                 175

Gly Ile Ser Gln Ala Phe Ile Gly Leu Asn Val Gln His Asp Ala Asn
            180                 185                 190

His Gly Ala Ala Ser Lys Arg Pro Trp Val Asn Asp Leu Leu Gly Phe
        195                 200                 205
```

-continued

```
Gly Thr Asp Leu Ile Gly Ser Asn Lys Trp Asn Trp Met Ala Gln His
        210                 215                 220
Trp Thr His His Ala Tyr Thr Asn His Ser Glu Lys Asp Pro Asp Ser
225                 230                 235                 240
Phe Ser Ser Glu Pro Met Phe Ala Phe Asn Asp Tyr Pro Ile Gly His
            245                 250                 255
Pro Lys Arg Lys Trp Trp His Arg Phe Gln Gly Gly Tyr Phe Leu Phe
                260                 265                 270
Met Leu Gly Leu Tyr Trp Leu Pro Thr Val Phe Asn Pro Gln Phe Ile
            275                 280                 285
Asp Leu Arg Gln Arg Gly Ala Gln Tyr Val Gly Ile Gln Met Glu Asn
        290                 295                 300
Asp Phe Ile Val Lys Arg Arg Lys Tyr Ala Val Ala Leu Arg Met Met
305                 310                 315                 320
Tyr Ile Tyr Leu Asn Ile Val Ser Pro Phe Met Asn Asn Gly Leu Ser
                325                 330                 335
Trp Ser Thr Phe Gly Ile Ile Met Leu Met Gly Ile Ser Glu Ser Leu
            340                 345                 350
Thr Leu Ser Val Leu Phe Ser Leu Ser His Asn Phe Ile Asn Ser Asp
        355                 360                 365
Arg Asp Pro Thr Ala Asp Phe Lys Lys Thr Gly Glu Gln Val Cys Trp
    370                 375                 380
Phe Lys Ser Gln Val Glu Thr Ser Ser Thr Tyr Gly Gly Phe Ile Ser
385                 390                 395                 400
Gly Cys Leu Thr Gly Gly Leu Asn Phe Gln Val Glu His His Leu Phe
                405                 410                 415
Pro Arg Met Ser Ser Ala Trp Tyr Pro Tyr Ile Ala Pro Thr Val Arg
            420                 425                 430
Glu Val Cys Lys Lys His Gly Met Ser Tyr Ala Tyr Tyr Pro Trp Ile
        435                 440                 445
Gly Gln Asn Leu Val Ser Thr Phe Lys Tyr Met His Arg Ala Gly Ser
    450                 455                 460
Gly Ala Asn Trp Glu Leu Lys Pro Leu Ser Gly Ser Ala
465                 470                 475
```

<210> SEQ ID NO 18
<211> LENGTH: 1428
<212> TYPE: DNA
<213> ORGANISM: Thalassiosira pseudonana

<400> SEQUENCE: 18

```
atggctcccc ccaacgccga tatctcccgc atccgcaacc gcatccccac caaaacaggt      60
acctctgccg acaacaacga ccccgccacc caatccgtcc gaaccctcaa atctctcaag     120
ggcaacgagg tcgtcatcaa cggcacaatt tatgacattg ctgactttgt ccatcctgga     180
ggagaggttg tcaagttctt tggtgggaat gatgttacta ttcagtataa tatgattcat     240
ccgtatcata cggggaaaca tctggagaag atgaaggctg ttggaaaggt tgtagattgg     300
cagtcggact acaagttcga caccccctttt gaacgagaga tcaaatcaga agtgttcaag     360
atcgtacgtc gcgggcgtga gttcggcaca acaggctact cctccgtgc cttttttctac       420
atcgctctct tcttcaccat gcaatacact ttcgccacat gcaccacctt caccacctac     480
gatcactggt atcagagtgg tgtattcatc gcaattgtgt tggtatttc acaggcattc     540
attgggttga atgtccagca cgatgccaat cacgagctg ccagtaagcg tccctgggtg       600
aatgacttgt tgggatttgg aacggatttg attggatcta caaatggaa ttggatggca      660
```

```
cagcattgga ctcatcacgc ttacactaac catagtgaga aggatcccga tagcttcagc    720
tcggaaccta tgtttgcatt caatgactat cccattggac acccgaagag aaagtggtgg    780
cataggttcc agggagggta cttcctcttc atgcttggac tttactggct ctcgactgta    840
ttcaatccgc aattcattga tcttcgtcaa cgtggggctc agtacgtcgg aattcaaatg    900
gagaatgatt tcattgtcaa gaggaggaag tacgccgttg cattgaggat gatgtacatt    960
tacttgaaca ttgtcagccc cttcatgaac aatggtttga ctggtctac ctttggaatc    1020 atcatgttga tgggaatcag cgagagtctc actctcagtg tgctcttctc gttgtctcac    1080
aacctcatca attcggatcg tgatcctacg gctgacttca aaagaccgg agaacaagtg    1140 tgctggttca agtcgcaggt ggagacttcg tctacctatg ggggttttat ttccggatgt    1200
cttacgggag gactcaactt tcaggtggaa catcatctct ttccccgtat gagcagtgct    1260
tggtatcctt acattgcacc tacggttcgt gaggtttgca agaagcacgg ggtgaactac    1320
gcttattatc cttggattgg gcagaatttg gtatcaacat tcaaatacat gcatcgcgct    1380
ggtagtggag ccaactggga gctcaagccg ttgtctggaa gtgcctaa              1428

<210> SEQ ID NO 19
<211> LENGTH: 475
<212> TYPE: PRT
<213> ORGANISM: Thalassiosira pseudonana

<400> SEQUENCE: 19

Met Ala Pro Pro Asn Ala Asp Ile Ser Arg Ile Arg Asn Arg Ile Pro
1               5                   10                  15

Thr Lys Thr Gly Thr Ser Ala Asp Asn Asn Asp Pro Ala Thr Gln Ser
            20                  25                  30

Val Arg Thr Leu Lys Ser Leu Lys Gly Asn Glu Val Val Ile Asn Gly
        35                  40                  45

Thr Ile Tyr Asp Ile Ala Asp Phe Val His Pro Gly Gly Glu Val Val
    50                  55                  60

Lys Phe Phe Gly Gly Asn Asp Val Thr Ile Gln Tyr Asn Met Ile His
65                  70                  75                  80

Pro Tyr His Thr Gly Lys His Leu Glu Lys Met Lys Ala Val Gly Lys
                85                  90                  95

Val Val Asp Trp Gln Ser Asp Tyr Lys Phe Asp Thr Pro Phe Glu Arg
            100                 105                 110

Glu Ile Lys Ser Glu Val Phe Lys Ile Val Arg Arg Gly Arg Glu Phe
        115                 120                 125

Gly Thr Thr Gly Tyr Phe Leu Arg Ala Phe Phe Tyr Ile Ala Leu Phe
    130                 135                 140

Phe Thr Met Gln Tyr Thr Phe Ala Thr Cys Thr Thr Phe Thr Thr Tyr
145                 150                 155                 160

Asp His Trp Tyr Gln Ser Gly Val Phe Ile Ala Ile Val Phe Gly Ile
                165                 170                 175

Ser Gln Ala Phe Ile Gly Leu Asn Val Gln His Asp Ala Asn His Gly
            180                 185                 190

Ala Ala Ser Lys Arg Pro Trp Val Asn Asp Leu Leu Gly Phe Gly Thr
        195                 200                 205

Asp Leu Ile Gly Ser Asn Lys Trp Asn Trp Met Ala Gln His Trp Thr
    210                 215                 220

His His Ala Tyr Thr Asn His Ser Glu Lys Asp Pro Asp Ser Phe Ser
225                 230                 235                 240
```

Ser Glu Pro Met Phe Ala Phe Asn Asp Tyr Pro Ile Gly His Pro Lys
            245                 250                 255

Arg Lys Trp Trp His Arg Phe Gln Gly Gly Tyr Phe Leu Phe Met Leu
        260                 265                 270

Gly Leu Tyr Trp Leu Ser Thr Val Phe Asn Pro Gln Phe Ile Asp Leu
    275                 280                 285

Arg Gln Arg Gly Ala Gln Tyr Val Gly Ile Gln Met Glu Asn Asp Phe
290                 295                 300

Ile Val Lys Arg Arg Lys Tyr Ala Val Ala Leu Arg Met Met Tyr Ile
305                 310                 315                 320

Tyr Leu Asn Ile Val Ser Pro Phe Met Asn Asn Gly Leu Ser Trp Ser
                325                 330                 335

Thr Phe Gly Ile Ile Met Leu Met Gly Ile Ser Glu Ser Leu Thr Leu
            340                 345                 350

Ser Val Leu Phe Ser Leu Ser His Asn Leu Ile Asn Ser Asp Arg Asp
        355                 360                 365

Pro Thr Ala Asp Phe Lys Lys Thr Gly Glu Gln Val Cys Trp Phe Lys
    370                 375                 380

Ser Gln Val Glu Thr Ser Ser Tyr Gly Gly Phe Ile Ser Gly Cys
385                 390                 395                 400

Leu Thr Gly Gly Leu Asn Phe Gln Val Glu His His Leu Phe Pro Arg
                405                 410                 415

Met Ser Ser Ala Trp Tyr Pro Tyr Ile Ala Pro Thr Val Arg Glu Val
            420                 425                 430

Cys Lys Lys His Gly Val Asn Tyr Ala Tyr Tyr Pro Trp Ile Gly Gln
        435                 440                 445

Asn Leu Val Ser Thr Phe Lys Tyr Met His Arg Ala Gly Ser Gly Ala
    450                 455                 460

Asn Trp Glu Leu Lys Pro Leu Ser Gly Ser Ala
465                 470                 475

<210> SEQ ID NO 20
<211> LENGTH: 1485
<212> TYPE: DNA
<213> ORGANISM: Thalassiosira pseudonana

<400> SEQUENCE: 20
atggctccac cctccatcaa agacacactc gacgagccct cgtctcgcc cgcatccacc      60 aagtcgccca ccaccaaacc cctcctcccc cgccgcaaac ccctcaaacg atactccccc    120
tcccaaatct cccaacacaa cactcccacc gatgcatggc tcatttacaa atcccaagtc    180
cttgacattt ccaaatggat atcgcaccat ccaggtggag agcagacgct gttgaggttt    240
gccggtatgg atgctaccga tgaattgagg gcatttcatg atgattgggt tttggaggag    300
aagttgcctc attttgtgat tggggaggtg gattggacta ctaccggcgg ggcagagaat    360
actgtcacga aggatggaca ggtttcggag cttatcaagg atttcagaga gttgggtgaa    420
cacttcgaca ggttggggta ctttcacgtc agtccatggt attacgtccg taaggtggct    480
accgtcttcg ccatctttgg atgtgcactc ggactcctct tcaataccga ttccatccca    540
gcacacatgc tcgcggcggt actcctcggt atattctggc aacaatttgc attcgtcgga    600
catgactgtg gtcacatgtc ggcgcggact catgcccgtg atcatatcga tgtacctaag    660
ctgggagcac tggtgacctt cttcaatggg atttcggtag cgtggtggaa ggctacgcac    720
aatgttcatc atgctgtgcc aaatagtgtt gattgtgacc cggacattgc tcatttgccg    780
gtgtttgcgt tgcatgagca catgtttacg tcgttgttta caagtatca tgggagggtg    840

-continued

```
atggagtttg attggctggc gcgtaatgtc tttgtgccat ttcaacactt ttggtactat    900
cccataatgg cggtggcgag gttcaatctg tacattcaat cagcattgtt tttggcgtcg    960
aagaacgatg ggcatgcagg aagaacaaca ttggatttga tggcgttcat cggcttcttc   1020
tcttggttag cggtgctggt gtcatgcatc ccgagctggc cggagcgtat cgcattcgtc   1080
ttcgtcagcc atgctgtagc tgggttactg aatgtgcaaa tcacactgtc gcacttctct   1140
cggccaatct tgataccaa caagaggga cccaggtttg gaggtgactt ttactctcgt    1200
aacgtccttg cttcgttgga cgtcgcttgt cctacatact tggactggtt ccacggaggt   1260
ctccaattcc aaacactcca tcattgctac cctagacttg acgtcagca cttgagaaag    1320
accgaacctc tcattgcatc gttgtgcaag aagcattctt taccatacac gagcaagagc   1380
ttcgtagagt gcaatatgga agtttttaat acattgaagg atgccgcgcg ttctgccaag   1440
aagtggtcac cgttaattta tgagtcaatg tgtgctcagg gatag                   1485
```

<210> SEQ ID NO 21
<211> LENGTH: 494
<212> TYPE: PRT
<213> ORGANISM: Thalassiosira pseudonana

<400> SEQUENCE: 21

```
Met Ala Pro Pro Ser Ile Lys Asp Thr Leu Asp Glu Pro Phe Val Ser
1               5                   10                  15

Pro Ala Ser Thr Lys Ser Pro Thr Thr Lys Pro Leu Leu Pro Arg Arg
                20                  25                  30

Lys Pro Leu Lys Arg Tyr Ser Pro Ser Gln Ile Ser Gln His Asn Thr
            35                  40                  45

Pro Thr Asp Ala Trp Leu Ile Tyr Lys Ser Gln Val Leu Asp Ile Ser
        50                  55                  60

Lys Trp Ile Ser His His Pro Gly Gly Glu Gln Thr Leu Leu Arg Phe
65                  70                  75                  80

Ala Gly Met Asp Ala Thr Asp Glu Leu Arg Ala Phe His Asp Asp Trp
                85                  90                  95

Val Leu Glu Glu Lys Leu Pro His Phe Val Ile Gly Glu Val Asp Trp
            100                 105                 110

Thr Thr Thr Gly Gly Ala Glu Asn Thr Val Thr Lys Asp Gly Gln Val
        115                 120                 125

Ser Glu Leu Ile Lys Asp Phe Arg Glu Leu Gly Glu His Phe Asp Arg
130                 135                 140

Leu Gly Tyr Phe His Val Ser Pro Trp Tyr Tyr Val Arg Lys Val Ala
145                 150                 155                 160

Thr Val Phe Ala Ile Phe Gly Cys Ala Leu Gly Leu Leu Phe Asn Thr
                165                 170                 175

Asp Ser Ile Pro Ala His Met Leu Ala Ala Val Leu Leu Gly Ile Phe
            180                 185                 190

Trp Gln Gln Phe Ala Phe Val Gly His Asp Cys Gly His Met Ser Ala
        195                 200                 205

Arg Thr His Ala Arg Asp His Ile Asp Val Pro Lys Leu Gly Ala Leu
    210                 215                 220

Val Thr Phe Phe Asn Gly Ile Ser Val Ala Trp Trp Lys Ala Thr His
225                 230                 235                 240

Asn Val His His Ala Val Pro Asn Ser Val Asp Cys Asp Pro Asp Ile
                245                 250                 255

Ala His Leu Pro Val Phe Ala Leu His Glu His Met Phe Thr Ser Leu
            260                 265                 270
```

```
Phe Asn Lys Tyr His Gly Arg Val Met Glu Phe Asp Trp Leu Ala Arg
    275                 280                 285

Asn Val Phe Val Pro Phe Gln His Phe Trp Tyr Tyr Pro Ile Met Ala
290                 295                 300

Val Ala Arg Phe Asn Leu Tyr Ile Gln Ser Ala Leu Phe Leu Ala Ser
305                 310                 315                 320

Lys Asn Asp Gly His Ala Gly Arg Thr Thr Leu Asp Leu Met Ala Phe
                325                 330                 335

Ile Gly Phe Phe Ser Trp Leu Ala Val Leu Val Ser Cys Ile Pro Ser
                340                 345                 350

Trp Pro Glu Arg Ile Ala Phe Val Phe Val Ser His Ala Val Ala Gly
                355                 360                 365

Leu Leu Asn Val Gln Ile Thr Leu Ser His Phe Ser Arg Pro Ile Phe
        370                 375                 380

Asp Thr Asn Lys Glu Gly Pro Arg Phe Gly Gly Asp Phe Tyr Ser Arg
385                 390                 395                 400

Asn Val Leu Ala Ser Leu Asp Val Ala Cys Pro Thr Tyr Leu Asp Trp
                405                 410                 415

Phe His Gly Gly Leu Gln Phe Gln Thr Leu His His Cys Tyr Pro Arg
                420                 425                 430

Leu Gly Arg Gln His Leu Arg Lys Thr Glu Pro Leu Ile Ala Ser Leu
            435                 440                 445

Cys Lys Lys His Ser Leu Pro Tyr Thr Ser Lys Ser Phe Val Glu Cys
    450                 455                 460

Asn Met Glu Val Phe Asn Thr Leu Lys Asp Ala Ala Arg Ser Ala Lys
465                 470                 475                 480

Lys Trp Ser Pro Leu Ile Tyr Glu Ser Met Cys Ala Gln Gly
                485                 490
```

<210> SEQ ID NO 22
<211> LENGTH: 16
<212> TYPE: DNA
<213> ORGANISM: Thalassiosira pseudonana

<400> SEQUENCE: 22
ggtaacgaat tgttag                                                     16

<210> SEQ ID NO 23
<211> LENGTH: 16
<212> TYPE: DNA
<213> ORGANISM: Thalassiosira pseudonana

<400> SEQUENCE: 23
gtcggcatag tttatg                                                     16

<210> SEQ ID NO 24
<211> LENGTH: 21
<212> TYPE: DNA
<213> ORGANISM: Thalassiosira pseudonana

<400> SEQUENCE: 24
gtgagagcac taaccaagct t                                               21

<210> SEQ ID NO 25
<211> LENGTH: 19
<212> TYPE: DNA
<213> ORGANISM: Thalassiosira pseudonana -continued

```
<400> SEQUENCE: 25
caatcagtag gcttcgtcg                                                  19

<210> SEQ ID NO 26
<211> LENGTH: 33
<212> TYPE: DNA
<213> ORGANISM: Thalassiosira pseudonana

<400> SEQUENCE: 26
gcgggatcca ccatggctgg aaaaggagga gac                                  33

<210> SEQ ID NO 27
<211> LENGTH: 26
<212> TYPE: DNA
<213> ORGANISM: Thalassiosira pseudonana

<400> SEQUENCE: 27
gcgaattctt acatggcagg gaaatc                                          26

<210> SEQ ID NO 28
<211> LENGTH: 33
<212> TYPE: DNA
<213> ORGANISM: Thalassiosira pseudonana

<400> SEQUENCE: 28
gcgggatcca ccatggctga ctttctctcc ggc                                  33

<210> SEQ ID NO 29
<211> LENGTH: 26
<212> TYPE: DNA
<213> ORGANISM: Thalassiosira pseudonana

<400> SEQUENCE: 29
gcgaattctc aatcagtagg cttcgt                                          26

<210> SEQ ID NO 30
<211> LENGTH: 444
<212> TYPE: PRT
<213> ORGANISM: Danio rerio

<400> SEQUENCE: 30
```

Met Gly Gly Gly Gly Gln Gln Thr Asp Arg Ile Thr Asp Thr Asn Gly
1               5                   10                  15

Arg Phe Ser Ser Tyr Thr Trp Glu Glu Val Gln Lys His Thr Lys His
            20                  25                  30

Gly Asp Gln Trp Val Val Val Glu Arg Lys Val Tyr Asn Val Ser Gln
        35                  40                  45

Trp Val Lys Arg His Pro Gly Gly Leu Arg Ile Leu Gly His Tyr Ala
    50                  55                  60

Gly Glu Asp Ala Thr Glu Ala Phe Thr Ala Phe His Pro Asn Leu Gln
65                  70                  75                  80

Leu Val Arg Lys Tyr Leu Lys Pro Leu Leu Ile Gly Glu Leu Glu Ala
                85                  90                  95

Ser Glu Pro Ser Gln Asp Arg Gln Lys Asn Ala Ala Leu Val Glu Asp
            100                 105                 110

Phe Arg Ala Leu Arg Glu Arg Leu Glu Ala Glu Gly Cys Phe Lys Thr
        115                 120                 125

Gln Pro Leu Phe Phe Ala Leu His Leu Gly His Ile Leu Leu Leu Glu
    130                 135                 140

Ala Ile Ala Phe Met Met Val Trp Tyr Phe Gly Thr Gly Trp Ile Asn
145                 150                 155                 160

Thr Leu Ile Val Ala Val Ile Leu Ala Thr Ala Gln Ser Gln Ala Gly
            165                 170                 175

Trp Leu Gln His Asp Phe Gly His Leu Ser Val Phe Lys Thr Ser Gly
        180                 185                 190

Met Asn His Leu Val His Lys Phe Val Ile Gly His Leu Lys Gly Ala
    195                 200                 205

Ser Ala Gly Trp Trp Asn His Arg His Phe Gln His Ala Lys Pro
210                 215                 220

Asn Ile Phe Lys Lys Asp Pro Asp Val Asn Met Leu Asn Ala Phe Val
225                 230                 235                 240

Val Gly Asn Val Gln Pro Val Glu Tyr Gly Val Lys Lys Ile Lys His
            245                 250                 255

Leu Pro Tyr Asn His Gln His Lys Tyr Phe Phe Phe Ile Gly Pro Pro
        260                 265                 270

Leu Leu Ile Pro Val Tyr Phe Gln Phe Gln Ile Phe His Asn Met Ile
    275                 280                 285

Ser His Gly Met Trp Val Asp Leu Leu Trp Cys Ile Ser Tyr Tyr Val
    290                 295                 300

Arg Tyr Phe Leu Cys Tyr Thr Gln Phe Tyr Gly Val Phe Trp Ala Ile
305                 310                 315                 320

Ile Leu Phe Asn Phe Val Arg Phe Met Glu Ser His Trp Phe Val Trp
            325                 330                 335

Val Thr Gln Met Ser His Ile Pro Met Asn Ile Asp Tyr Glu Lys Asn
        340                 345                 350

Gln Asp Trp Leu Ser Met Gln Leu Val Ala Thr Cys Asn Ile Glu Gln
    355                 360                 365

Ser Ala Phe Asn Asp Trp Phe Ser Gly His Leu Asn Phe Gln Ile Glu
    370                 375                 380

His His Leu Phe Pro Thr Val Pro Arg His Asn Tyr Trp Arg Ala Ala
385                 390                 395                 400

Pro Arg Val Arg Ala Leu Cys Glu Lys Tyr Gly Val Lys Tyr Gln Glu
            405                 410                 415

Lys Thr Leu Tyr Gly Ala Phe Ala Asp Ile Ile Arg Ser Leu Glu Lys
        420                 425                 430

Ser Gly Glu Leu Trp Leu Asp Ala Tyr Leu Asn Lys
    435                 440

<210> SEQ ID NO 31
<211> LENGTH: 444
<212> TYPE: PRT
<213> ORGANISM: Homo sapiens

<400> SEQUENCE: 31

Met Gly Lys Gly Gly Asn Gln Gly Glu Gly Ala Ala Glu Arg Glu Val
1               5                   10                  15

Ser Val Pro Thr Phe Ser Trp Glu Glu Ile Gln Lys His Asn Leu Arg
            20                  25                  30

Thr Asp Arg Trp Leu Val Ile Asp Arg Lys Val Tyr Asn Ile Thr Lys
        35                  40                  45

Trp Ser Ile Gln His Pro Gly Gly Gln Arg Val Ile Gly His Tyr Ala
    50                  55                  60

Gly Glu Asp Ala Thr Asp Ala Phe Arg Ala Phe His Pro Asp Leu Glu
65                  70                  75                  80

Phe Val Gly Lys Phe Leu Lys Pro Leu Leu Ile Gly Glu Leu Ala Pro
                85                  90                  95

Glu Glu Pro Ser Gln Asp His Gly Lys Asn Ser Lys Ile Thr Glu Asp
            100                 105                 110

Phe Arg Ala Leu Arg Lys Thr Ala Glu Asp Met Asn Leu Phe Lys Thr
        115                 120                 125

Asn His Val Phe Phe Leu Leu Leu Ala His Ile Ile Ala Leu Glu
    130                 135                 140

Ser Ile Ala Trp Phe Thr Val Phe Tyr Phe Gly Asn Gly Trp Ile Pro
145                 150                 155                 160

Thr Leu Ile Thr Ala Phe Val Leu Ala Thr Ser Gln Ala Gln Ala Gly
                165                 170                 175

Trp Leu Gln His Asp Tyr Gly His Leu Ser Val Tyr Arg Lys Pro Lys
            180                 185                 190

Trp Asn His Leu Val His Lys Phe Val Ile Gly His Leu Lys Gly Ala
        195                 200                 205

Ser Ala Asn Trp Trp Asn His Arg His Phe Gln His His Ala Lys Pro
210                 215                 220

Asn Ile Phe His Lys Asp Pro Asp Val Asn Met Leu His Val Phe Val
225                 230                 235                 240

Leu Gly Glu Trp Gln Pro Ile Glu Tyr Gly Lys Lys Lys Leu Lys Tyr
                245                 250                 255

Leu Pro Tyr Asn His Gln His Glu Tyr Phe Phe Leu Ile Gly Pro Pro
            260                 265                 270

Leu Leu Ile Pro Met Tyr Phe Gln Tyr Gln Ile Ile Met Thr Met Ile
        275                 280                 285

Val His Lys Asn Trp Val Asp Leu Ala Trp Ala Val Ser Tyr Tyr Ile
    290                 295                 300

Arg Phe Phe Ile Thr Tyr Ile Pro Phe Tyr Gly Ile Leu Gly Ala Leu
305                 310                 315                 320

Leu Phe Leu Asn Phe Ile Arg Phe Leu Glu Ser His Trp Phe Val Trp
                325                 330                 335

Val Thr Gln Met Asn His Ile Val Met Glu Ile Asp Gln Glu Ala Tyr
            340                 345                 350

Arg Asp Trp Phe Ser Ser Gln Leu Thr Ala Thr Cys Asn Val Glu Gln
        355                 360                 365

Ser Phe Phe Asn Asp Trp Phe Ser Gly His Leu Asn Phe Gln Ile Glu
    370                 375                 380

His His Leu Phe Pro Thr Met Pro Arg His Asn Leu His Lys Ile Ala
385                 390                 395                 400

Pro Leu Val Lys Ser Leu Cys Ala Lys His Gly Ile Glu Tyr Gln Glu
                405                 410                 415

Lys Pro Leu Leu Arg Ala Leu Leu Asp Ile Ile Arg Ser Leu Lys Lys
            420                 425                 430

Ser Gly Lys Leu Trp Leu Asp Ala Tyr Leu His Lys
        435                 440

<210> SEQ ID NO 32
<211> LENGTH: 444
<212> TYPE: PRT
<213> ORGANISM: Homo sapiens

<400> SEQUENCE: 32

```
Met Ala Pro Asp Pro Val Ala Ala Glu Thr Ala Ala Gln Gly Pro Thr
1               5                  10                  15

Pro Arg Tyr Phe Thr Trp Asp Glu Val Ala Gln Arg Ser Gly Cys Glu
            20                  25                  30

Glu Arg Trp Leu Val Ile Asp Arg Lys Val Tyr Asn Ile Ser Glu Phe
        35                  40                  45

Thr Arg Arg His Pro Gly Gly Ser Arg Val Ile Ser His Tyr Ala Gly
    50                  55                  60

Gln Asp Ala Thr Asp Pro Phe Val Ala Phe His Ile Asn Lys Gly Leu
65                  70                  75                  80

Val Lys Lys Tyr Met Asn Ser Leu Leu Ile Gly Glu Leu Ser Pro Glu
                85                  90                  95

Gln Pro Ser Phe Glu Pro Thr Lys Asn Lys Glu Leu Thr Asp Glu Phe
            100                 105                 110

Arg Glu Leu Arg Ala Thr Val Glu Arg Met Gly Leu Met Lys Ala Asn
        115                 120                 125

His Val Phe Phe Leu Leu Tyr Leu Leu His Ile Leu Leu Leu Asp Gly
    130                 135                 140

Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
            180                 185                 190

Asn His Leu Leu His His Phe Val Ile Gly His Leu Lys Gly Ala Pro
        195                 200                 205

Ala Ser Trp Trp Asn His Met His Phe Gln His His Ala Lys Pro Asn
    210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
            260                 265                 270

Ala Leu Leu Pro Leu Tyr Phe Gln Trp Tyr Ile Phe Tyr Phe Val Ile
        275                 280                 285

Gln Arg Lys Lys Trp Val Asp Leu Ala Trp Met Ile Thr Phe Tyr Val
    290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
            340                 345                 350

Met Asp Trp Val Ser Thr Gln Leu Gln Ala Thr Cys Asn Val His Lys
        355                 360                 365

Ser Ala Phe Asn Asp Trp Phe Ser Gly His Leu Asn Phe Gln Ile Glu
    370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
                405                 410                 415
```

-continued

Lys Pro Leu Leu Ser Ala Phe Ala Asp Ile Ile His Ser Leu Lys Glu
            420                 425                 430

Ser Gly Gln Leu Trp Leu Asp Ala Tyr Leu His Gln
        435                 440

<210> SEQ ID NO 33
<211> LENGTH: 439
<212> TYPE: PRT
<213> ORGANISM: Thraustochytrium sp.

<400> SEQUENCE: 33

Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
            20                  25                  30

Tyr Asp Ala Thr Asn Phe Lys His Pro Gly Gly Ser Ile Ile Asn Phe
        35                  40                  45

Leu Thr Glu Gly Glu Ala Gly Val Asp Ala Thr Gln Ala Tyr Arg Glu
    50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
            180                 185                 190

Tyr Gly Val Gly Cys Gly Met Ser Gly His Tyr Trp Lys Asn Gln His
        195                 200                 205

Ser Lys His His Ala Ala Pro Asn Arg Leu Glu His Asp Val Asp Leu
    210                 215                 220

Asn Thr Leu Pro Leu Val Ala Phe Asn Glu Arg Val Val Arg Lys Val
225                 230                 235                 240

Lys Pro Gly Ser Leu Leu Ala Leu Trp Leu Arg Val Gln Ala Tyr Leu
                245                 250                 255

Phe Ala Pro Val Ser Cys Leu Leu Ile Gly Leu Gly Trp Thr Leu Tyr
            260                 265                 270

Leu His Pro Arg Tyr Met Leu Arg Thr Lys Arg His Met Glu Phe Val
        275                 280                 285

Trp Ile Phe Ala Arg Tyr Ile Gly Trp Phe Ser Leu Met Gly Ala Leu
    290                 295                 300

Gly Tyr Ser Pro Gly Thr Ser Val Gly Met Tyr Leu Cys Ser Phe Gly
305                 310                 315                 320

Leu Gly Cys Ile Tyr Ile Phe Leu Gln Phe Ala Val Ser His Thr His
                325                 330                 335

Leu Pro Val Thr Asn Pro Glu Asp Gln Leu His Trp Leu Glu Tyr Ala
            340                 345                 350

```
Ala Asp His Thr Val Asn Ile Ser Thr Lys Ser Trp Leu Val Thr Trp
            355                 360                 365

Trp Met Ser Asn Leu Asn Phe Gln Ile Glu His His Leu Phe Pro Thr
    370                 375                 380

Ala Pro Gln Phe Arg Phe Lys Glu Ile Ser Pro Arg Val Glu Ala Leu
385                 390                 395                 400

Phe Lys Arg His Asn Leu Pro Tyr Tyr Asp Leu Pro Tyr Thr Ser Ala
                405                 410                 415

Val Ser Thr Thr Phe Ala Asn Leu Tyr Ser Val Gly His Ser Val Gly
            420                 425                 430

Ala Asp Thr Lys Lys Gln Asp
            435

<210> SEQ ID NO 34
<211> LENGTH: 443
<212> TYPE: PRT
<213> ORGANISM: Caenorhabditis elegans

<400> SEQUENCE: 34

Met Val Val Asp Lys Asn Ala Ser Gly Leu Arg Met Lys Val Asp Gly
1               5                   10                  15

Lys Trp Leu Tyr Leu Ser Glu Glu Leu Val Lys His Pro Gly Gly
            20                  25                  30

Ala Val Ile Glu Gln Tyr Arg Asn Ser Asp Ala Thr Ile Phe His
        35                  40                  45

Ala Phe His Glu Gly Ser Ser Gln Ala Tyr Lys Gln Leu Asp Leu Leu
    50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Gly Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys Asn Thr His
        195                 200                 205

His Ala Ala Thr Asn Val Ile Asp His Asp Gly Asp Ile Asp Leu Ala
    210                 215                 220

Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
                245                 250                 255

Thr Ala Met Leu Pro Met Leu Arg Phe Ser Trp Thr Gly Gln Ser Val
            260                 265                 270

Gln Trp Val Phe Lys Glu Asn Gln Met Glu Tyr Lys Val Tyr Gln Arg
        275                 280                 285
```

```
Asn Ala Phe Trp Glu Gln Ala Thr Ile Val Gly His Trp Ala Trp Val
            290                 295                 300

Phe Tyr Gln Leu Phe Leu Leu Pro Thr Trp Pro Leu Arg Val Ala Tyr
305                 310                 315                 320

Phe Ile Ile Ser Gln Met Gly Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
    370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Gln Leu Lys
            420                 425                 430

Asn Met Ala Glu His Ile Gln Ala Lys Ala Ala
        435                 440

<210> SEQ ID NO 35
<211> LENGTH: 443
<212> TYPE: PRT
<213> ORGANISM: Caenorhabditis elegans

<400> SEQUENCE: 35

Met Val Val Asp Lys Asn Ala Ser Gly Leu Arg Met Lys Val Asp Gly
1               5                   10                  15

Lys Trp Leu Tyr Leu Ser Glu Glu Leu Val Lys Lys His Pro Gly Gly
            20                  25                  30

Ala Val Ile Glu Gln Tyr Arg Asn Ser Asp Ala Thr His Ile Phe His
        35                  40                  45

Ala Phe His Glu Gly Ser Ser Gln Ala Tyr Lys Gln Leu Asp Leu Leu
    50                  55                  60

Lys Lys His Gly Glu His Asp Glu Phe Leu Glu Lys Gln Leu Glu Lys
65                  70                  75                  80

Arg Leu Asp Lys Val Asp Ile Asn Val Ser Ala Tyr Asp Val Ser Val
                85                  90                  95

Ala Gln Glu Lys Lys Met Val Gly Ser Phe Glu Lys Leu Arg Gln Lys
            100                 105                 110

Leu His Asp Asp Gly Leu Met Lys Ala Asn Glu Thr Tyr Phe Leu Phe
        115                 120                 125

Lys Ala Ile Ser Thr Leu Ser Ile Met Ala Phe Ala Phe Tyr Leu Gln
    130                 135                 140

Tyr Leu Gly Trp Tyr Ile Thr Ser Ala Cys Leu Leu Ala Leu Ala Trp
145                 150                 155                 160

Gln Gln Phe Gly Trp Leu Thr His Glu Phe Cys His Gln Gln Pro Thr
                165                 170                 175

Lys Asn Arg Pro Leu Asn Asp Thr Ile Ser Leu Phe Phe Gly Asn Phe
            180                 185                 190

Leu Gln Gly Phe Ser Arg Asp Trp Trp Lys Asp Lys His Asn Thr His
        195                 200                 205

His Ala Ala Thr Asn Val Ile Asp His Asp Gly Asp Ile Asp Leu Ala
    210                 215                 220
```

```
Pro Leu Phe Ala Phe Ile Pro Gly Asp Leu Cys Lys Tyr Lys Ala Ser
225                 230                 235                 240

Phe Glu Lys Ala Ile Leu Lys Ile Val Pro Tyr Gln His Leu Tyr Phe
            245                 250                 255

Thr Ala Met Leu Pro Met Leu Arg Phe Ser Trp Thr Gly Gln Ser Val
        260                 265                 270

Gln Trp Val Phe Lys Glu Asn Gln Met Glu Tyr Lys Val Tyr Gln Arg
    275                 280                 285

Asn Ala Phe Trp Glu Gln Ala Thr Ile Val Gly His Trp Ala Trp Val
290                 295                 300

Phe Tyr Gln Leu Phe Leu Leu Pro Thr Trp Pro Leu Arg Val Ala Tyr
305                 310                 315                 320

Phe Ile Ile Ser Gln Met Gly Gly Gly Leu Leu Ile Ala His Val Val
                325                 330                 335

Thr Phe Asn His Asn Ser Val Asp Lys Tyr Pro Ala Asn Ser Arg Ile
            340                 345                 350

Leu Asn Asn Phe Ala Ala Leu Gln Ile Leu Thr Thr Arg Asn Met Thr
        355                 360                 365

Pro Ser Pro Phe Ile Asp Trp Leu Trp Gly Gly Leu Asn Tyr Gln Ile
370                 375                 380

Glu His His Leu Phe Pro Thr Met Pro Arg Cys Asn Leu Asn Ala Cys
385                 390                 395                 400

Val Lys Tyr Val Lys Glu Trp Cys Lys Glu Asn Asn Leu Pro Tyr Leu
                405                 410                 415

Val Asp Asp Tyr Phe Asp Gly Tyr Ala Met Asn Leu Gln Leu Leu Lys
            420                 425                 430

Asn Met Ala Glu His Ile Gln Ala Lys Ala Ala
        435                 440

<210> SEQ ID NO 36
<211> LENGTH: 419
<212> TYPE: PRT
<213> ORGANISM: Euglena gracilis

<400> SEQUENCE: 36

Met Lys Ser Lys Arg Gln Ala Leu Ser Pro Leu Gln Leu Met Glu Gln
1               5                   10                  15

Thr Tyr Asp Val Val Asn Phe His Pro Gly Gly Ala Glu Ile Ile Glu
            20                  25                  30

Asn Tyr Gln Gly Arg Asp Ala Thr Asp Ala Phe Met Val Met His Phe
        35                  40                  45

Gln Glu Ala Phe Asp Lys Leu Lys Arg Met Pro Lys Ile Asn Pro Ser
    50                  55                  60

Phe Glu Leu Pro Pro Gln Ala Ala Val Asn Glu Ala Gln Glu Asp Phe
65                  70                  75                  80

Arg Lys Leu Arg Glu Glu Leu Ile Ala Thr Gly Met Phe Asp Ala Ser
                85                  90                  95

Pro Leu Trp Tyr Ser Tyr Lys Ile Ser Thr Thr Leu Gly Leu Gly Val
            100                 105                 110

Leu Gly Tyr Phe Leu Met Val Gln Tyr Gln Met Tyr Phe Ile Gly Ala
        115                 120                 125

Val Leu Leu Gly Met His Tyr Gln Gln Met Gly Trp Leu Ser His Asp
    130                 135                 140

Ile Cys His His Gln Thr Phe Lys Asn Arg Asn Trp Asn Asn Leu Val
145                 150                 155                 160
```

```
Gly Leu Val Phe Gly Asn Gly Leu Gln Gly Phe Ser Val Thr Cys Trp
                165                 170                 175

Lys Asp Arg His Asn Ala His His Ser Ala Thr Asn Val Gln Gly His
            180                 185                 190

Asp Pro Asp Ile Asp Asn Leu Pro Leu Ala Trp Ser Glu Asp Asp
            195                 200                 205

Val Thr Arg Ala Ser Pro Ile Ser Arg Lys Leu Ile Gln Phe Gln Gln
    210                 215                 220

Tyr Tyr Phe Leu Val Ile Cys Ile Leu Leu Arg Phe Ile Trp Cys Phe
225                 230                 235                 240

Gln Cys Val Leu Thr Val Arg Ser Leu Lys Asp Arg Asp Asn Gln Phe
                245                 250                 255

Tyr Arg Ser Gln Tyr Lys Lys Glu Ala Ile Gly Leu Ala Leu His Trp
            260                 265                 270

Thr Leu Lys Ala Leu Phe His Leu Phe Phe Met Pro Ser Ile Leu Thr
        275                 280                 285

Ser Leu Leu Val Phe Phe Val Ser Glu Leu Val Gly Gly Phe Gly Ile
    290                 295                 300

Ala Ile Val Val Phe Met Asn His Tyr Pro Leu Glu Lys Ile Gly Asp
305                 310                 315                 320

Pro Val Trp Asp Gly His Gly Phe Ser Val Gly Gln Ile His Glu Thr
                325                 330                 335

Met Asn Ile Arg Arg Gly Ile Ile Thr Asp Trp Phe Phe Gly Gly Leu
            340                 345                 350

Asn Tyr Gln Ile Glu His His Leu Trp Pro Thr Leu Pro Arg His Asn
        355                 360                 365

Leu Thr Ala Val Ser Tyr Gln Val Glu Gln Leu Cys Gln Lys His Asn
    370                 375                 380

Leu Pro Tyr Arg Asn Pro Leu Pro His Glu Gly Leu Val Ile Leu Leu
385                 390                 395                 400

Arg Tyr Leu Ala Val Phe Ala Arg Met Ala Glu Lys Gln Pro Ala Gly
                405                 410                 415

Lys Ala Leu

<210> SEQ ID NO 37
<211> LENGTH: 477
<212> TYPE: PRT
<213> ORGANISM: Phaeodactylum tricornutum

<400> SEQUENCE: 37

Met Gly Lys Gly Gly Asp Ala Arg Ala Ser Lys Gly Ser Thr Ala Ala
1               5                   10                  15

Arg Lys Ile Ser Trp Gln Glu Val Lys Thr His Ala Ser Pro Glu Asp
            20                  25                  30

Ala Trp Ile Ile His Ser Asn Lys Val Tyr Asp Val Ser Asn Trp His
        35                  40                  45

Glu His Pro Gly Gly Ala Val Ile Phe Thr His Ala Gly Asp Asp Met
    50                  55                  60

Thr Asp Ile Phe Ala Ala Phe His Ala Pro Gly Ser Gln Ser Leu Met
65                  70                  75                  80

Lys Lys Phe Tyr Ile Gly Glu Leu Leu Pro Glu Thr Thr Gly Lys Glu
                85                  90                  95
```

```
Pro Gln Gln Ile Ala Phe Glu Lys Gly Tyr Arg Asp Leu Arg Ser Lys
                100                 105                 110

Leu Ile Met Met Gly Met Phe Lys Ser Asn Lys Trp Phe Tyr Val Tyr
            115                 120                 125

Lys Cys Leu Ser Asn Met Ala Ile Trp Ala Ala Cys Ala Leu Val
130                 135                 140

Phe Tyr Ser Asp Arg Phe Trp Val His Leu Ala Ser Ala Val Met Leu
145                 150                 155                 160

Gly Thr Phe Phe Gln Ser Gly Trp Leu Ala His Asp Phe Leu His
                165                 170                 175

His Gln Val Phe Thr Lys Arg Lys His Gly Asp Leu Gly Gly Leu Phe
            180                 185                 190

Trp Gly Asn Leu Met Gln Gly Tyr Ser Val Gln Trp Trp Lys Asn Lys
                195                 200                 205

His Asn Gly His His Ala Val Pro Asn Leu His Cys Ser Ser Ala Val
                210                 215                 220

Ala Gln Asp Gly Asp Pro Asp Ile Asp Thr Met Pro Leu Leu Ala Trp
225                 230                 235                 240

Ser Val Gln Gln Ala Gln Ser Tyr Arg Glu Leu Gln Ala Asp Gly Lys
                245                 250                 255

Asp Ser Gly Leu Val Lys Phe Met Ile Arg Asn Gln Ser Tyr Phe Tyr
                260                 265                 270

Phe Pro Ile Leu Leu Leu Ala Arg Leu Ser Trp Leu Asn Glu Ser Phe
                275                 280                 285

Lys Cys Ala Phe Gly Leu Gly Ala Ala Ser Glu Asn Ala Ala Leu Glu
290                 295                 300

Leu Lys Ala Lys Gly Leu Gln Tyr Pro Leu Leu Glu Lys Ala Gly Ile
305                 310                 315                 320

Leu Leu His Tyr Ala Trp Met Leu Thr Val Ser Ser Gly Phe Gly Arg
                325                 330                 335

Phe Ser Phe Ala Tyr Thr Ala Phe Tyr Phe Leu Thr Ala Thr Ala Ser
                340                 345                 350

Cys Gly Phe Leu Leu Ala Ile Val Phe Gly Leu Gly His Asn Gly Met
                355                 360                 365

Ala Thr Tyr Asn Ala Asp Ala Arg Pro Asp Phe Trp Lys Leu Gln Val
                370                 375                 380

Thr Thr Thr Arg Asn Val Thr Gly Gly His Gly Phe Pro Gln Ala Phe
385                 390                 395                 400

Val Asp Trp Phe Cys Gly Gly Leu Gln Tyr Gln Val Asp His His Leu
                405                 410                 415

Phe Pro Ser Leu Pro Arg His Asn Leu Ala Lys Thr His Ala Leu Val
                420                 425                 430

Glu Ser Phe Cys Lys Glu Trp Gly Val Gln Tyr His Glu Ala Asp Leu
                435                 440                 445

Val Asp Gly Thr Met Glu Val Leu His His Leu Gly Ser Val Ala Gly
            450                 455                 460

Glu Phe Val Val Asp Phe Val Arg Asp Gly Pro Ala Met
465                 470                 475

<210> SEQ ID NO 38
<211> LENGTH: 404
<212> TYPE: PRT
<213> ORGANISM: Borago officinalis
```

<400> SEQUENCE: 38

```
Ser Phe Pro Leu Lys Ser Leu Ala Gly Gln Glu Val Thr Asp Ala Phe
1               5                   10                  15

Val Ala Phe His Pro Ala Ser Thr Trp Lys Asn Leu Asp Lys Phe Phe
            20                  25                  30

Thr Gly Tyr Tyr Leu Lys Asp Tyr Ser Val Ser Glu Val Ser Lys Asp
        35                  40                  45

Tyr Arg Lys Leu Val Phe Glu Phe Ser Lys Met Gly Leu Tyr Asp Lys
    50                  55                  60

Lys Gly His Ile Met Phe Ala Thr Leu Cys Phe Ile Ala Met Leu Phe
65                  70                  75                  80

Ala Met Ser Val Tyr Gly Val Leu Phe Cys Glu Gly Val Leu Val His
            85                  90                  95

Leu Phe Ser Gly Cys Leu Met Gly Phe Leu Trp Ile Gln Ser Gly Trp
            100                 105                 110

Ile Gly His Asp Ala Gly His Tyr Met Val Ser Ser Arg Leu
            115                 120                 125

Asn Lys Phe Met Gly Ile Phe Ala Ala Asn Cys Leu Ser Gly Ile Ser
    130                 135                 140

Ile Gly Trp Trp Lys Trp Asn His Asn Ala His His Ile Ala Cys Asn
145                 150                 155                 160

Ser Leu Glu Tyr Asp Pro Asp Leu Gln Tyr Ile Pro Phe Leu Val Val
            165                 170                 175

Ser Ser Lys Phe Phe Gly Ser Leu Thr Ser His Phe Tyr Glu Lys Arg
            180                 185                 190

Leu Thr Phe Asp Ser Leu Ser Arg Phe Phe Val Ser Tyr Gln His Trp
    195                 200                 205

Thr Phe Tyr Pro Ile Met Cys Ala Ala Arg Leu Asn Met Tyr Val Gln
    210                 215                 220

Ser Leu Ile Met Leu Leu Thr Lys Arg Asn Val Ser Tyr Arg Ala His
225                 230                 235                 240

Glu Leu Leu Gly Cys Leu Val Phe Ser Ile Trp Tyr Pro Leu Leu Val
            245                 250                 255

Ser Cys Leu Pro Asn Trp Gly Glu Arg Ile Met Phe Val Ile Ala Ser
            260                 265                 270

Leu Ser Val Thr Gly Met Gln Gln Val Gln Phe Ser Leu Asn His Phe
            275                 280                 285

Ser Ser Ser Val Tyr Val Gly Lys Pro Lys Gly Asn Asn Trp Phe Glu
            290                 295                 300

Lys Gln Thr Asp Gly Thr Leu Asp Ile Ser Cys Pro Pro Trp Met Asp
305                 310                 315                 320

Trp Phe His Gly Gly Leu Gln Phe Gln Ile Glu His His Leu Phe Pro
            325                 330                 335

Lys Met Pro Arg Cys Asn Leu Arg Lys Ile Ser Pro Tyr Val Ile Glu
            340                 345                 350

Leu Cys Lys Lys His Asn Leu Pro Tyr Asn Tyr Ala Ser Phe Ser Lys
            355                 360                 365

Ala Asn Glu Met Thr Leu Arg Thr Leu Arg Asn Thr Ala Leu Gln Ala
            370                 375                 380

Arg Asp Ile Thr Lys Pro Leu Pro Lys Asn Leu Val Trp Glu Ala Leu
385                 390                 395                 400

His Thr His Gly
```

The invention claimed is:

1. A transgenic cell comprising a polynucleotide molecule which comprises SEQ ID NO:9.

2. The transgenic cell according to claim 1, wherein the cell comprises an expression vector which comprises the polynucleotide molecule and an expression regulatory element operably linked thereto.

3. The transgenic cell according to claim 2, wherein the expression regulatory element is a promoter.

4. The cell according to claim 1, wherein the cell overexpresses the polypeptide which has desaturase activity.

5. The cell according to claim 1, wherein the transgenic cell is a eukaryotic cell.

6. The cell according to claim 5, wherein the cell is a plant cell.

7. A plant comprising a cell according to claim 6.

8. The plant according to claim 7, wherein the plant is an oil seed plant.

9. A seed comprising a cell according to claim 6.

10. The seed according to claim 9, wherein the seed is an oil plant seed.

11. The cell according to claim 1, wherein the cell is a prokaryotic cell.

12. A reaction vessel comprising a transgenic cell of claim 1.

13. The vessel according to claim 12, wherein the cell is a yeast cell.

14. The vessel according to claim 12, wherein the cell is a prokaryotic cell.

15. A method to desaturate a fatty acid substrate comprising the steps of: i) providing a reaction vessel according to claim 12; and ii) culturing the cell contained in the reaction vessel under conditions which allow desaturation of at least one fatty acid substrate.

* * * * *

UNITED STATES PATENT AND TRADEMARK OFFICE
CERTIFICATE OF CORRECTION

PATENT NO. : 7,951,994 B2
APPLICATION NO. : 10/597998
DATED : May 31, 2011
INVENTOR(S) : Ian Graham It is certified that error appears in the above-identified patent and that said Letters Patent is hereby corrected as shown below:

In the Specification

Col. 33, Line 42, should read:

<210> 10
<211> 1458
<212> DNA
<213> Thalassiosira pseudonana
<400> 10

ATGGCTGGAA AAGGAGGAGA CGCAGCCGCA GCTACCAAGC GTAGTGGAGC ATTGAAATTG   60

GCGGAGAAGC CGCAGAAGTA CACTTGGCAG GAGGTGAAGA AGCACATCAC CCCCGACGAT   120

GCCTGGGTAG TCCACCAAAA CAAAGTCTAC GACGTCTCCA ACTGGTACGA CCACCCCGGT   180

GGAGCCGTGG TGTTCACCCA CGCCGGAGAC GACATGACGG ACATCTTCGC CGCCTTCCAC   240

GCCCAAGGCT CTCAGGCCAT GATGAAGAAG TTTTACATTG GAGATTTGAT TCCGGAGAGT   300

GTGGAGCATA AGGATCAAAG ACAGTTGGAT TTCGAGAAGG GATATCGTGA TTTACGGGCC   360

AAGCTTGTCA TGATGGGGAT GTTCAAGTCG AGTAAGATGT ATTATGCATA CAAGTGCTCG   420

TTCAATATGT GCATGTGGTT GGTGGCGGTG GCCATGGTGT ACTACTCGGA CAGTTTGGCA   480

ATGCACATTG GATCGGCTCT CTTGTTGGGA TTGTTCTGGC AGCAGTGTGG ATGGCTTGCG   540

CACGACTTTC TTCACCACCA AGTCTTTAAG CAACGAAAGT ACGGAGATCT CGTTGGCATC   600

TTTTGGGGAG ATCTCATGCA GGGGTTCTCG ATGCAGTGGT GGAAGAACAA GCACAATGGC   660

CACCATGCTG TTCCCAACTT GCACAACTCT TCCTTGGACA GTCAGGATGG TGATCCCGAT   720

ATTGATACCA TGCCACTCCT TGCTTGGAGT CTCAAGCAGG CTCAGAGTTT CAGAGAGATC   780

AATAAGGGAA AGGACAGTAC CTTCGTCAAG TACGCTATCA AATTCCAGGC ATTCACATAC   840

(to be continued)

Signed and Sealed this
Twenty-fifth Day of February, 2014

Michelle K. Lee
*Deputy Director of the United States Patent and Trademark Office*

(continued)

```
TTCCCCATCC TCCTCTTGGC TCGCATCTCT TGGTTGAATG AATCCTTCAA AACTGCATTC   900
GGACTCGGAG CTGCCTCGGA GAATGCCAAG TTGGAGTTGG AGAAGCGTGG ACTTCAGTAC   960
CCACTTTTGG AGAAGCTTGG AATCACCCTT CACTACACTT GGATGTTCGT CCTCTCTTCC  1020
GGATTTGGAA GGTGGTCTCT TCCATATTCC ATCATGTATT TCTTCACTGC CACATGCTCC  1080
TCGGGACTTT TCCTCGCATT GGTCTTTGGA TTGGGACACA ACGGTATGTC AGTGTACGAT  1140
GCCACCACCC GACCTGACTT CTGGCAACTC CAAGTCACCA CTACACGTAA CATCATTGGT  1200
GGACACGGCA TTCCCCAATT CTTTGTGGAT TGGTTCTGCG GTGGATTGCA ATACCAAGTG  1260
GATCACCACC TCTTCCCCAT GATGCCTAGA AACAATATCG CGAAGTGCCA CAAGCTTGTG  1320
GAGTCATTCT GTAAGGAGTG GGGTGTGAAG TACCATGAGG CTGATATGTG GGATGGTACC  1380
GTGGAAGTGT TGCAACATCT CTCCAAGGTG TCGGATGATT TCCTTGTGGA GATGGTGAAG  1440
GATTTCCCTG CCATGTAA                                                1458
```